(12) United States Patent
Samsoondar et al.

(10) Patent No.: US 12,000,824 B2
(45) Date of Patent: Jun. 4, 2024

(54) POINT-OF-CARE TESTING SYSTEM, ANALYZER AND METHOD

(71) Applicant: InViDx Corp., Schomberg (CA)

(72) Inventors: James Samsoondar, Schomberg (CA); Michael Licht, Nümbrecht (DE)

(73) Assignee: INVIDX CORP., Schomberg (CA)

( * ) Notice: Subject to any disclaimer, the term of this patent is extended or adjusted under 35 U.S.C. 154(b) by 0 days.

(21) Appl. No.: 18/206,356

(22) Filed: Jun. 6, 2023

(65) Prior Publication Data
US 2024/0060957 A1 Feb. 22, 2024

(30) Foreign Application Priority Data
Aug. 17, 2022 (CA) ...................................... 3170696

(51) Int. Cl.
*G01N 33/48* (2006.01)
*B01L 3/00* (2006.01)
(Continued)

(52) U.S. Cl.
CPC ...... *G01N 33/492* (2013.01); *B01L 3/502715* (2013.01); *G01N 21/255* (2013.01); *G01N 21/33* (2013.01); *B01L 2200/04* (2013.01); *B01L 2200/16* (2013.01); *B01L 2300/0654* (2013.01); *G01N 2201/062* (2013.01); *G01N 2201/08* (2013.01)

(58) Field of Classification Search
None
See application file for complete search history.

(56) References Cited

U.S. PATENT DOCUMENTS

| 5,096,669 | A | 3/1992 | Lauks et al. |
| 6,651,015 | B2 | 11/2003 | Samsoondar |
| 7,094,330 | B2 | 8/2006 | Lauks et al. |

FOREIGN PATENT DOCUMENTS

| CA | 2978737 A1 | 10/2017 |
| WO | 2021051202 A1 | 3/2021 |
| WO | 2022056631 A1 | 3/2022 |

OTHER PUBLICATIONS

Zhang et. al., "Mid-Infrared Spectroscopy for Coffee Variety Identification: Comparison of Pattern Recognition Methods", J. of Spectroscopy, vol. 2016, Article ID 7927286.
(Continued)

*Primary Examiner* — Rebecca C Bryant
(74) *Attorney, Agent, or Firm* — Bereskin & Parr LLP/S.E.N.C.R.L., s.r.l.

(57) ABSTRACT

Described are various embodiments of a point-of-care testing (POCT) system, analyzer and method for measuring quantities of at least two analytes in a blood sample, for example bilirubin and hemoglobin. The system comprises an analyzer and a removable cartridge. The removable cartridge comprises an optical chamber configured for receiving the blood sample. The analyzer comprises a receptor for receiving the removable cartridge, a first and second set of incident electromagnetic radiation (EMR) for example two broadband LEDs, an EMR dispersive element for example a reflective grating, a photo diode array detector, and a processor. The two EMR sources are implemented in such a way so that the spectral wavelength range of EMR emerging from the blood is expanded, and the effect of stray EMR is mitigated. The expanded wavelength range and the mitigation of stray EMR allows the analyzer to measure quantities of the analytes in lysed or unlysed blood.

33 Claims, 30 Drawing Sheets

(51) Int. Cl.
    *G01N 21/25* (2006.01)
    *G01N 21/33* (2006.01)
    *G01N 33/49* (2006.01)

(56) References Cited

OTHER PUBLICATIONS

G. O. Gogstad et. al., "Turbidimetric Determination of Prothrombin Time by Clotting in a Centrifugal Analyzer" Clin. Chem., 1986, 32/10, 1857-1862.

Prior Art
Pat. No. CA 2,978,737

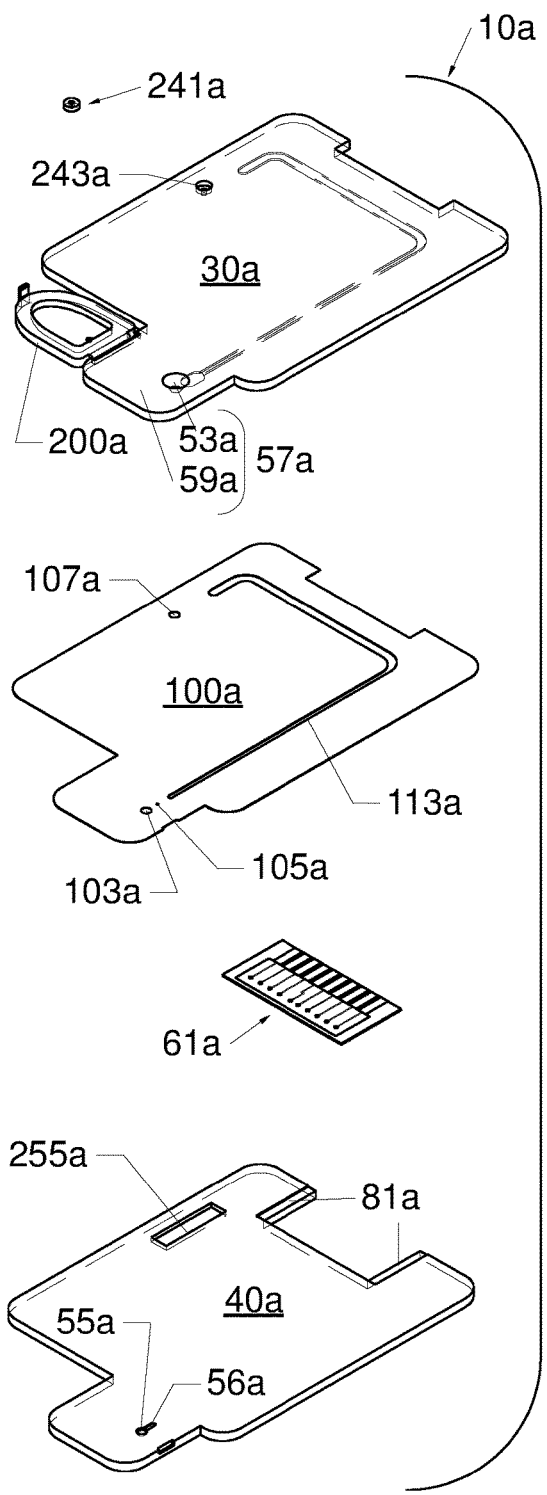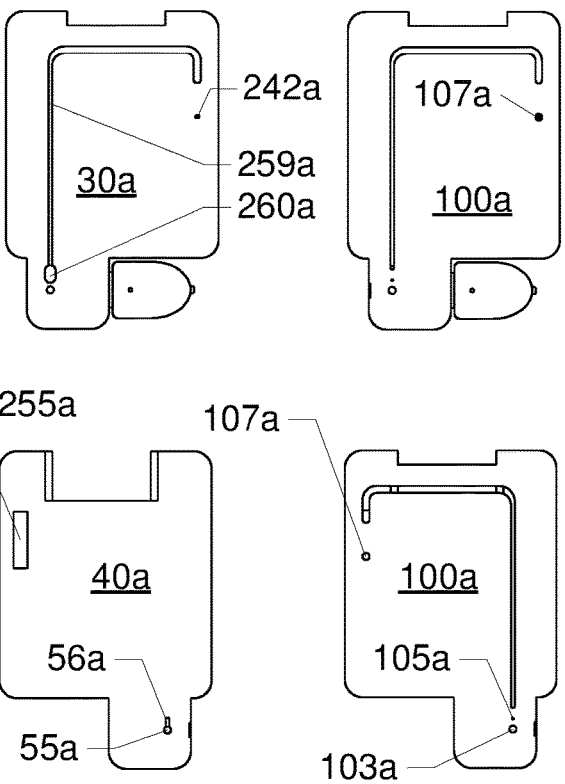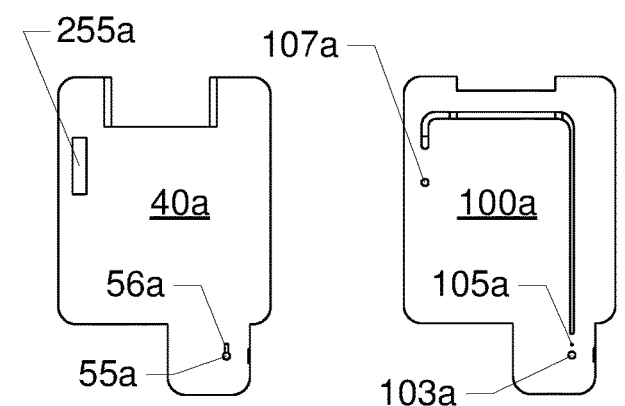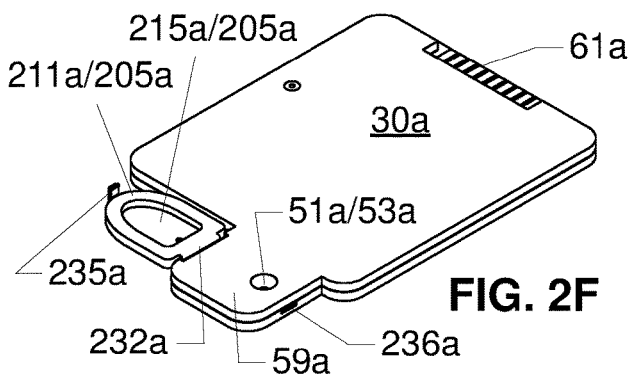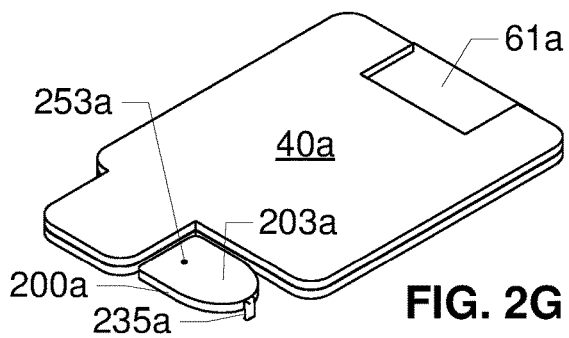

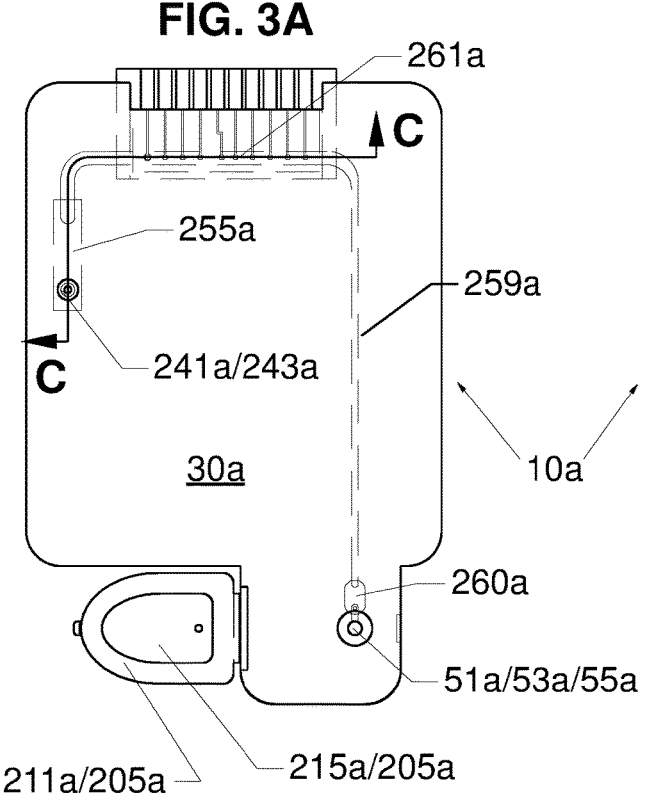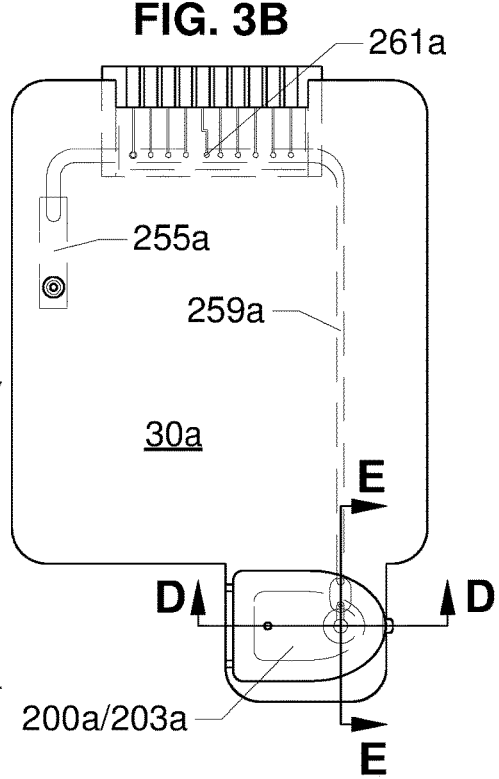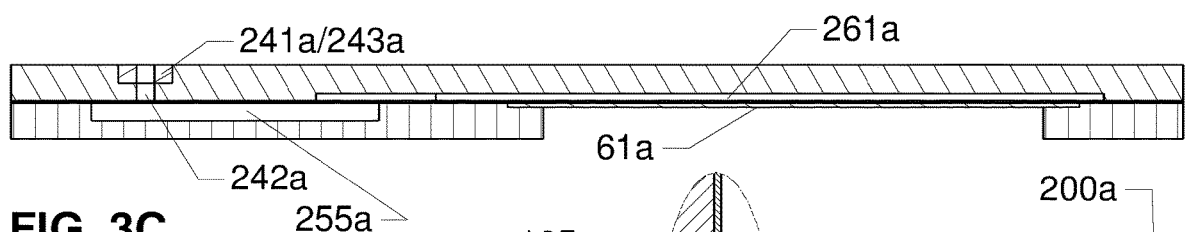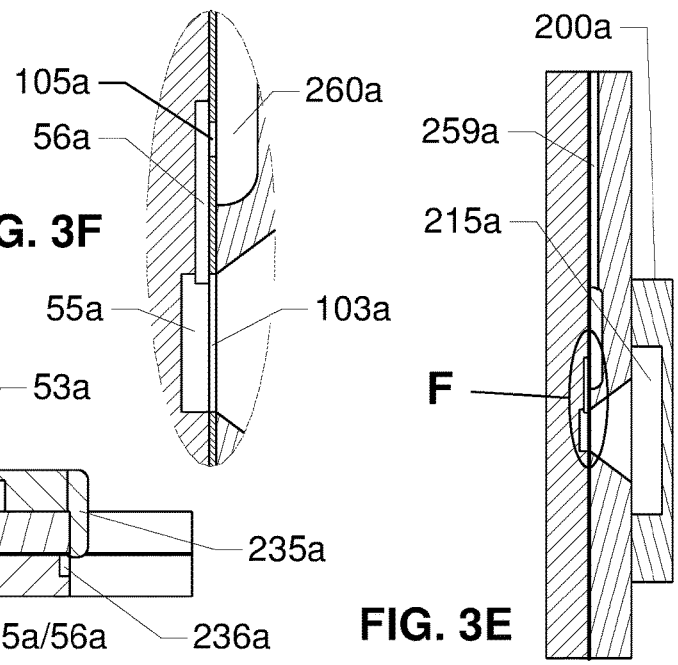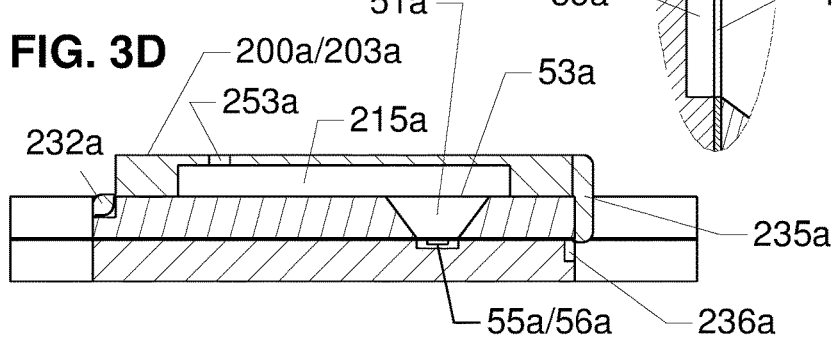

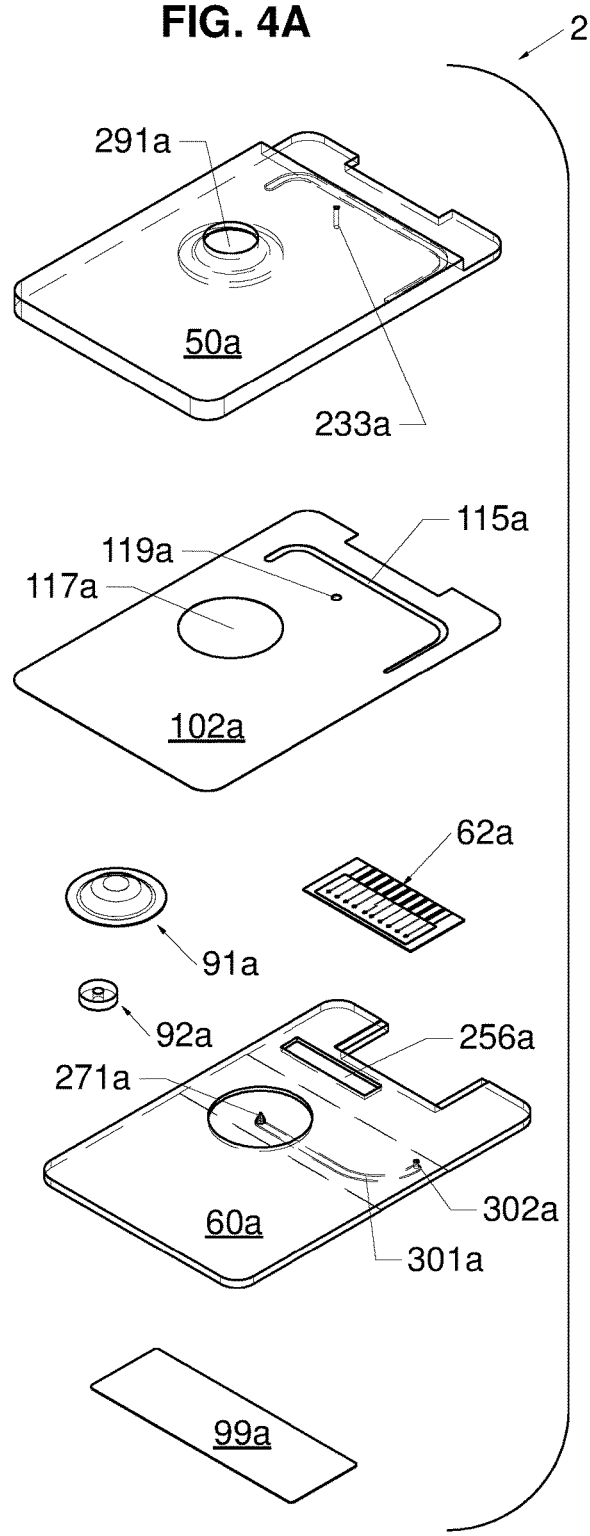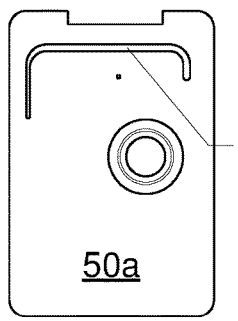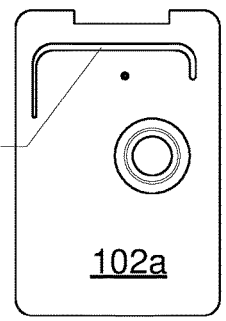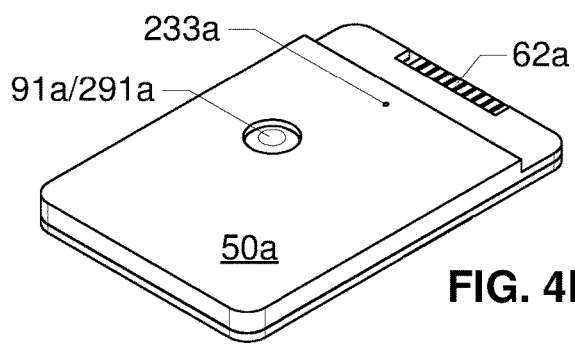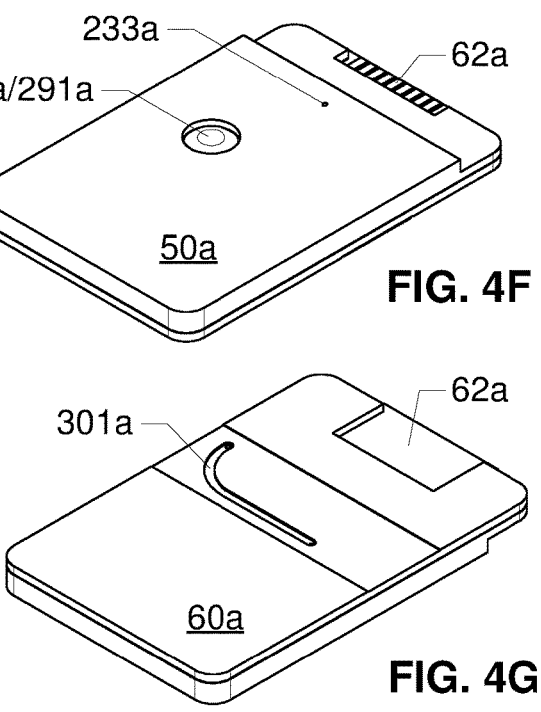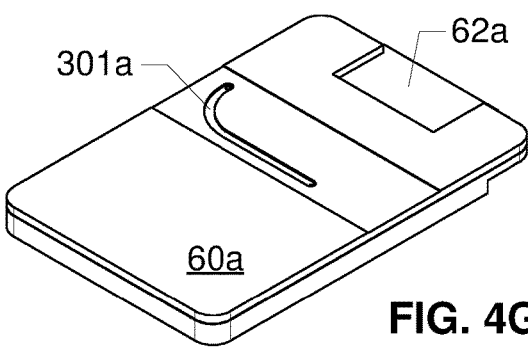

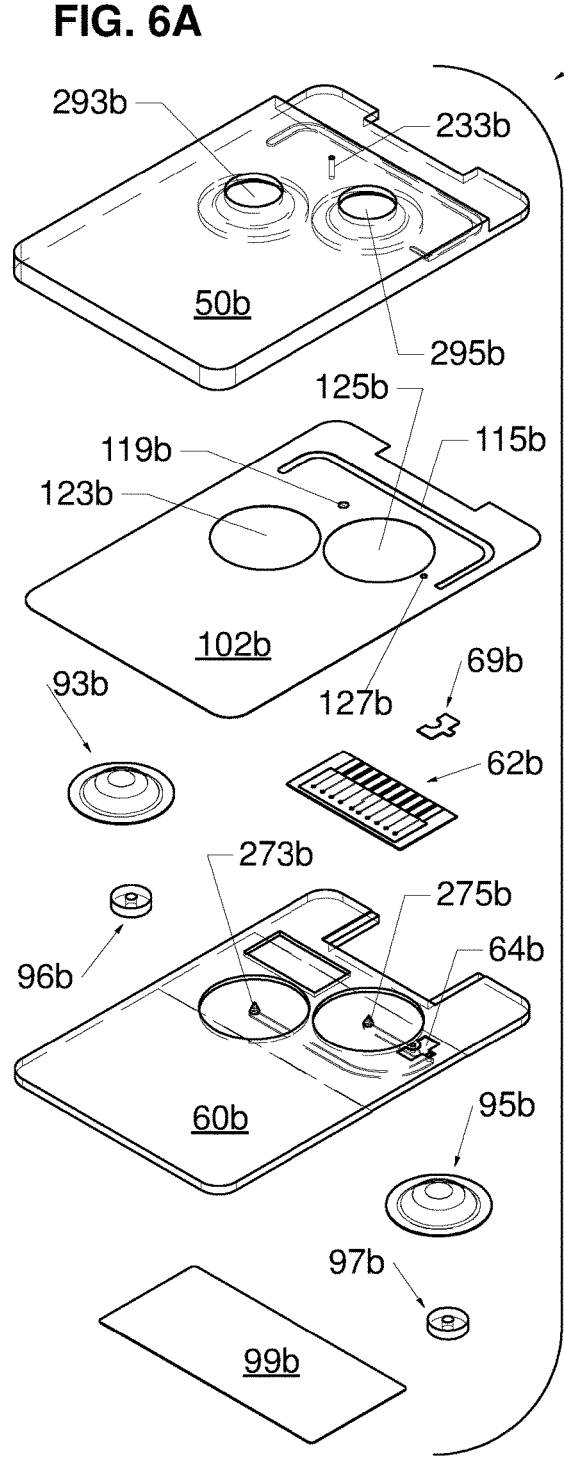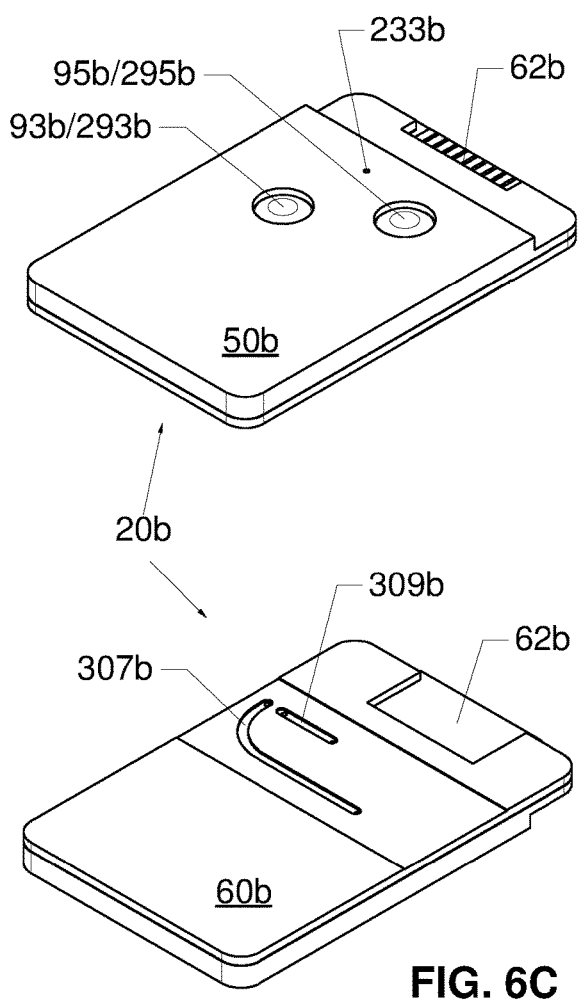

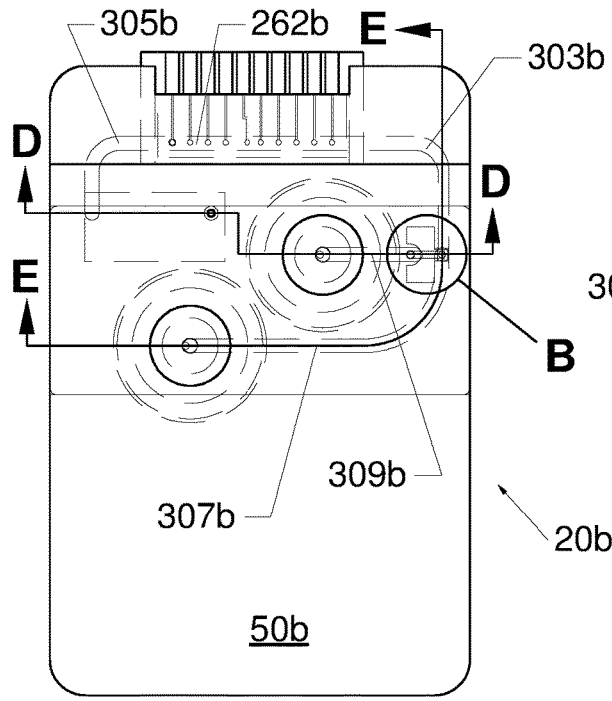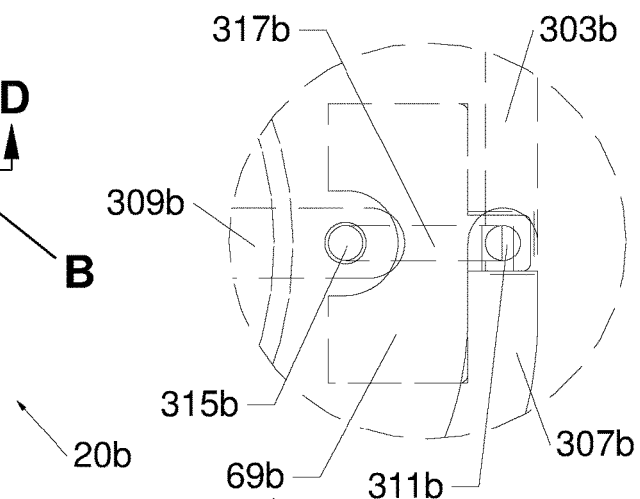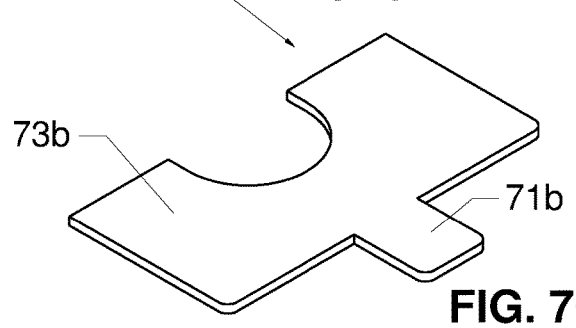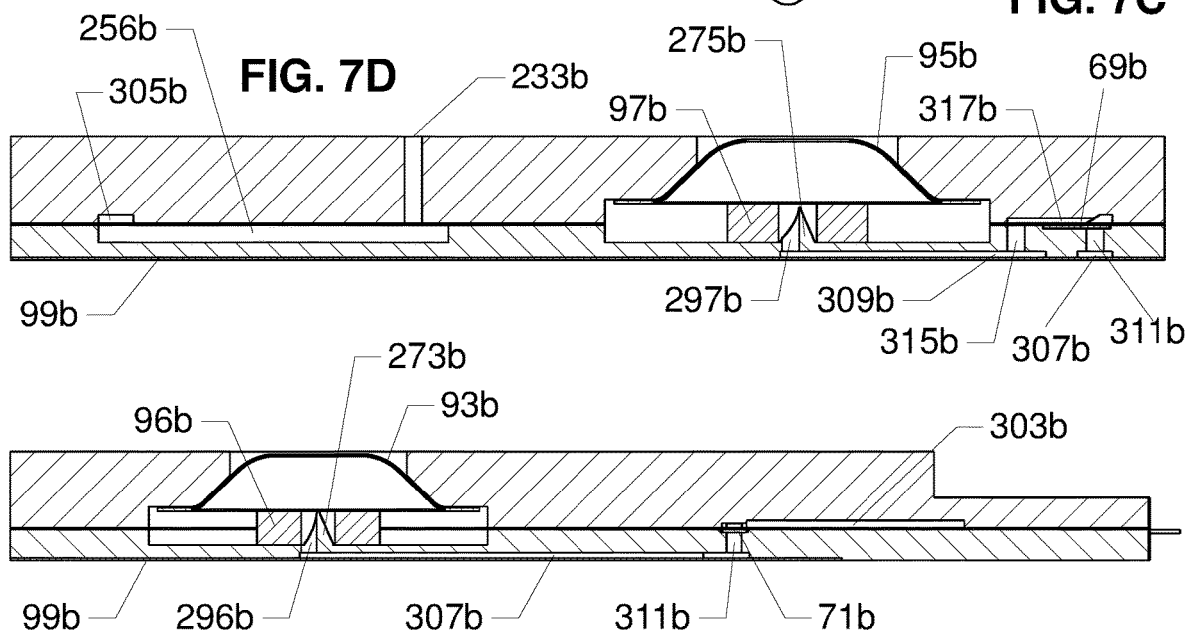

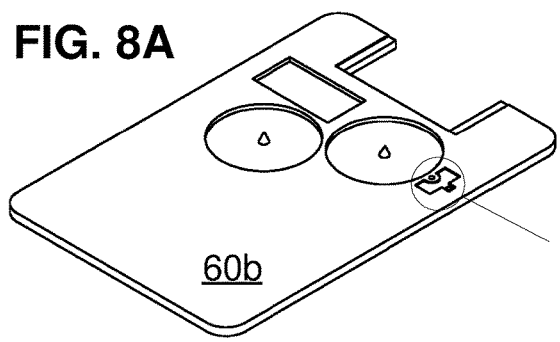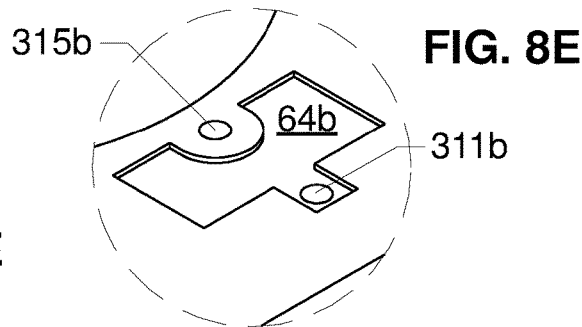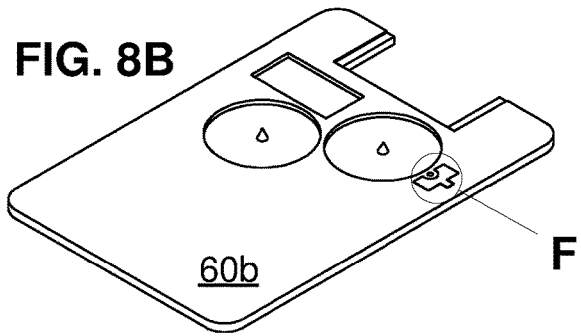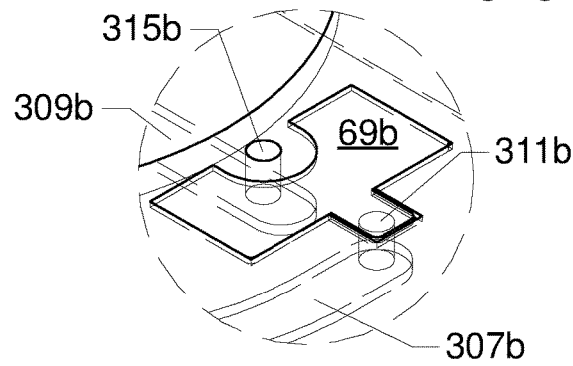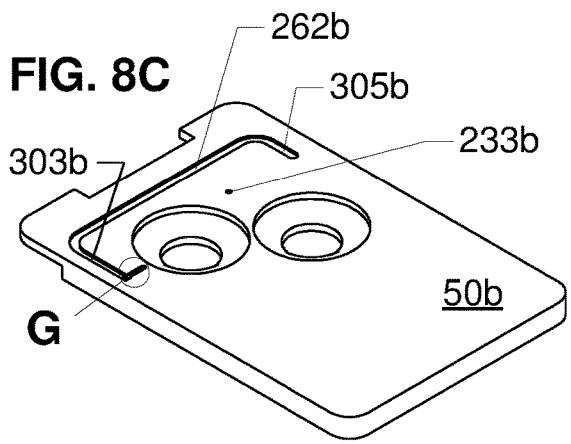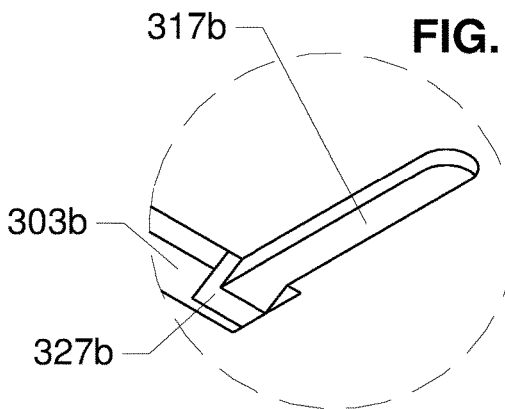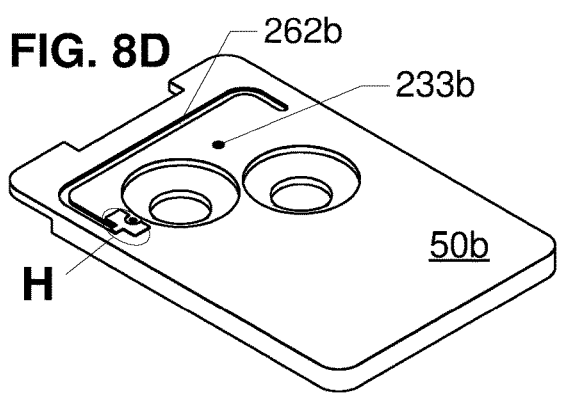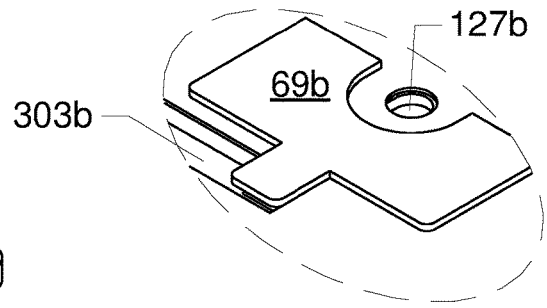

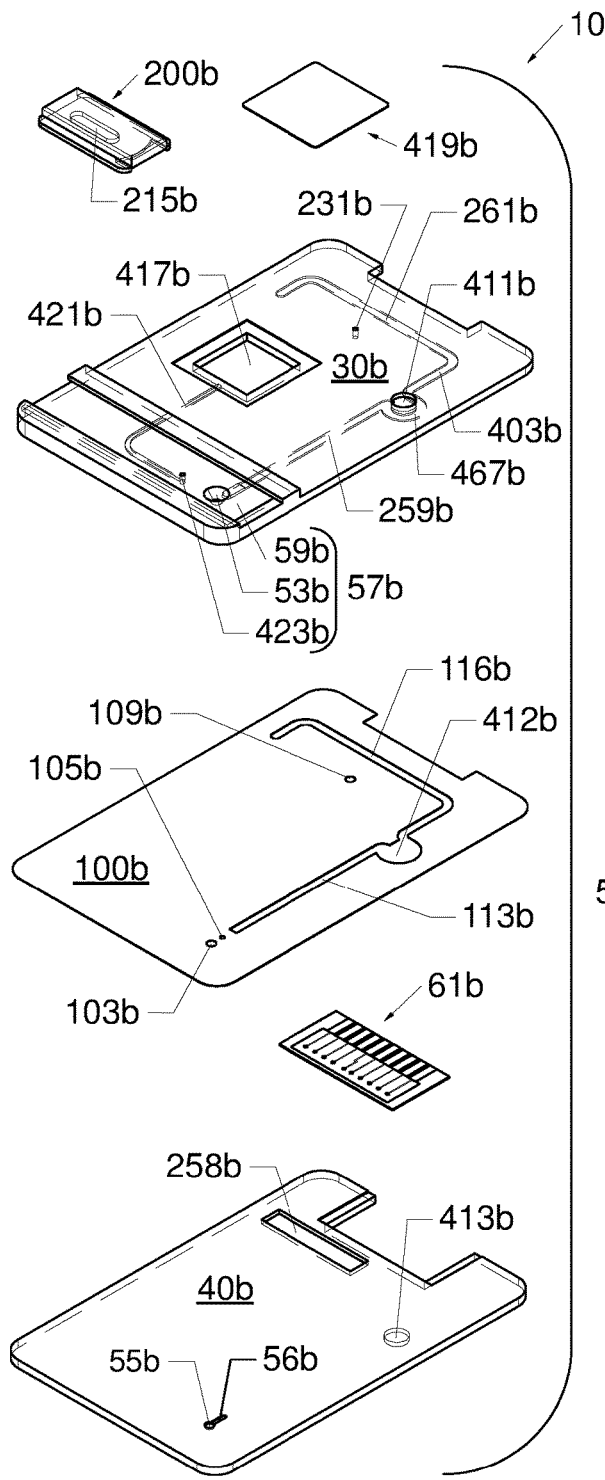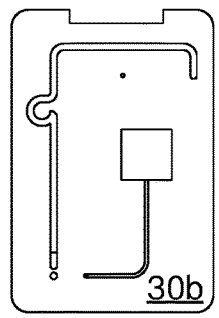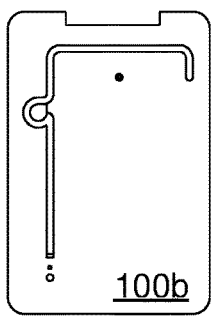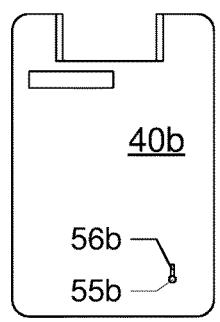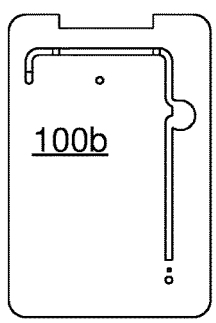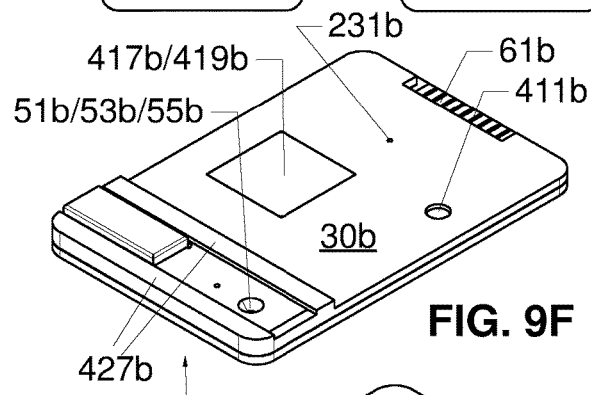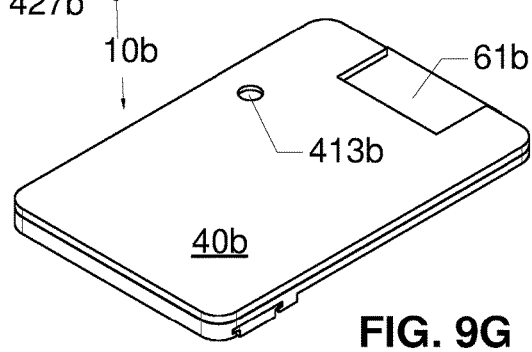

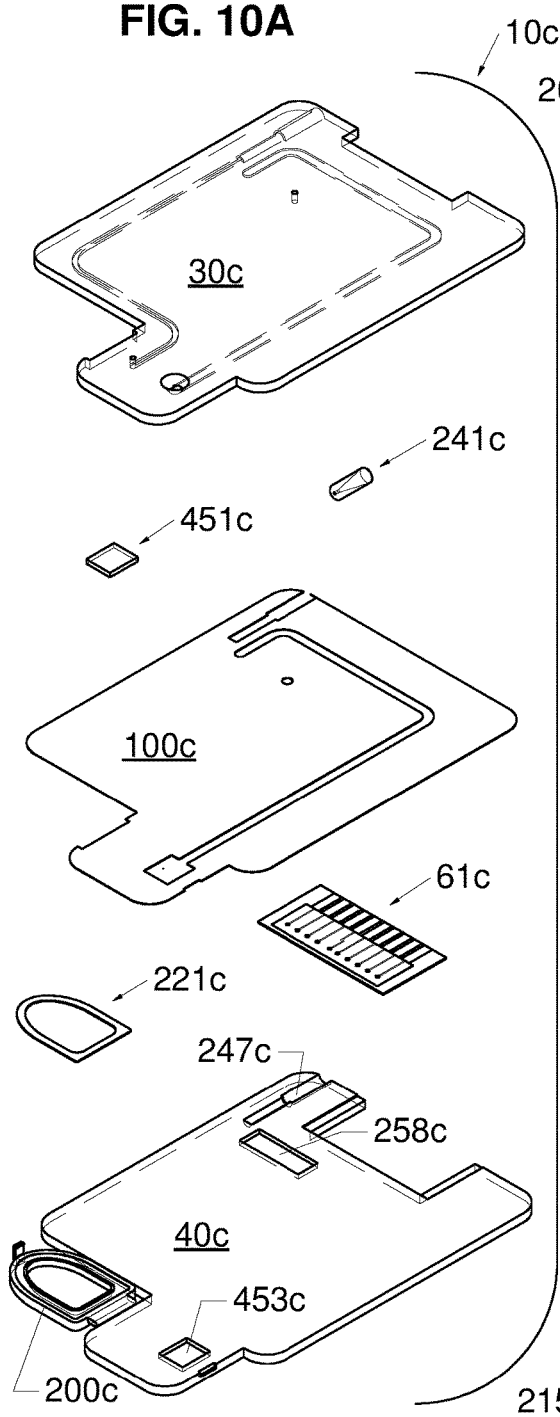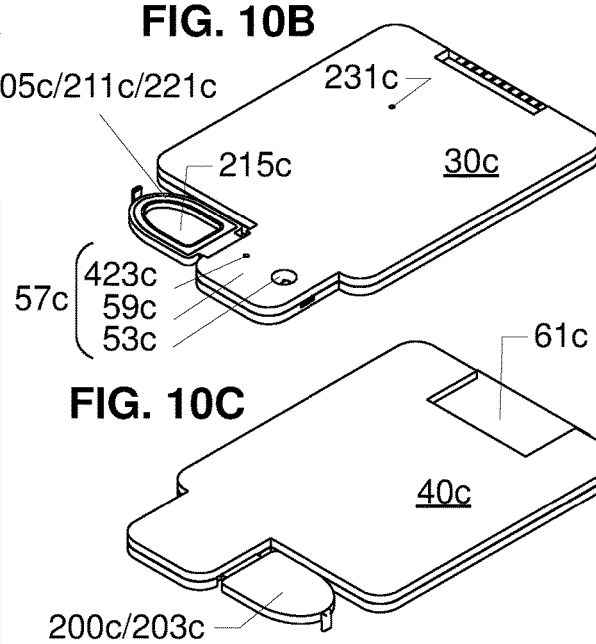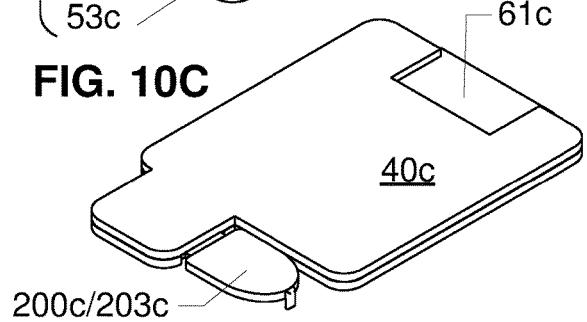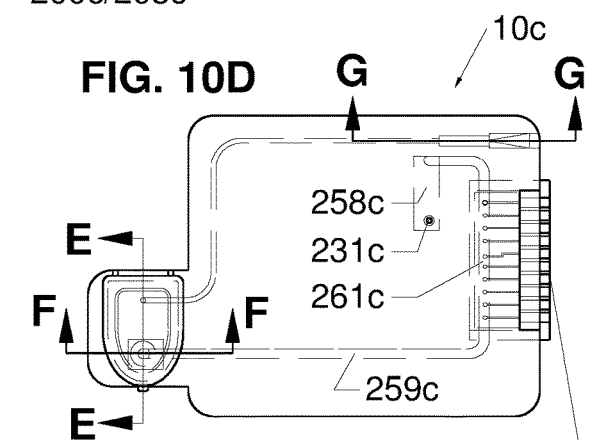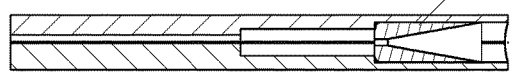

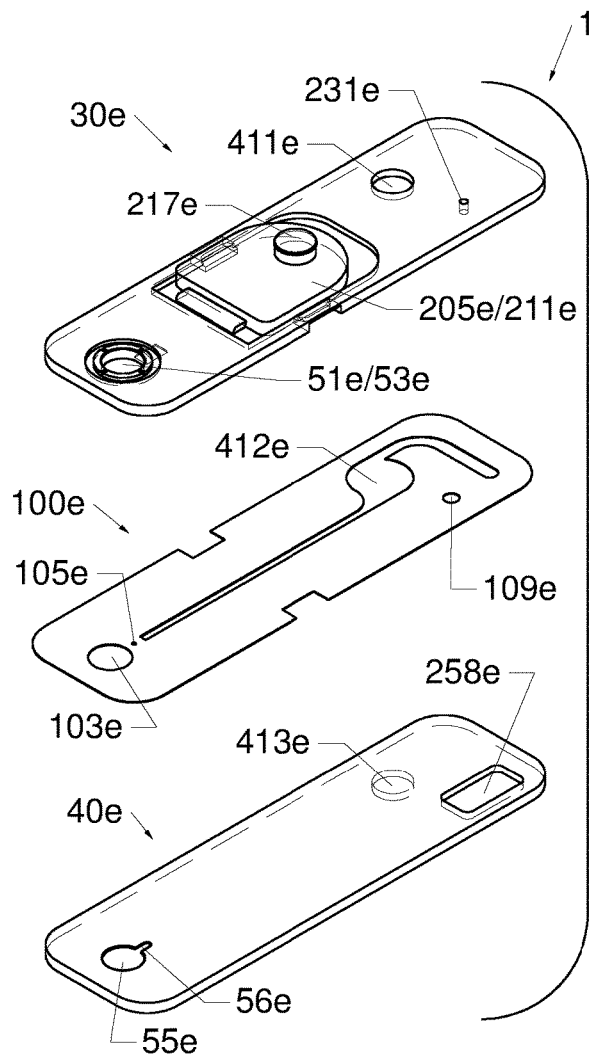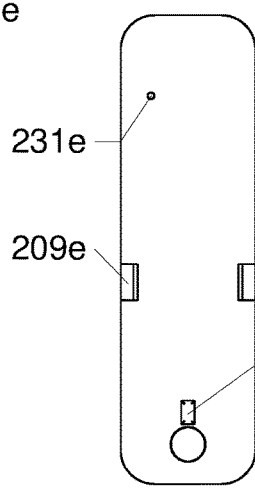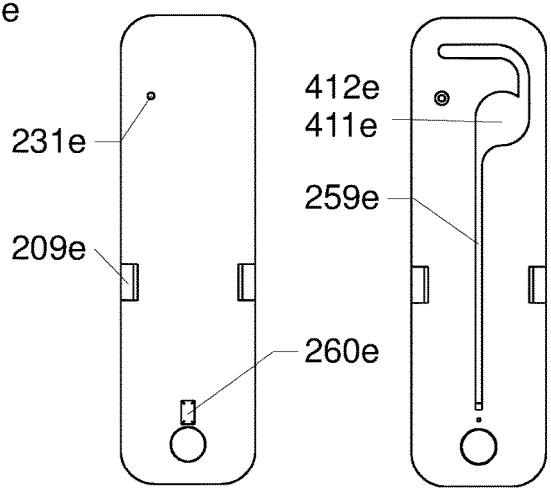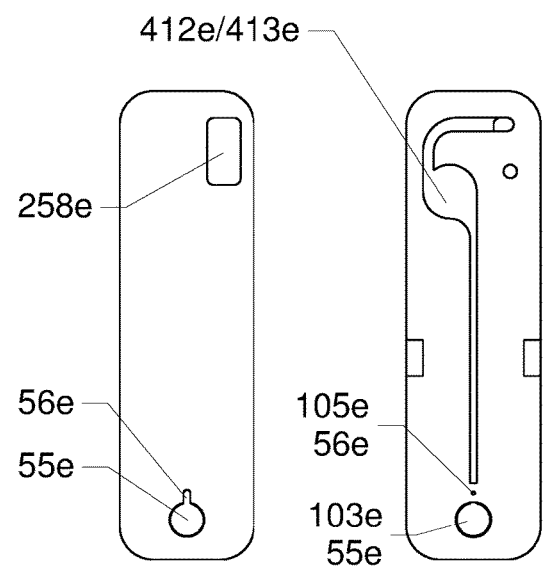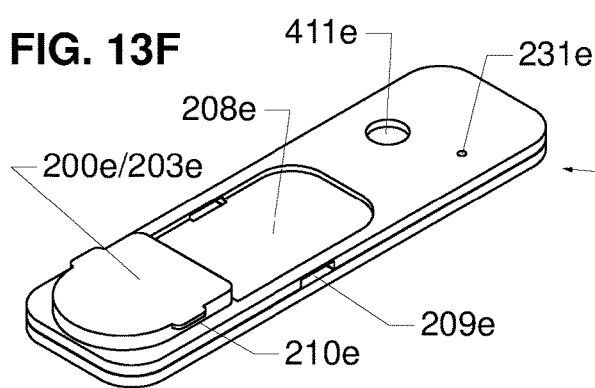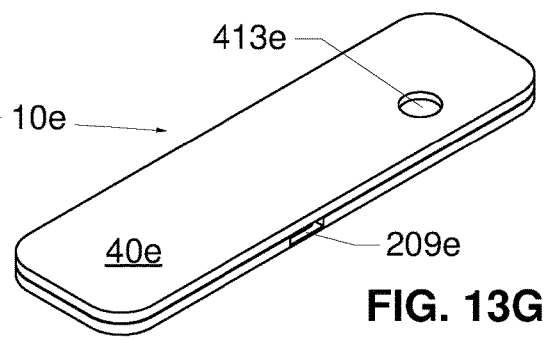

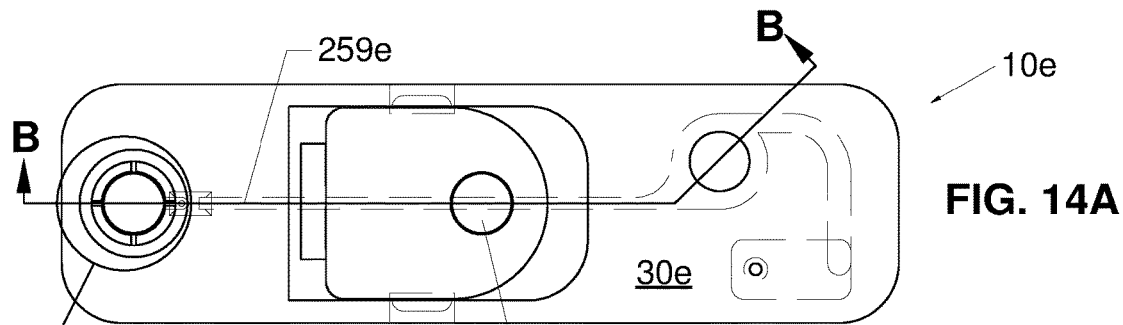
FIG. 14A
FIG. 14B
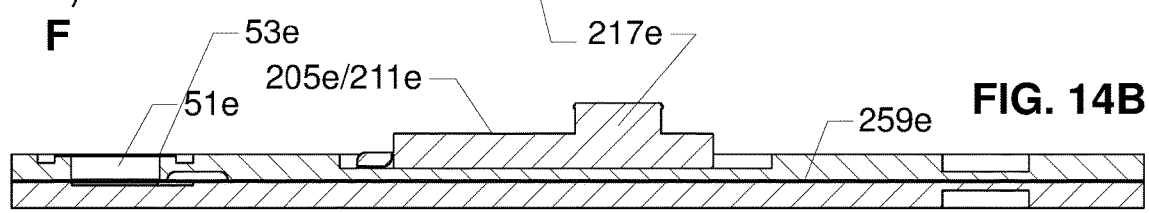
FIG. 14C
FIG. 14D
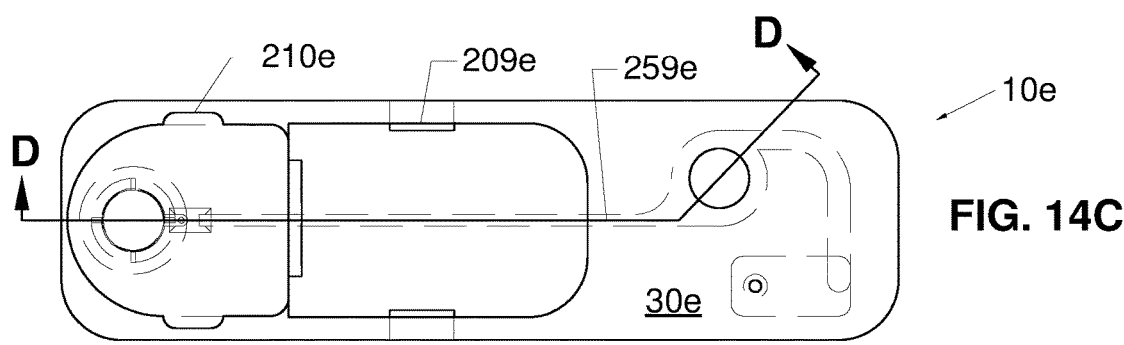
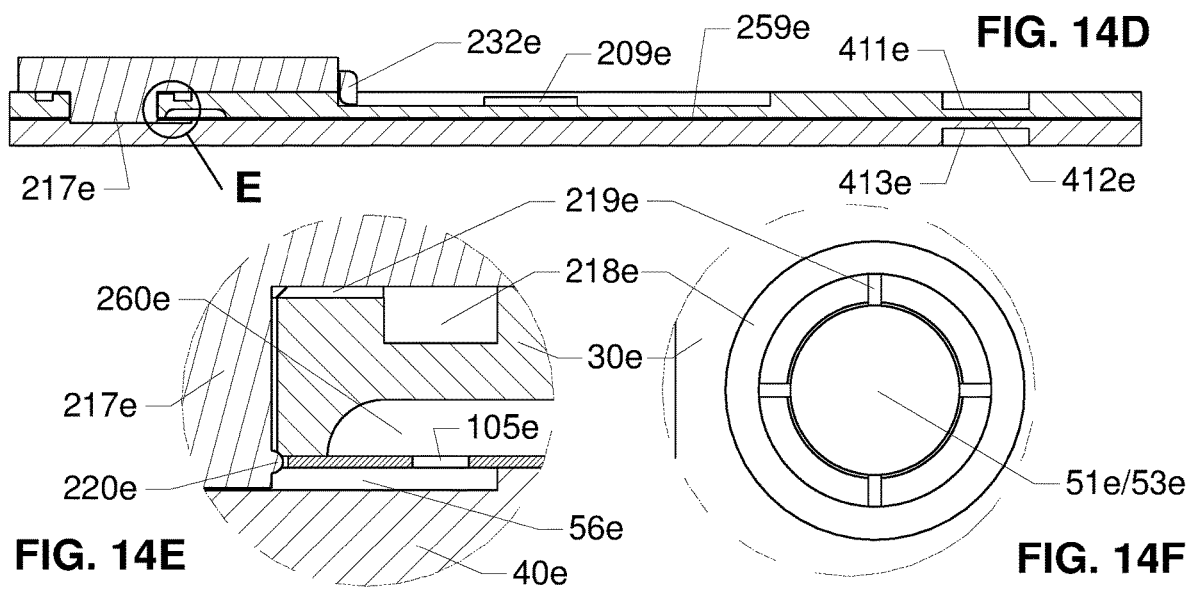
FIG. 14E
FIG. 14F

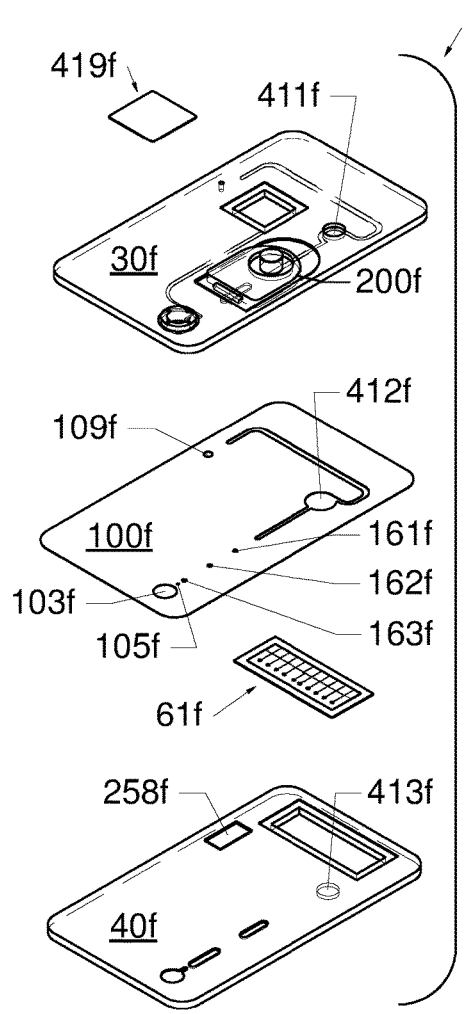
FIG. 16A
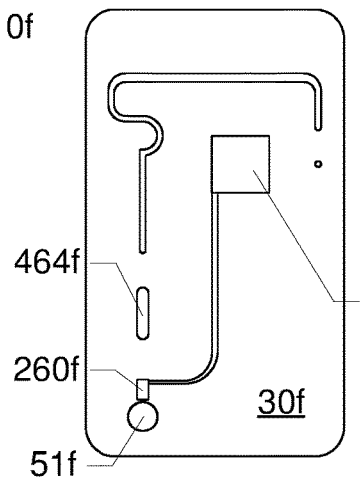
FIG. 16B
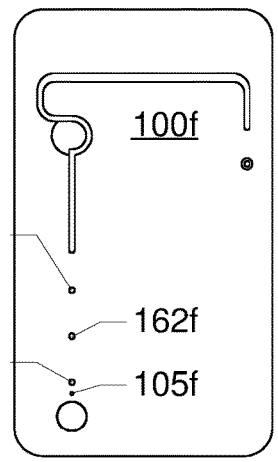
FIG. 16C
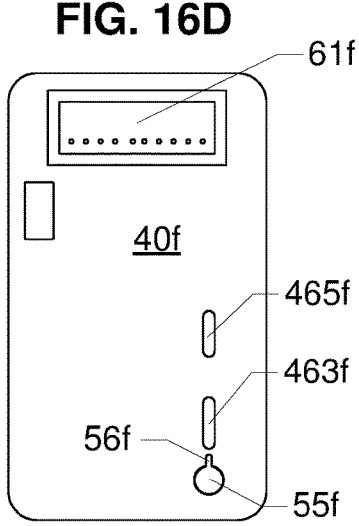
FIG. 16D
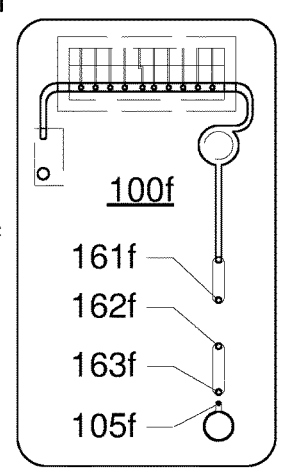
FIG. 16E
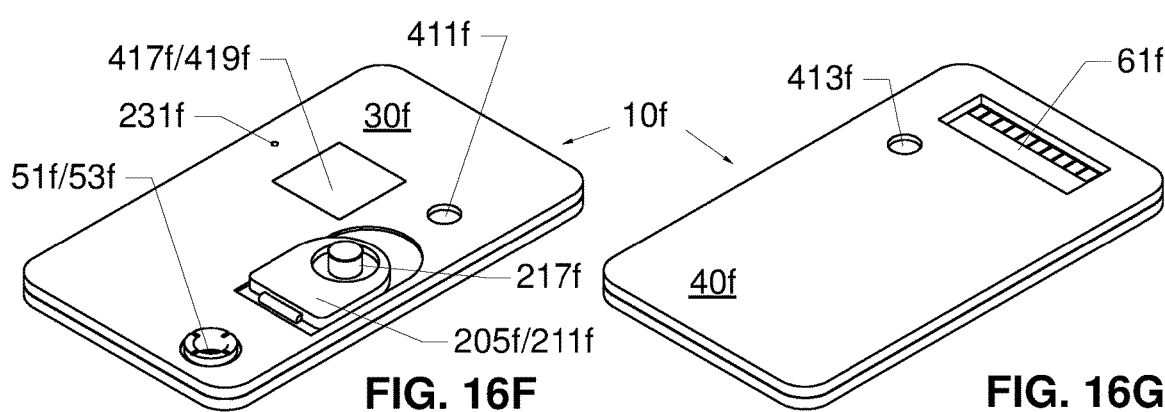
FIG. 16F
FIG. 16G

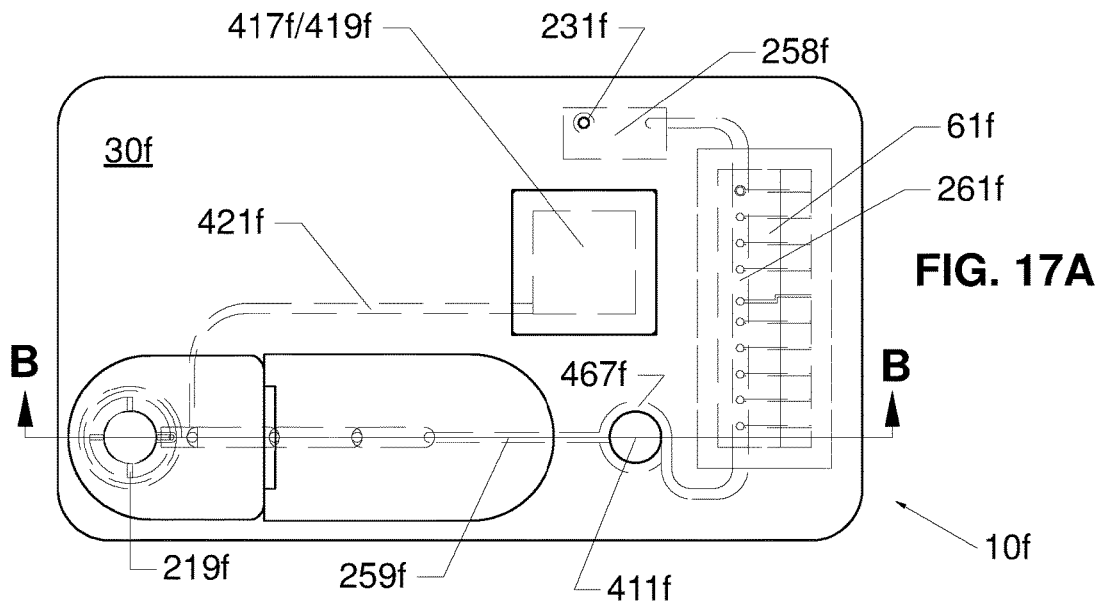
FIG. 17A
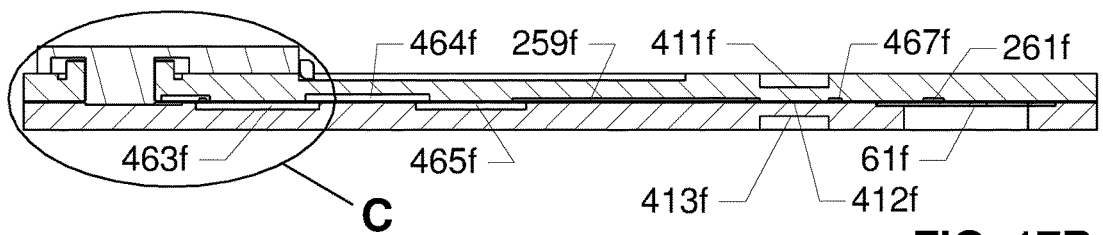
FIG. 17B
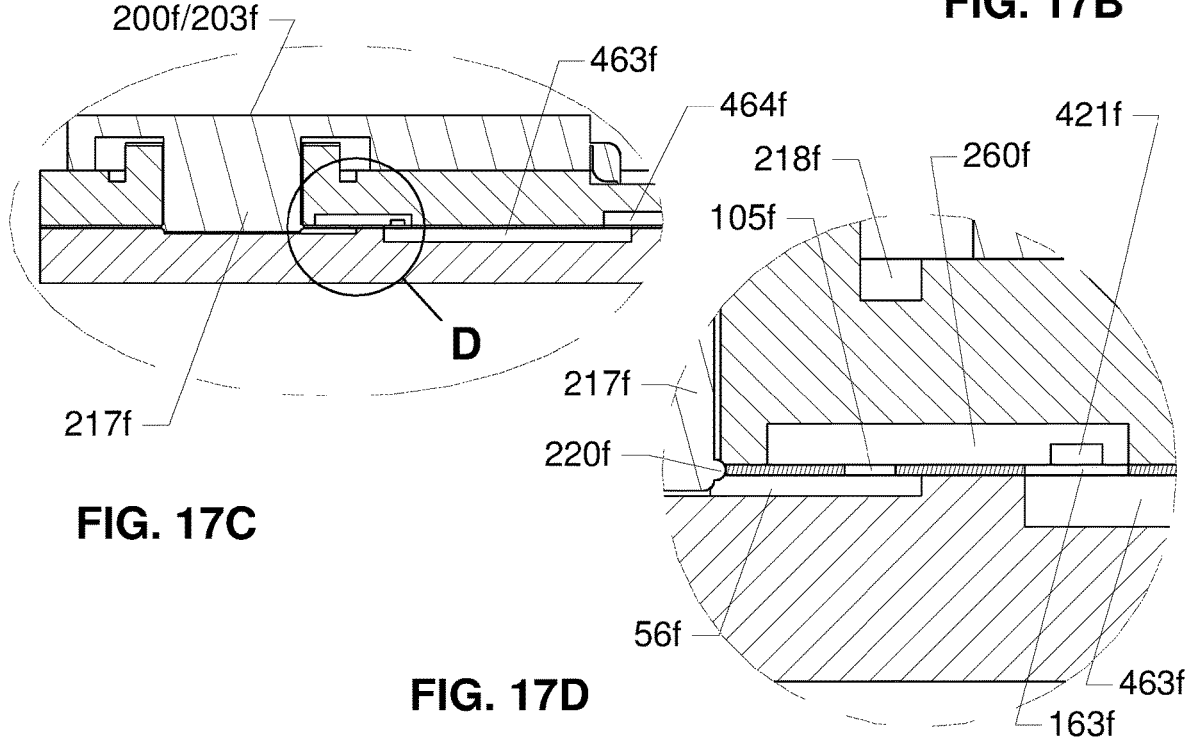
FIG. 17C
FIG. 17D

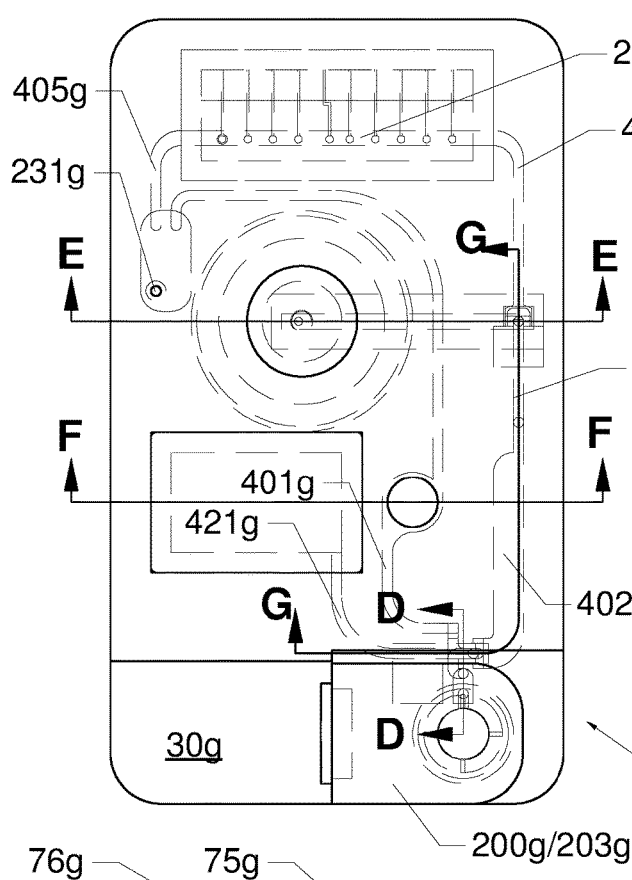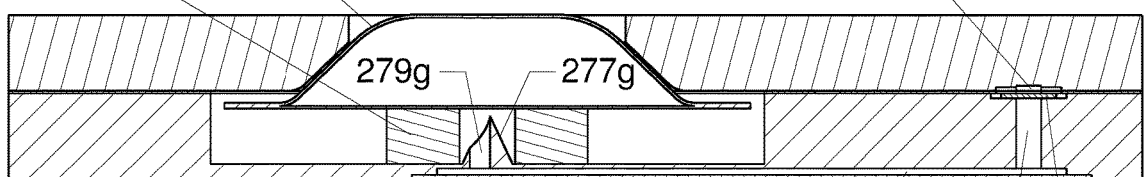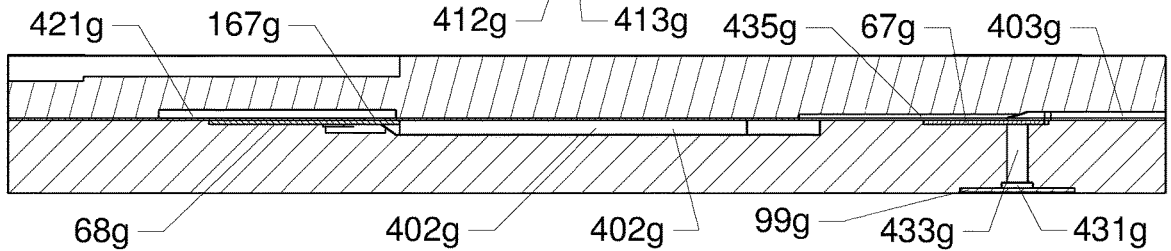

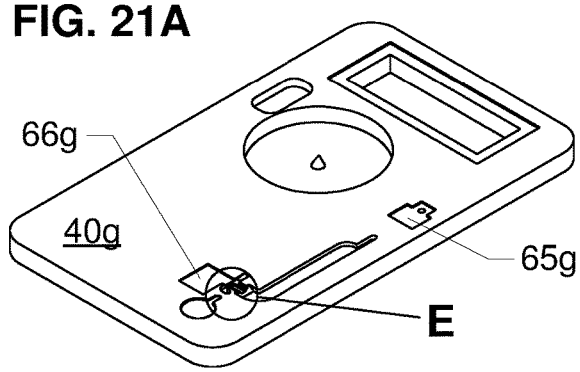
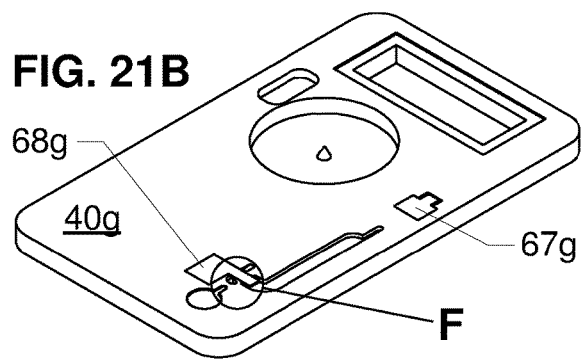
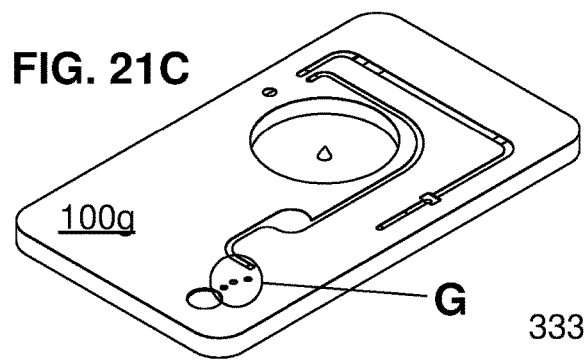
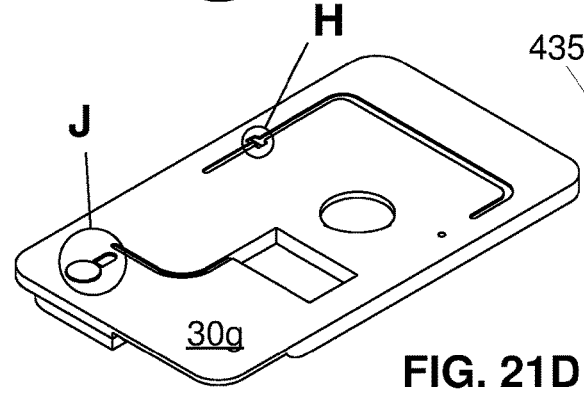
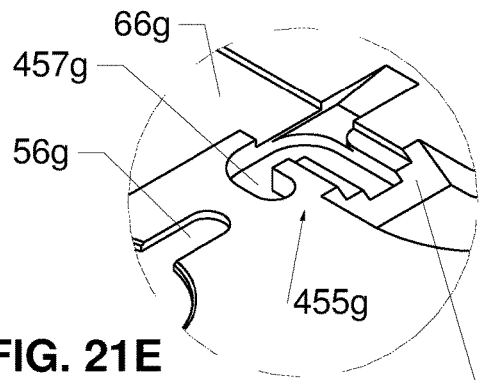
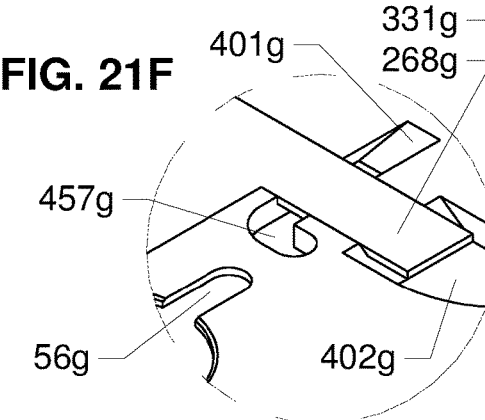
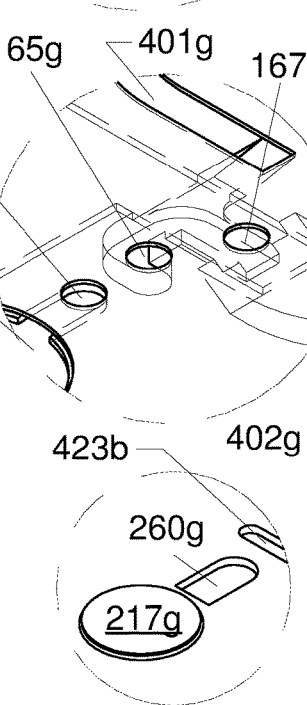

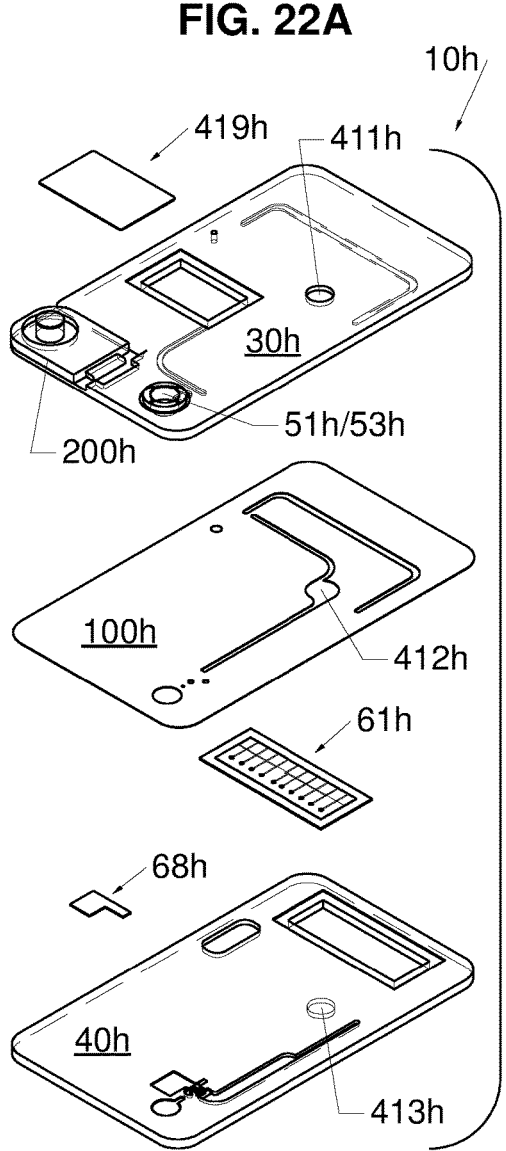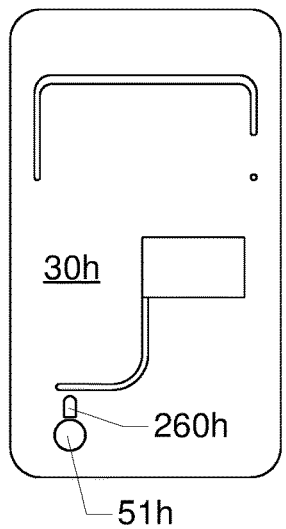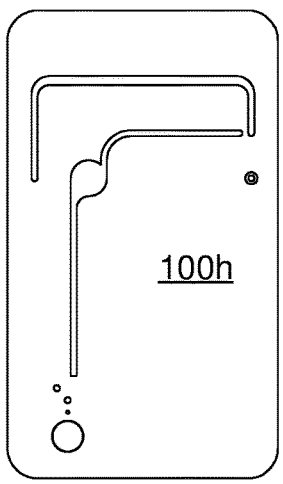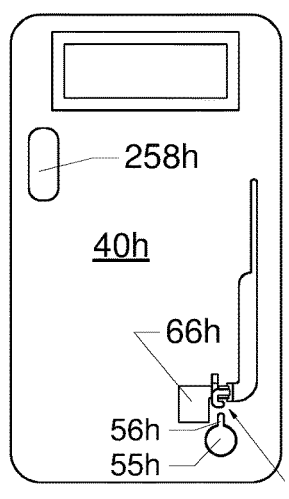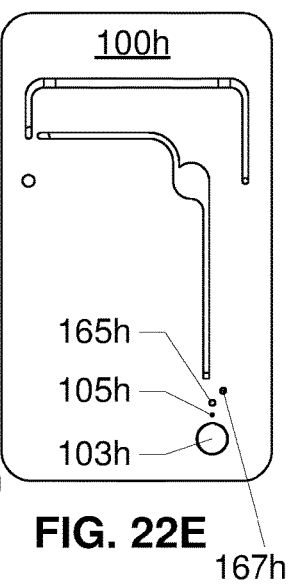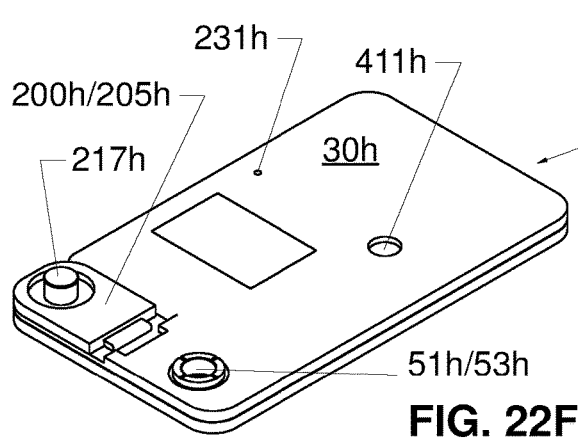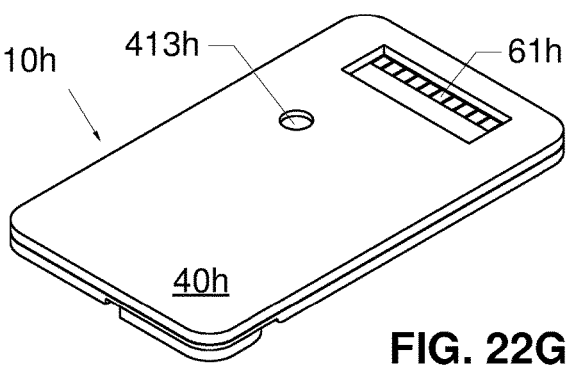

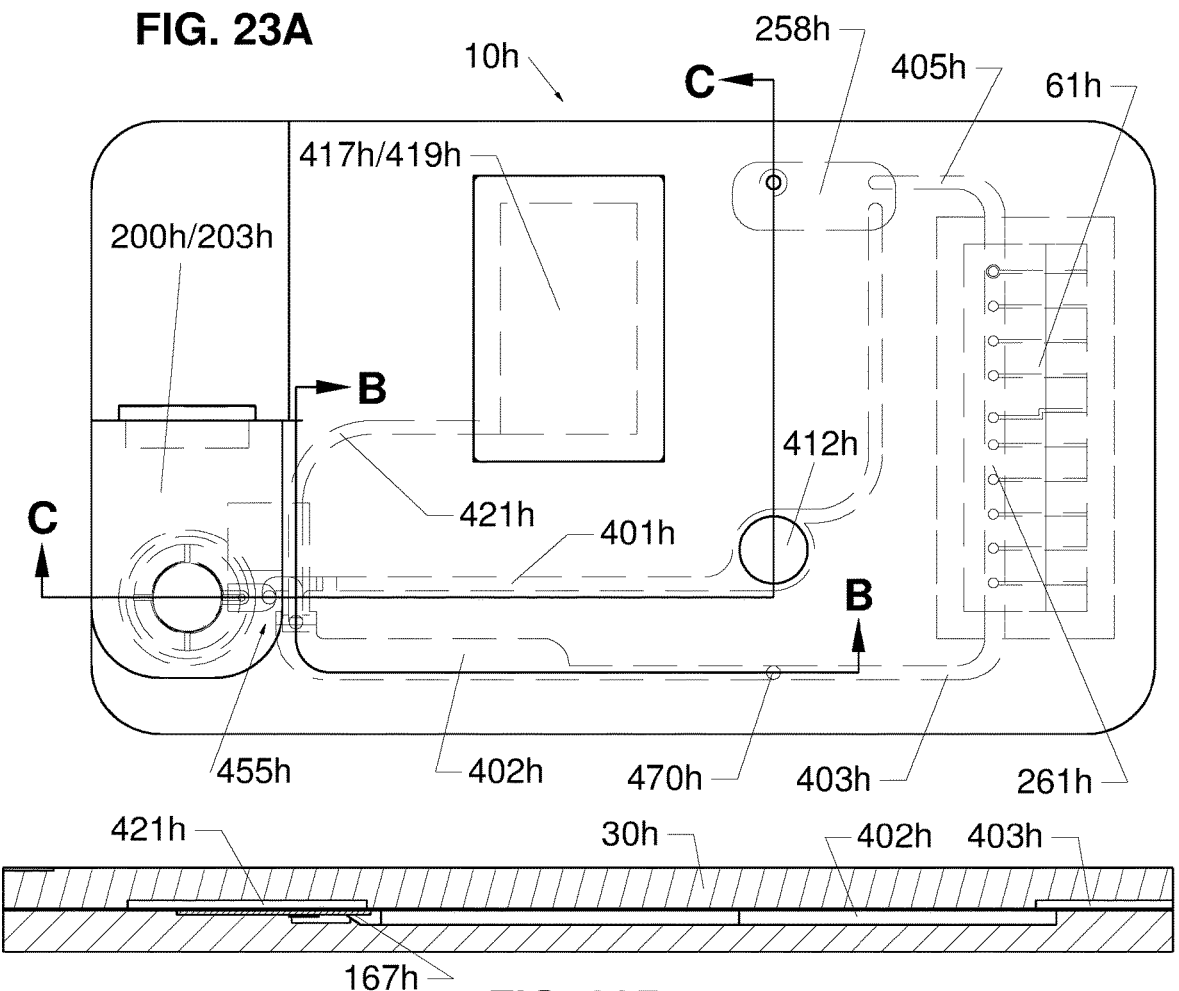
FIG. 23A
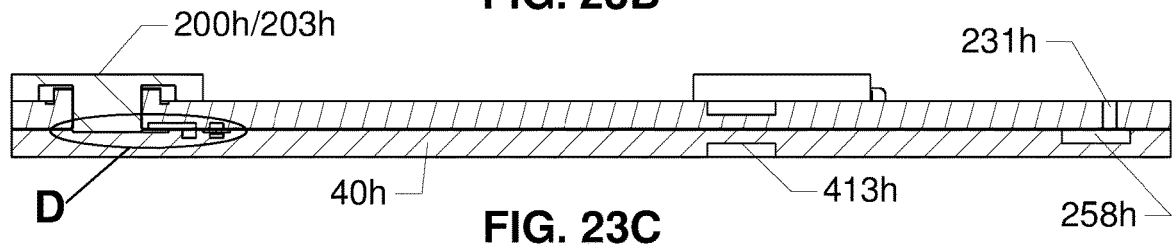
FIG. 23B
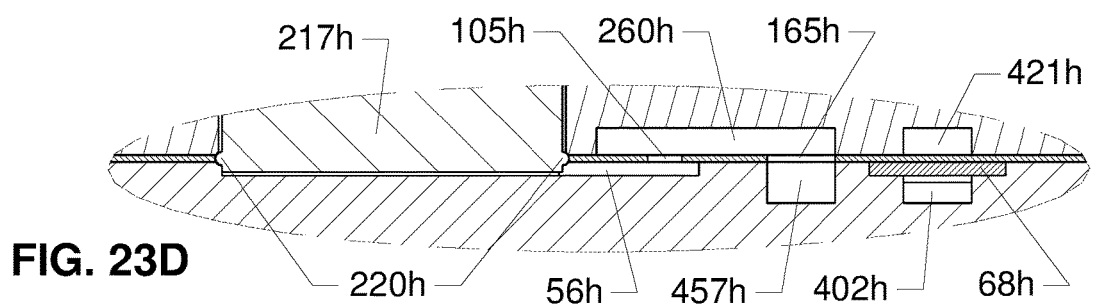
FIG. 23C
FIG. 23D

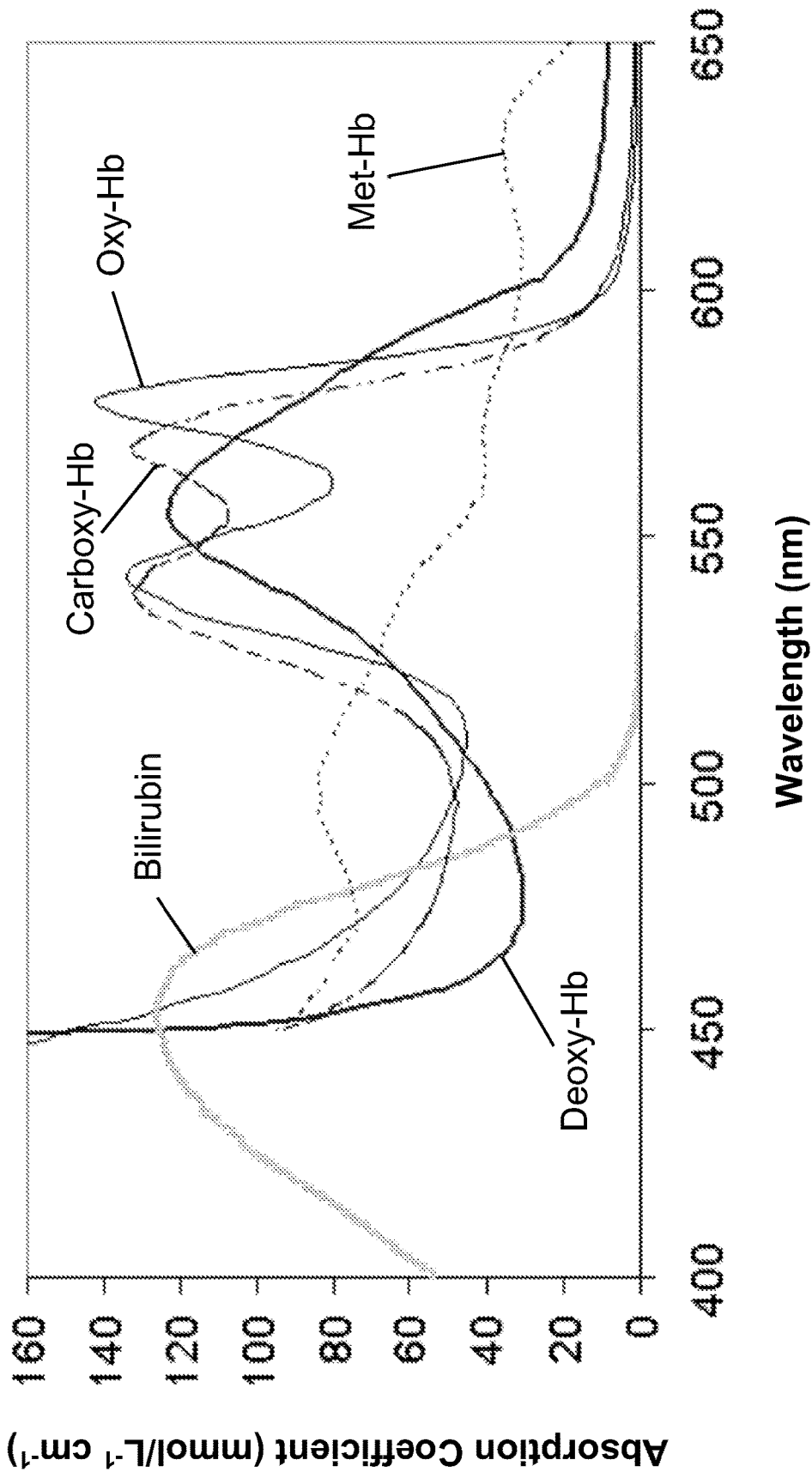
FIG. 29 (Prior Art, from internet link below)
https://www.researchgate.net/publication/7157559_Noninvasive_detection_of_bilirubin_using_pulsatile_absorption

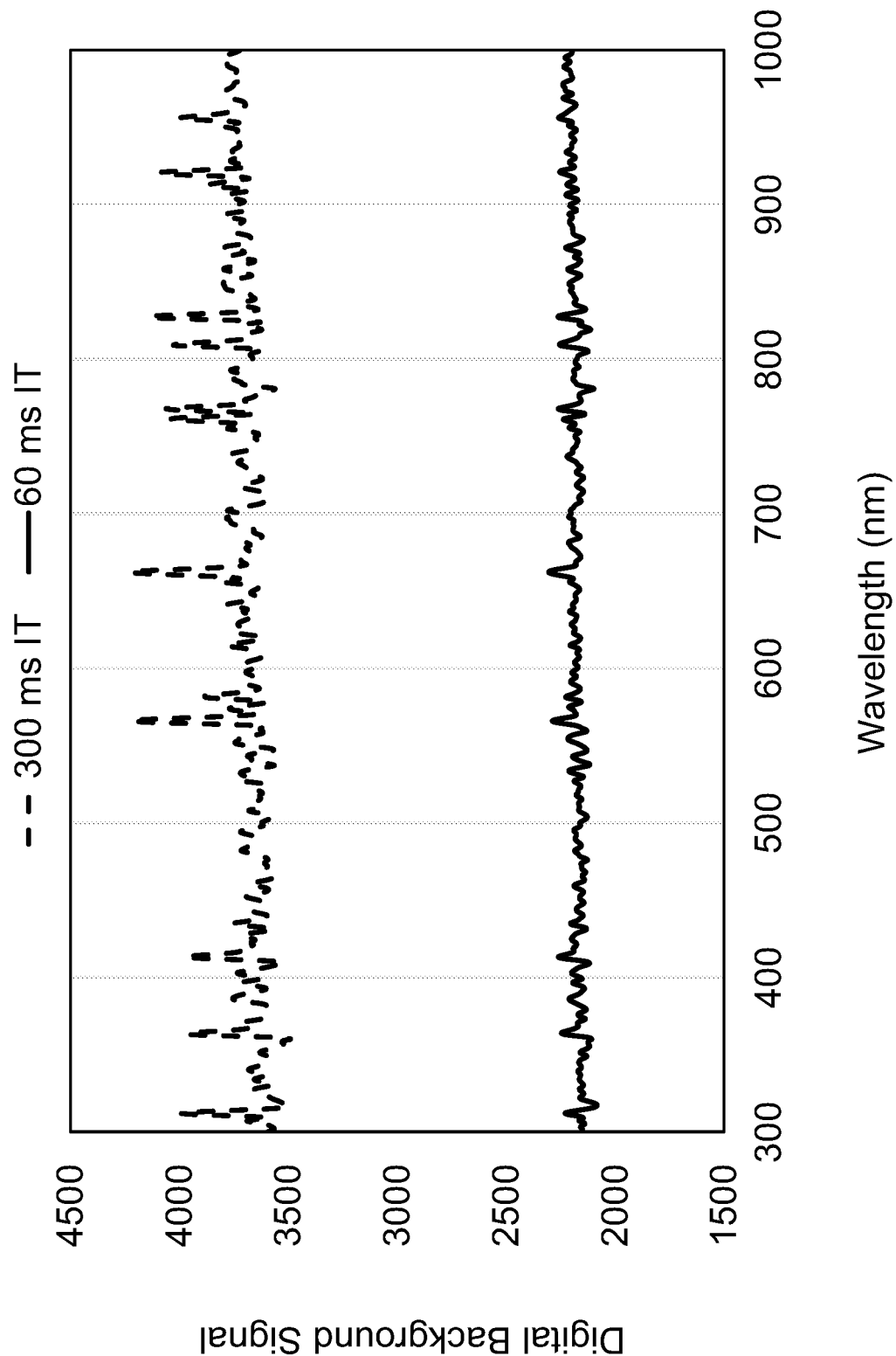

POINT-OF-CARE TESTING SYSTEM, ANALYZER AND METHOD

RELATED APPLICATION

This application claims priority to Canadian Application No. 3,170,696, filed Aug. 17, 2022, the entire contents of which is incorporated herein by reference.

FIELD OF THE INVENTION

The invention relates to a point-of-care testing (POCT) system, analyzer and method for measuring at least a quantity of a first analyte and a quantity of a second analyte in a blood sample. The system comprises an analyzer and a measurement cartridge having one or more detection chambers. The detection chamber of the measurement cartridge may comprise one or more electrochemical sensors and/or one or more optical chambers. The analyzer may comprise one or more sources of electromagnetic radiation (EMR).

BACKGROUND OF THE INVENTION

In the clinical laboratory, a tissue substance from the body that is undergoing analysis is usually referred to as an analyte or a test. "Point-of-care Testing" (POCT) is defined as medical diagnostic testing performed in close proximity to where the patient is receiving care. Point-of-care (POC) is not restricted to laboratory tests but are more common with respect to laboratory tests. POCT is usually performed by non-laboratory personnel and the results are used for clinical decision making. An example of a non-laboratory POC device is a POC ultrasound (POCUS) device.

For the sake of convenience and rapid turnaround time, the tissue or sample of choice for POCT is whole blood (also referred to as blood). Due to the complexity of blood, certain tests can only be performed on serum or plasma. Regardless of whether the sample is serum, plasma or whole blood, the quantities of analytes measured are usually measured in the plasma component of whole blood and are usually reported as a mass or molar quantity per unit volume of the whole blood used for analysis. Sometimes it is preferred to lyse the red blood cells before measurement, whereby the contents of the red blood cells become mixed with the plasma. Because the actual volume of plasma present in the blood depends on the hematocrit, some systems attempt to correct the measured values to account for hematocrit. The hematocrit is the proportion, by volume, of the blood that consists of red blood cells.

When blood is allowed to clot and the sample is centrifuged, the yellow liquid that sits on top of the blood clot is called serum. If the blood is collected in a tube containing an anticoagulant, for example heparin, and the blood centrifuged, the cells and cell fragments, referred to as formed elements, are separated from a yellow liquid called plasma, which sits on top of the formed elements. The plasma is usually about 90 percent water, in which the formed elements are usually suspended, and it transports nutrients as well as wastes throughout the body. Various analytes are dissolved in the plasma for example, glucose, electrolytes, blood gases, drugs, hormones, lipids, enzymes (e.g., ALT, which may be used for assessing liver function), and metabolites (e.g., creatinine which may be used for assessing kidney function), and lactate which may be used for detecting sepsis.

POCT involves a range of procedures of varying complexity that may include manual procedures and automated procedures conducted by portable analyzers. POCT is most efficient when the sample of interest can be applied to or loaded onto a measurement cartridge or a test cartridge at a cartridge opening (may also be referred to as a sample inlet of the cartridge), capped, and the analytical or testing steps performed automatically after the capped cartridge is inserted into a slot or receptor of an associated analyzer. Some POCT require one or more reagent that reacts with the blood sample, providing altered blood. The result of reaction between a liquid sample and one or more reagents may depend on the quantity of the one or more reagent and the volume of liquid sample. The reagent is preferably in a dry form, in order to avoid dilution of the sample.

Some blood tests, for example coagulation assays and immunoassays, require a fixed volume of sample or metered volume of sample to ensure that when mixed with a reagent, the ratio of the volume of sample to the volume (or mass) of the reagent is held constant. The term metered blood means that the blood is supplied in a measured or regulated amount. In other cases, for example the measurement of blood gases and electrolytes, a metered volume of sample is not required. In the case of electrolytes, the volume of the sample is usually not an issue if the electrolyte concentration is estimated by measuring electrical activity in the sample. The term blood gases may refer to pH, $pCO_2$ (partial pressure of carbon dioxide) and $pO_2$ (partial pressure of oxygen) and the term electrolytes may refer to sodium, potassium, chloride, and bicarbonate ions. Other ions like calcium ions may also be referred to as electrolytes. Electrical activity is usually measured using electrochemical sensors, also referred to as biosensors. Blood gases and electrolytes are mostly measured by electrochemical sensors, but optical measurements are also possible.

There are other tests that do not require a fixed volume of sample, and cannot be measured using biosensors, for example CO-oximetry. CO-oximetry is a spectroscopic or optical technique that is used to measure the amount of different Hemoglobin (Hb) species present in a blood sample, for example, Oxy-Hb, Deoxy-Hb, Met-Hb, Carboxy-Hb and Total-Hb, and their measurements are used to assess the oxygenation and anemic status of a patient. It should be noted that although Total-Hb is a collection of the other species of Hb, Total-Hb is also referred to as a Hb species. Total bilirubin, which comprises mostly conjugated and unconjugated bilirubin, is also referred to as a bilirubin species. Met-Hb and Carboxy-Hb are non-functional hemoglobin and elevated levels can be life-threatening. Although electrolytes and CO-oximetry measurements do not usually require fixed volumes of blood, the distance the blood sample travels along microfluidic channels inside some cartridges may need to be controlled or metered.

Hemoglobin is an example of an analyte that is not present in the plasma unless hemolysis has occurred. Hemoglobin is usually present in red blood cells (RBCs), and the mass or molar concentration of hemoglobin may be measured in altered blood (may be simply hemolyzed blood) or unaltered blood. Hemolyzed blood may be produced using sound waves or chemicals, for example sodium deoxycholate. Some analyzers measure hematocrit by electrical conductivity and convert the hematocrit measurement to a total hemoglobin concentration, and some analyzers measure total hemoglobin concentration by spectroscopy, and convert the total hemoglobin concentration to a hematocrit value. Spectroscopic calibration algorithms or equations may be developed to measure both hematocrit and total hemoglobin concentration.

Another analyte that resides inside red blood cells is folic acid (~50% localized in red blood cells, the rest is stored mostly in the liver), and the measurement of RBC folate provides useful diagnostic information. Potassium is another analyte that resides in the RBCs, at about 20 times the concentration in plasma. However, measurement of RBC potassium provides no diagnostic value, whereas plasma potassium is a commonly ordered analyte for aiding in assessing acid-base-electrolyte balance.

Applying an unmetered sample volume to test strips is well known; some test strips contain absorbing sections that can accommodate a known volume of plasma, after the RBCs are retained in another section of the test strip near the blood application site. In some cases, the hematocrit affects the plasma flow in test strips, and therefore correction for hematocrit may improve accuracy of the analyte measurement. A common analyte that is measured using a test strip is blood glucose, and glucose test strips play a major role in managing diabetes.

POCT has improved patient care in several areas including the Emergency Department (ED) and Intensive Care Units (ICU) of hospitals, but the ED and ICU are usually very busy and may have space limitations for implementing more than one POCT analyzer. In addition to having accurate and reliable POCT in the ED, ICU, and for use by first responders, user friendliness is a major issue.

POCT analyzers are usually pre-calibrated, with calibration information installed in a barcoded label on the test strip or test cartridge or installed in the analyzer associated non-transient computer-readable memory. Examples of prior art are provided below in order to discuss some calibration issues. Spectroscopic calibration, for example calibration used for CO-oximetry, are more complex. One or more calibrators (or calibration standards with known amounts of one or more analytes) may be used to calibrate a system. In the simplest cases of calibration, one or two calibrators are required. Commonly used calibration equations usually define a straight line, with signal response on the X-axis and concentration of analyte on the Y-axis. A straight line is usually defined by a slope and a Y-intercept (also referred to as an offset). Calibration adjustment for slope may be performed using two calibrators, and calibration adjustment for offset may be performed using one calibrator, referring to two-point and one-point calibration, respectively.

Application of spectroscopic technology in POCT can be improved by expanding the wavelength range of spectral measurements. More analytes may be measured simultaneously if the wavelengths include portions of the ultraviolet (UV) spectrum, the visible (VIS) spectrum, and portions of the near infrared (NIR) spectrum.

SUMMARY OF THE INVENTION

The invention relates to point-of-care testing (POCT) of blood. In various aspects, the invention relates to an analyzer, a system, and a method for measuring at least a quantity of a first analyte and a quantity of a second analyte in a blood sample.

In various aspects of an analyzer for measuring at least a quantity of a first analyte and a quantity of a second analyte in a blood sample, the analyzer comprises:
  a. A housing.
  b. A receptor in the housing for receiving a removable cartridge comprising an optical chamber configured for receiving the blood sample.
  c. At least two electromagnetic radiation (EMR) sources. When the removable cartridge is received in the receptor, the EMR sources provide a first set of incident EMR to the optical chamber to interrogate the blood sample during a first time interval of a first duration, and a second set of incident EMR to the optical chamber to interrogate the blood sample during a second time interval of a second duration.
  d. An EMR dispersive element for producing:
    i. A first blood diffraction spectrum from a first set of emerging EMR emerging from the optical chamber, the first set of emerging EMR being generated by providing the first set of incident EMR to the optical chamber to interrogate the blood sample during the first time interval.
    ii. A first reference diffraction spectrum, wherein the first reference diffraction spectrum indicates intensities of the first set of incident EMR.
    iii. A second blood diffraction spectrum from a second set of emerging EMR emerging from the optical chamber, the second set of emerging EMR being generated by providing the second set of incident EMR to the optical chamber to interrogate the blood sample during the second time interval.
    iv. A second reference diffraction spectrum, wherein the second reference diffraction spectrum indicates intensities of the second set of incident EMR.
  e. A one-dimensional multi-channel detector for converting:
    i. The first blood diffraction spectrum into a first set of blood digital electrical signals to produce a first blood digital spectrum at a first wavelength range.
    ii. The first reference diffraction spectrum into a first set of reference digital electrical signals to produce a first reference digital spectrum at the first wavelength range.
    iii. The second blood diffraction spectrum into a second set of blood digital electrical signals to produce a second blood digital spectrum at a second wavelength range.
    iv. The second reference diffraction spectrum into a second set of reference digital electrical signals to produce a second reference digital spectrum at the second wavelength range.
  f. At least one data processor for determining;
    i. the quantity of the first analyte based on at least a portion of the first blood digital spectrum at a first plurality of wavelengths within the first wavelength range and the first reference digital spectrum at the first plurality of wavelengths.
    ii. The quantity of the second analyte based on at least a portion of the second blood digital spectrum at a second plurality of wavelengths within the second wavelength range and the second reference digital spectrum at the second plurality of wavelengths.

The one-dimensional multi-channel detector has a saturation EMR intensity at each wavelength. In operation, increases in an intensity of an EMR signal received by the one-dimensional multi-channel detector beyond the saturation EMR intensity do not increase a digital signal derived by the one-dimensional multi-channel detector from that EMR signal, and, a maximum EMR intensity in the first reference digital spectrum at a wavelength within the first wavelength range and a maximum EMR intensity in the second reference digital spectrum at a wavelength within the second wavelength range exceed 10% of the saturation EMR intensity at the respective wavelengths.

In various embodiments of the analyzer as defined above, the first wavelength range is about 300 nm to about 500 nm, and the second wavelength range is about 400 nm to about 1,000 nm.

In various embodiments of the analyzer as defined above, the at least two EMR sources comprise an EMR source. The EMR source comprises an ultraviolet (UV) LED and a wafer having fluorescent material, wherein the wafer is attached to an EMR emitting surface of the UV LED. In operation, upon receiving UV EMR from the UV LED, the wafer having fluorescent material produces at least a portion of the first set of incident EMR. Therefore, in this embodiment at least a portion of the first set of incident EMR is fluorescence emission. The wafer having fluorescent material, may further comprise at least one of silicon, silicon dioxide, quartz, and glass.

In various embodiments of the analyzer as defined above, the at least two EMR sources further comprises a second EMR source. The second EMR source is one of a white LED, a white-near infrared LED, an incandescent lamp, or a fluorescent lamp.

In various embodiments of the analyzer as defined above, at least the EMR source comprising the UV LED, further comprises a glass filter for at least absorbing some of the UV EMR emerging from the UV LED at wavelengths shorter than about 300 nanometers. The UV LED emits EMR towards the wafer within an approximate wavelength range of about 200 nanometers to about 400 nanometers.

In various embodiments of the analyzer as defined above, the wavelength of maximum EMR intensity of the first set of incident EMR is within the wavelength range of about 300 nm to about 500 nm.

In various embodiments of the analyzer as defined above, in operation, the at least one data processor controls the operating of the at least two EMR sources to control when the first time interval and the second time interval occur such that at least a portion of the first time interval occurs when the second time interval is not occurring; and, at least a portion of the second time interval occurs when the first time interval is not occurring. The at least one data processor may control when the first time interval and the second time interval occur such that the first time interval and the second time interval do not overlap in time.

In various embodiments of the analyzer as defined above, the EMR dispersive element is one of a diffraction grating, a prism, and a combination thereof, and wherein the diffraction grating is one of a reflective diffraction grating and a transmission diffraction grating.

In various embodiments of the analyzer as defined above, the at least two EMR sources, the one-dimensional multi-channel detector, the EMR dispersive element, and the at least one processor are fixedly attached to the housing such that the at least two EMR sources, the one-dimensional multi-channel detector, the EMR dispersive element, and the at least one processor are substantially stationary relative to the housing and each other.

In various embodiments of the analyzer as defined above, the analyzer further comprises a fiber optic cable for directing the first set of emerging EMR and the second set of emerging EMR to the EMR dispersive element.

In various aspects of a system for measuring at least a quantity of a first analyte and a quantity of a second analyte in a blood sample, the system comprises:
  a. A removable cartridge comprising an optical chamber for receiving the blood sample.
  b. An analyzer as defined above.

In various embodiments of the system as defined above, the removeable cartridge is a single-use removeable cartridge, and the single-use removeable cartridge comprises a plurality of single-use removeable cartridges.

In various embodiments of the system as defined above, the analyzer comprises a plurality of analyzers. The plurality of analyzers comprise one or more parent analyzers and one or more child analyzers. In operation, the one or more parent analyzers provide data to develop a first analyte calibration and a second analyte calibration equation and subsequently, the first analyte calibration equation and the second analyte calibration equation are transferred to the one or more child analyzers. Each of the plurality of analyzers further comprises an associated non-transient computer-readable memory. Stored on the associated non-transient computer-readable memory are:
  a. An analyzer-specific wavelength table specific to that analyzer.
  b. A first analyte calibration equation for determining from spectral information the quantity of the first analyte.
  c. A second analyte calibration equation for determining from spectral information the quantity of the second analyte.
  d. A standard wavelength table comprising a set of wavelengths defined by a range and an arbitrarily chosen increment, wherein the range at least encompasses, wavelengths of the spectral information associated with the first analyte calibration equation and wavelengths of the spectral information associated with the second analyte calibration equation.

For each analyzer of the plurality of analyzers, the one-dimensional multi-channel detector for that analyzer comprises a linear repetitive installation of an associated plurality of discrete photo diodes on an integrated circuit chip. The analyzer-specific wavelength table indicates a wavelength assigned to each photo diode in the associated plurality of discrete photo diodes of the one-dimensional multi-channel detector of that analyzer after a process of wavelength calibration. In operation, the at least one data processor of that analyzer maps the at least a portion of the first blood digital spectrum at the first plurality of wavelengths, at least a portion of the first reference digital spectrum wherein the portion corresponds with the portion of the first blood digital spectrum, the at least a portion of the second blood digital spectrum at the second plurality of wavelengths, at least a portion of the second reference digital spectrum wherein the portion corresponds with the portion of the second blood digital spectrum, onto the standard wavelength table, to enable that analyzer to use the first analyte calibration equation and the second analyte calibration equation.

In various embodiments of the system as defined above, the analyzer lacks a hemolyzing means for altering the blood to an optically clear solution, such that, in operation, the blood sample interrogated within the optical chamber comprises most of the red blood cells drawn from a patient.

In various aspects of a method for measuring at least a quantity of a first analyte and a quantity of a second analyte in a blood sample, the method comprises:
  a. Providing the blood sample to an optical chamber.
  b. Operating at least two electromagnetic radiation (EMR) sources to produce a first set of emerging EMR and a second set of emerging EMR by interrogating the blood sample within the optical chamber, respectively with a first set of incident EMR during a first time interval of a first duration, and a second set of incident EMR during a second time interval of a second duration.

c. Producing the first reference digital spectrum at least once, whereby the first reference digital spectrum comprises at least one first reference digital spectra.
d. Producing the second reference digital spectrum at least once, whereby the second reference digital spectrum comprises at least one second reference digital spectra.
e. Operating a one-dimensional multi-channel detector to convert:
   i. The first blood diffraction spectrum into a first set of blood digital electrical signals to produce a first blood digital spectrum at a first wavelength range.
   ii. The second blood diffraction spectrum into a second set of blood digital electrical signals to produce a second blood digital spectrum at a second wavelength range.
f. Operating at least one data processor to determine:
   i. The quantity of the first analyte based on at least a portion of the first blood digital spectrum at a first plurality of wavelengths within the first wavelength range and a first reference digital spectrum indicating intensities of the first set of incident EMR at the first plurality of wavelengths.
   ii. The quantity of the second analyte based on at least a portion of the second blood digital spectrum at a second plurality of wavelengths within the second wavelength range and a second reference digital spectrum indicating intensities of the second set of incident EMR at the second plurality of wavelengths.

The one-dimensional multi-channel detector has a saturation EMR intensity at each wavelength. Increases in an intensity of an EMR signal received by the one-dimensional multi-channel detector beyond the saturation EMR intensity do not increase a digital signal derived from the one-dimensional multi-channel detector in response to that EMR signal; and, a maximum EMR intensity in the first reference digital spectrum at a wavelength within the first wavelength range and a maximum EMR intensity in the second reference digital spectrum at a wavelength within the second wavelength range exceed 10% of the saturation EMR intensity at the respective wavelengths.

In various embodiments of the method defined above, the first analyte is a species of bilirubin and the second analyte is a species of hemoglobin.

In various embodiments of the method defined above, the optical chamber is part of a removable cartridge, the at least two EMR sources, and the at least one data processor are part of an analyzer; the removable cartridge is receivable within a receptor of the analyzer; and the method further comprises inserting the removable cartridge into the receptor, and then operating the analyzer to determine the quantity of the first analyte and the quantity of the second analyte.

In various embodiments of the method defined above, the method further comprises:
   a. Producing the first reference digital spectrum, wherein producing the first reference digital spectrum comprises providing the first set of incident EMR for the first duration when the receptor is devoid of blood.
   b. Producing the second reference digital spectrum, wherein producing the second reference digital spectrum comprises providing the second set of incident EMR for the second duration when the receptor is devoid of blood.

In various embodiments of the method defined above, the method comprises, a plurality of blood samples. For each blood sample of the plurality of blood samples, determining the quantity of the first analyte and the quantity of the second analyte further comprises:

a. Storing at least one of the first reference digital spectrum and the second reference digital spectrum in a non-transient computer-readable memory, and for each blood sample of the plurality of blood samples.
b. Operating the at least one data processor to determine the quantity of the first analyte comprises retrieving the first reference digital spectrum from the non-transient computer-readable memory, or operating the at least one data processor to determine the quantity of the second analyte comprises retrieving the second reference digital spectrum from the non-transient computer-readable memory.

In various embodiments of the method defined above, the method further comprises periodically updating the first reference digital spectrum and the second reference digital spectrum stored in the non-transient computer-readable memory.

In various embodiments of the method defined above, the at least two EMR sources comprise a first EMR source for providing the first set of incident EMR, and a second EMR source for providing the second set of incident EMR.

In various embodiments of the method defined above, the method further comprises storing, in a non-transient computer-readable memory, a first analyte calibration equation for determining from spectral information the quantity of the first analyte, and a second analyte calibration equation for determining from spectral information the quantity of the second analyte, wherein:
   a. Operating the at least one data processor to determine the quantity of the first analyte comprises determining the quantity of the first analyte from the at least a portion of the first blood digital spectrum at the first plurality of wavelengths, the first reference digital spectrum at the first plurality of wavelengths, and the first analyte calibration equation.
   b. Operating the at least one data processor to determine the quantity of the second analyte comprises determining the quantity of the second analyte from the at least a portion of the second blood digital spectrum at the second plurality of wavelengths, the second reference digital spectrum at the second plurality of wavelengths, and the second analyte calibration equation.

In various embodiments of the method defined above, the method further comprises:
   a. Producing the first reference digital spectrum, wherein producing the first reference digital spectrum comprises providing the first set of incident EMR when the removable cartridge is not within the receptor.
   b. Producing the second reference digital spectrum, wherein producing the second reference digital spectrum comprises providing the second set of incident EMR when the removable cartridge is not within the receptor.

In various embodiments of the method defined above, the method further comprises controlling a timing of the first time interval and the second time interval to not overlap.

In various embodiments of the method defined above, the method further comprises deriving one of, an order derivative of absorbance, an order derivative of transmittance, an order derivative of reflectance data, and any combination thereof, from the at least a portion of the first digital spectrum at the first plurality of wavelengths.

In various embodiments of the method defined above, the quantity of the first analyte comprises deriving one of, a zero order derivative of absorbance, a first order derivative of absorbance, a second order derivative of absorbance, and any combination thereof, from the at least a portion of the first digital spectrum.

In various embodiments of the method defined above, wherein the blood sample drawn from a patient initially includes a plurality red blood cells, the method further comprises: providing and interrogating the blood sample without breaking down most of the plurality red blood cells.

In various embodiments of the method defined above, a maximum EMR intensity in the first reference digital spectrum at a wavelength within the first wavelength range and a maximum EMR intensity in the second reference digital spectrum at a wavelength within the second wavelength range exceed 20% of the saturation EMR intensity at the respective wavelengths.

In various embodiments of the method defined above, the method further comprises developing the first analyte calibration equation and the second calibration equation, wherein, developing the first analyte calibration equation and the second calibration equation comprise:
 a. Acquiring a first analyte calibration set comprising greater than ten blood samples having greater than ten known first analyte quantities.
 b. Acquiring a second analyte calibration set comprising greater than ten blood samples having greater than ten known second analyte quantities.
 c. Collecting a set of first analyte calibration spectral information comprising a first blood digital spectrum and a second blood digital spectrum for each blood sample of the first analyte calibration set.
 d. Collecting a set of second analyte calibration spectral information comprising a first blood digital spectrum and a second blood digital spectrum for each blood sample of the second analyte calibration set.
 e. Producing one or more of the first reference digital spectrum.
 f. Producing one or more of the second reference digital spectrum.
 g. Developing the first analyte calibration equation by applying known chemometric techniques to the set of first analyte calibration spectral information, the plurality of the first reference digital spectra, the plurality of the second reference digital spectra, the greater than ten known first analyte quantities.
 h. Developing the second analyte calibration equation by applying known chemometric techniques to the set of second analyte calibration spectral information, the plurality of the first reference digital spectra, the plurality of the second reference digital spectra, and the greater than ten known second analyte quantities.

Other aspects and features of the present invention will become apparent to those having ordinary skill in the art, upon review of the following description of specific embodiments of the invention, which are provided as non-limiting examples.

BRIEF DESCRIPTION OF THE DRAWINGS

A better understanding of the novel features and advantages of the present invention will be made by reading the detailed description of the preferred embodiments provided later, in conjunction with the accompanying drawings, in which:

FIG. 2A is an exploded perspective top view of a measurement cartridge 10a for measuring at least one property of blood, according to a first embodiment of a measurement cartridge;

FIG. 2B is a bottom view of the first housing member 30a of the measurement cartridge shown in FIG. 2A;

FIG. 2C is the bottom view of the first housing member 30a of the measurement cartridge shown in FIG. 2B, overlaid by and in alignment with a gasket 100a shown in FIG. 2A;

FIG. 2D is a top view of the second housing member 40a of the measurement cartridge shown in FIG. 2A;

FIG. 2E is the top view of the second housing member 40a shown in FIG. 2D, overlaid by and in alignment with the gasket 100a shown in FIG. 2A;

FIG. 2F is a perspective top view of the measurement cartridge 10a shown in FIG. 2A, in an open configuration;

FIG. 2G is a perspective bottom view of the measurement cartridge 10a shown in FIG. 2F;

FIG. 3A is top view of the measurement cartridge 10a shown in FIG. 2A, in an open configuration;

FIG. 3B is top view of the cartridge 10a shown in FIG. 2A, in a closed configuration;

FIG. 3C is an enlarged cross-sectional view through the cartridge 10a shown in FIG. 3A along line C-C;

FIG. 3D is an enlarged cross-sectional view through the cartridge 10a shown in FIG. 3B along line D-D;

FIG. 3E is an enlarged cross-sectional view through the cartridge 10a shown in FIG. 3B along line E-E;

FIG. 3F is a detailed view of detail F of the bottom portion of the sample storage well shown in FIG. 3E;

FIG. 4A is an exploded perspective top view of a calibration cartridge 20a for calibrating one or more electrochemical sensors, according to a first embodiment of a calibration cartridge;

FIG. 4B is a bottom view of the first housing member 50a of the calibration cartridge shown in FIG. 4A;

FIG. 4C is the bottom view of the first housing member 50a of the calibration cartridge shown in FIG. 4B, overlaid by and in alignment with a gasket 102a shown in FIG. 4A;

FIG. 4D is a top view of the second housing member 60a of the calibration cartridge shown in FIG. 4A;

FIG. 4E is the top view of the second housing member 60a shown in FIG. 4D, overlaid by and in alignment with the gasket 102a shown in FIG. 4A;

FIG. 4F is a perspective top view of the calibration cartridge 20a shown in FIG. 4A;

FIG. 4G is a perspective bottom view of the calibration cartridge 20a shown in FIG. 4A, with the bottom laminate 99a removed;

FIG. 6A is an exploded perspective top view of a calibration cartridge 20b for calibrating one or more electrochemical sensors, according to a second embodiment of a calibration cartridge;

FIG. 6B is a perspective top view of the calibration cartridge 20b shown in FIG. 6A;

FIG. 6C is a perspective bottom view of the calibration cartridge 20b shown in FIG. 6A, with the bottom laminate 99b removed;

FIG. 7A is a top view of the calibration cartridge 20b shown in FIG. 6A;

FIG. 7B is a detailed view of detail B of the calibration cartridge 20b shown in FIG. 7A;

FIG. 7C is a perspective view of a directional valve element 69b of calibration cartridge 20b, which for example, could be an elastomeric flap;

FIG. 7D is an enlarged cross-sectional view through the calibration cartridge 20b shown in FIG. 7A along line D-D;

FIG. 7E is an enlarged cross-sectional view through the calibration cartridge 20b shown in FIG. 7A along line E-E;

FIG. 8A is a perspective top view of the second housing member 60b of the calibration cartridge 20b shown in FIG. 6A;

FIG. 8B is a perspective top view of the second housing member 60b of the calibration cartridge 20b shown in FIG. 8A, with directional valve element 69b inserted in a nest 64b shown in FIG. 8E;

FIG. 8C is a perspective bottom view of the first housing member 50b of the calibration cartridge 20b shown in FIG. 6A;

FIG. 8D is a perspective bottom view of the first housing member 50b of the calibration cartridge 20b shown in FIG. 8C, overlaid with and in alignment with gasket 102b, and in alignment with directional valve element 69b (which is usually inserted in the nest 64b);

FIG. 8E is a detailed view of detail E of second housing member 60b of calibration cartridge 20b shown in FIG. 8A;

FIG. 8F is a detailed view of detail F of second housing member 60b of calibration cartridge 20b shown in FIG. 8B;

FIG. 8G is a detailed view of detail G of first housing member 50b of calibration cartridge 20b shown in FIG. 8C;

FIG. 8H is a detailed view of detail H of first housing member 50b of calibration cartridge 20b shown in FIG. 8D;

FIG. 9A is an exploded perspective top view of a measurement cartridge 10b for measuring at least one property of blood, according to a second embodiment of a measurement cartridge;

FIG. 9B is a bottom view of the first housing member 30b of the measurement cartridge shown in FIG. 9A;

FIG. 9C is the bottom view of the first housing member 30b of the measurement cartridge shown in FIG. 9B, overlaid by and in alignment with a gasket 100b shown in FIG. 9A;

FIG. 9D is a top view of the second housing member 40b of the measurement cartridge shown in FIG. 9A;

FIG. 9E is the top view of the second housing member 40b shown in FIG. 9D, overlaid by and in alignment with the gasket 100b shown in FIG. 9A;

FIG. 9F is a perspective top view of the measurement cartridge 10b shown in FIG. 9A, in an open configuration;

FIG. 9G is a perspective bottom view of the measurement cartridge 10b shown in FIG. 9F;

FIG. 10A is an exploded perspective top view of a measurement cartridge 10c for measuring at least one property of blood, according to a third embodiment of a measurement cartridge;

FIG. 10B is a perspective top view of the measurement cartridge 10c shown in FIG. 10A, in an open configuration;

FIG. 10C is a perspective bottom view of the measurement cartridge 10c shown in FIG. 10B;

FIG. 10D is a top view of the measurement cartridge 10c shown in FIG. 10A, in a closed configuration;

FIG. 10E is an enlarged cross-sectional view through the measurement cartridge 10c shown in FIG. 10D along line E-E;

FIG. 10F is an enlarged cross-sectional view through the measurement cartridge 10c shown in FIG. 10D along line F-F;

FIG. 10G is an enlarged cross-sectional view through the measurement cartridge 10c shown in FIG. 10D along line G-G;

FIG. 13A is an exploded perspective top view of a measurement cartridge 10e for measuring at least one property of blood, according to a fifth embodiment of a measurement cartridge;

FIG. 13B is a bottom view of the first housing member 30e of the measurement cartridge shown in FIG. 13A;

FIG. 13C is the bottom view of the first housing member 30e of the measurement cartridge shown in FIG. 13B, overlaid by and in alignment with a gasket 100e shown in FIG. 13A;

FIG. 13D is a top view of the second housing member 40e of the measurement cartridge shown in FIG. 13A;

FIG. 13E is the top view of the second housing member 40a shown in FIG. 13D, overlaid by and in alignment with the gasket 100e shown in FIG. 13A;

FIG. 13F is a perspective top view of the cartridge 10e shown in FIG. 13A, in a closed configuration;

FIG. 13G is a perspective bottom view of the measurement cartridge 10e shown in FIG. 13A;

FIG. 14A is top view of the measurement cartridge 10e shown in FIG. 13A, in an open configuration;

FIG. 14B is an enlarged cross-sectional view through the measurement cartridge 10e shown in FIG. 14A along line B-B;

FIG. 14C is top view of the measurement cartridge 10e shown in FIG. 13A, in a closed configuration;

FIG. 14D is an enlarged cross-sectional view through the measurement cartridge 10e shown in FIG. 14C along line D-D;

FIG. 14E is a detailed view of detail E of measurement cartridge 10e shown in FIG. 14D;

FIG. 14F is a detailed view of detail F of measurement cartridge 10e shown in FIG. 14A;

FIG. 16A is an exploded perspective top view of a measurement cartridge 10f for measuring at least one property of blood, according to a sixth embodiment of a measurement cartridge;

FIG. 16B is a bottom view of the first housing member 30f of the measurement cartridge shown in FIG. 16A;

FIG. 16C is the bottom view of the first housing member 30f of the measurement cartridge shown in FIG. 16B, overlaid by and in alignment with a gasket 100f shown in FIG. 16A;

FIG. 16D is a top view of the second housing member 40f of the measurement cartridge shown in FIG. 16A;

FIG. 16E is the top view of the second housing member 40f shown in FIG. 16D, overlaid by and in alignment with the gasket 100f shown in FIG. 16A;

FIG. 16F is a perspective top view of the measurement cartridge 10f shown in FIG. 16A, in an open configuration;

FIG. 16G is a perspective bottom view of the measurement cartridge 10f shown in FIG. 16A;

FIG. 17A is a top view of the measurement cartridge 10f shown in FIG. 16A, in a closed configuration;

FIG. 17B is an enlarged cross-sectional view through the measurement cartridge 10f shown in FIG. 17A along line B-B;

FIG. 17C is a detailed view of detail C of measurement cartridge 10f shown in FIG. 17B;

FIG. 17D is a detailed view of detail D of measurement cartridge 10f shown in FIG. 17C;

FIG. 20A is a top view of the measurement cartridge 10g shown in FIG. 19A, in a closed configuration;

FIG. 20B is a perspective top view of directional valve element 67g;

FIG. 20C is a perspective top view of directional valve element 68g;

FIG. 20D is an enlarged cross-sectional view through the measurement cartridge 10g shown in FIG. 20A along line D-D;

FIG. 20E is an enlarged cross-sectional view through the measurement cartridge 10g shown in FIG. 20A along line E-E;

FIG. 20F is an enlarged cross-sectional view through the measurement cartridge 10g shown in FIG. 20A along line F-F;

FIG. 20G is an enlarged cross-sectional view through the measurement cartridge 10g shown in FIG. 20A along line G-G;

FIG. 21A is a perspective top view of the second housing member 40g of the measurement cartridge 10g shown in FIG. 19A;

FIG. 21B is the perspective top view of the second housing member 40g of the measurement cartridge 10g shown in FIG. 21A, showing directional valve elements 67g and 68g seated in their respective nests 65g and 66g;

FIG. 21C is the perspective top view of the second housing member 40g of the measurement cartridge 10g shown in FIG. 21B, overlaid by and in alignment with the gasket 100g shown in FIG. 19A;

FIG. 21D is a perspective bottom view of the first housing member 30g of the measurement cartridge 10g shown in FIG. 19A;

FIG. 21E is a detailed view of detail E of second housing member 40g of measurement cartridge 10g shown in FIG. 21A;

FIG. 21F is a detailed view of detail F of second housing member 40g of measurement cartridge 10g shown in FIG. 21B;

FIG. 21G is a detailed view of detail G of second housing member 40g of measurement cartridge 10g shown in FIG. 21C;

FIG. 21H is a detailed view of detail H of first housing member 30g of measurement cartridge 10g shown in FIG. 21D;

FIG. 21J is a detailed view of detail J of first housing member 30g of measurement cartridge 10g shown in FIG. 21D;

FIG. 22A is an exploded perspective top view of a measurement cartridge 10h for measuring at least one property of blood, according to an eighth embodiment of a measurement cartridge;

FIG. 22B is a bottom view of the first housing member 30h of the measurement cartridge shown in FIG. 22A;

FIG. 22C is the bottom view of the first housing member 30*h* of the measurement cartridge shown in FIG. 22B, overlaid by and in alignment with a gasket 100*h* shown in FIG. 22A;

FIG. 22D is a top view of the second housing member 40*h* of the measurement cartridge shown in FIG. 22A;

FIG. 22E is the top view of the second housing member 40*h* shown in FIG. 22D, overlaid by and in alignment with the gasket 100*h* shown in FIG. 22A;

FIG. 22F is a perspective top view of the measurement cartridge 10*h* shown in FIG. 22A in an open configuration;

FIG. 22G is a perspective bottom view of the measurement cartridge 10*h* shown in FIG. 22A;

FIG. 23A is a top view of the measurement cartridge 10*h* shown in FIG. 22A, with the cap in a closed configuration;

FIG. 23B is an enlarged cross-sectional view through the measurement cartridge 10*h* shown in FIG. 23A along line B-B;

FIG. 23C is an enlarged cross-sectional view through the measurement cartridge 10*h* shown in FIG. 23A along line C-C;

Figure 24:
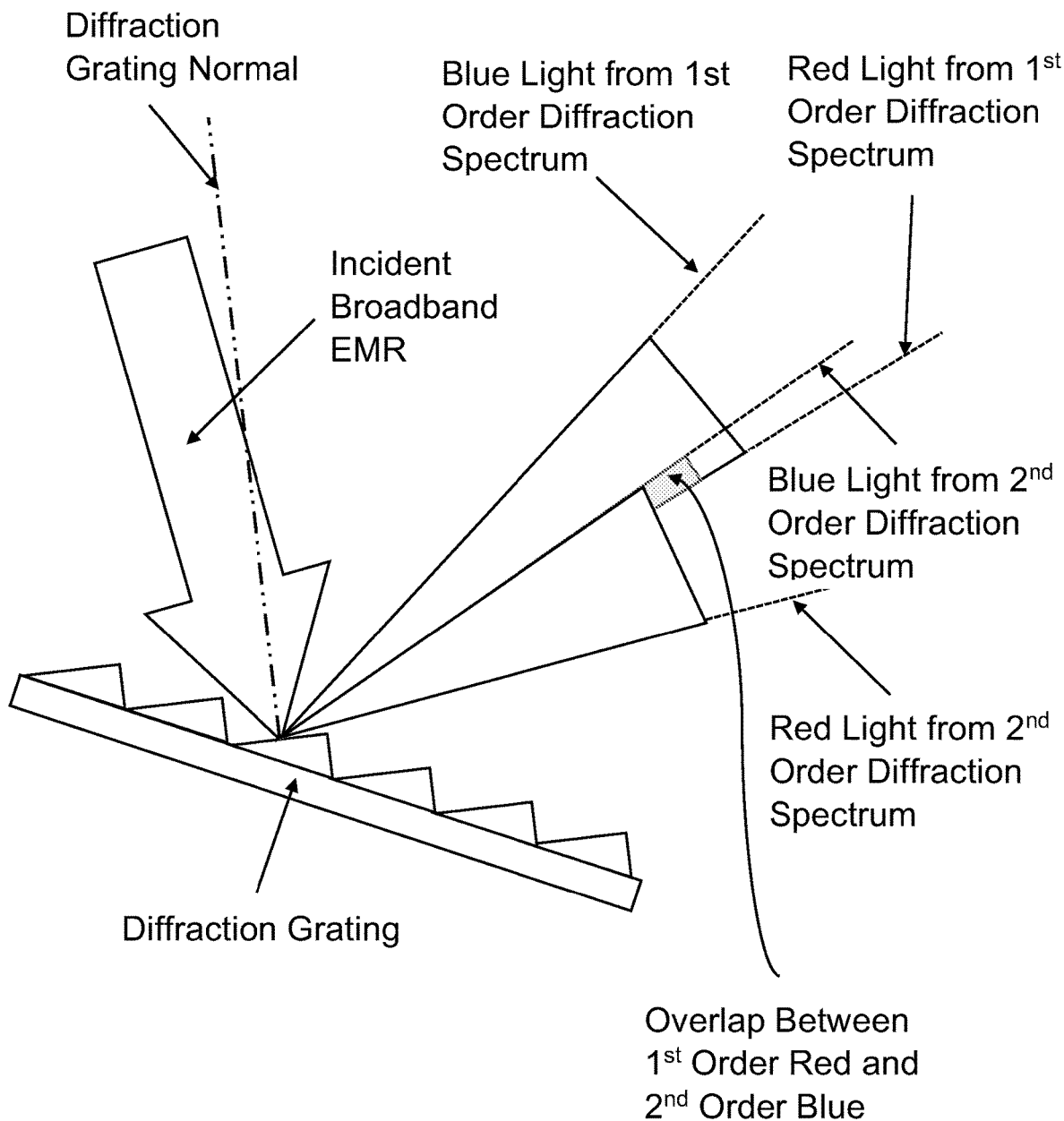
Figure 25:
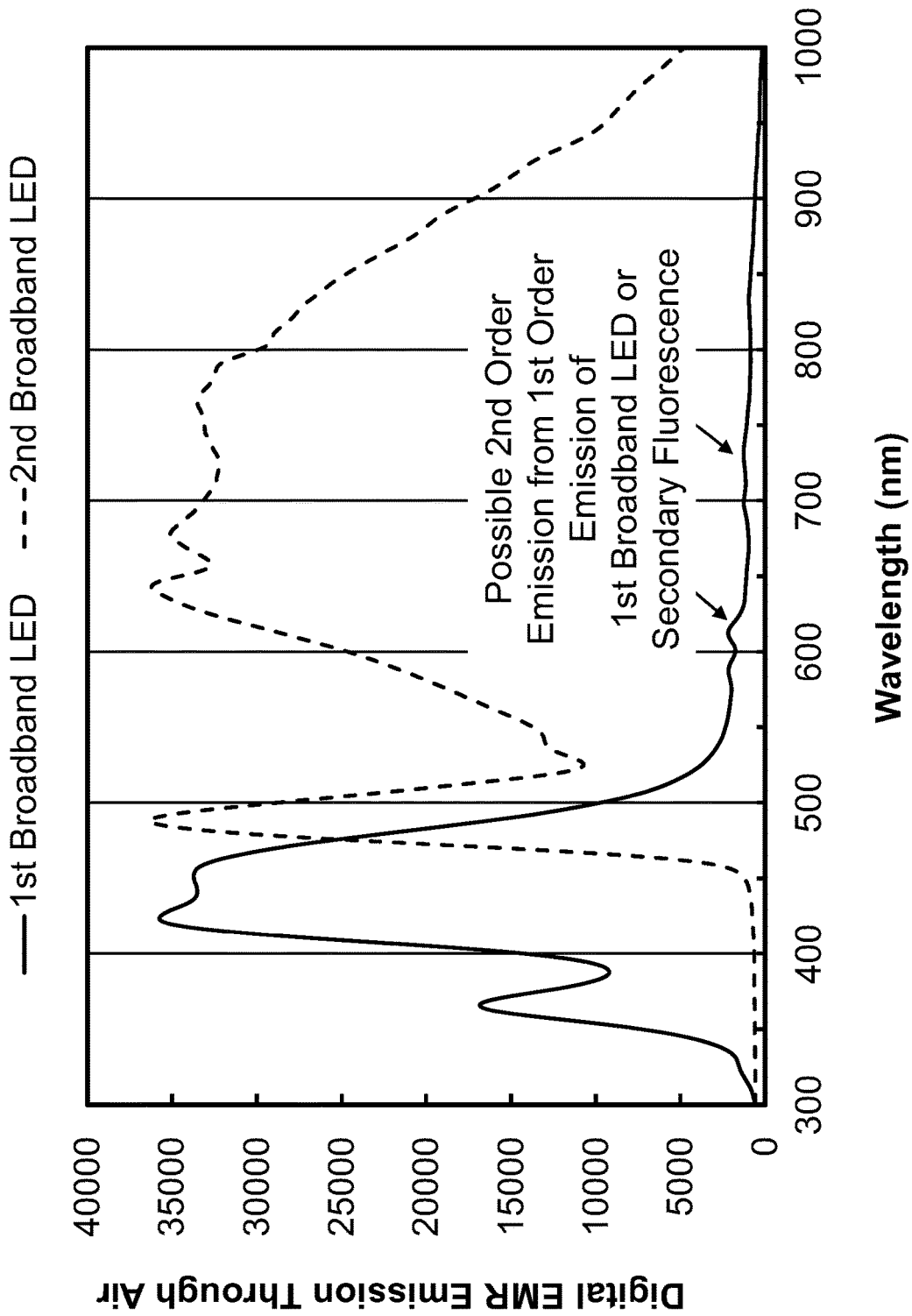
Figure 26:
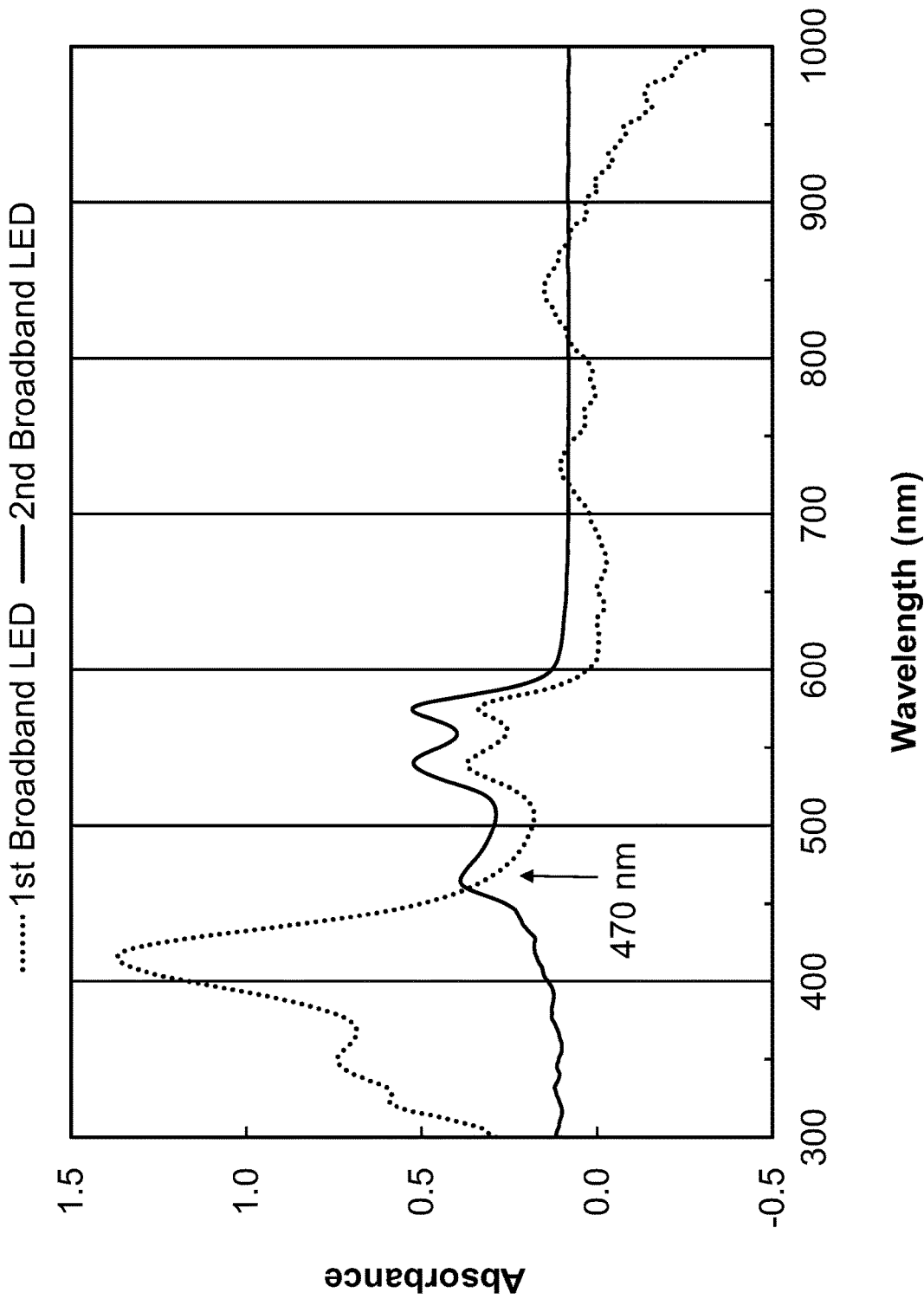
Figure 27:
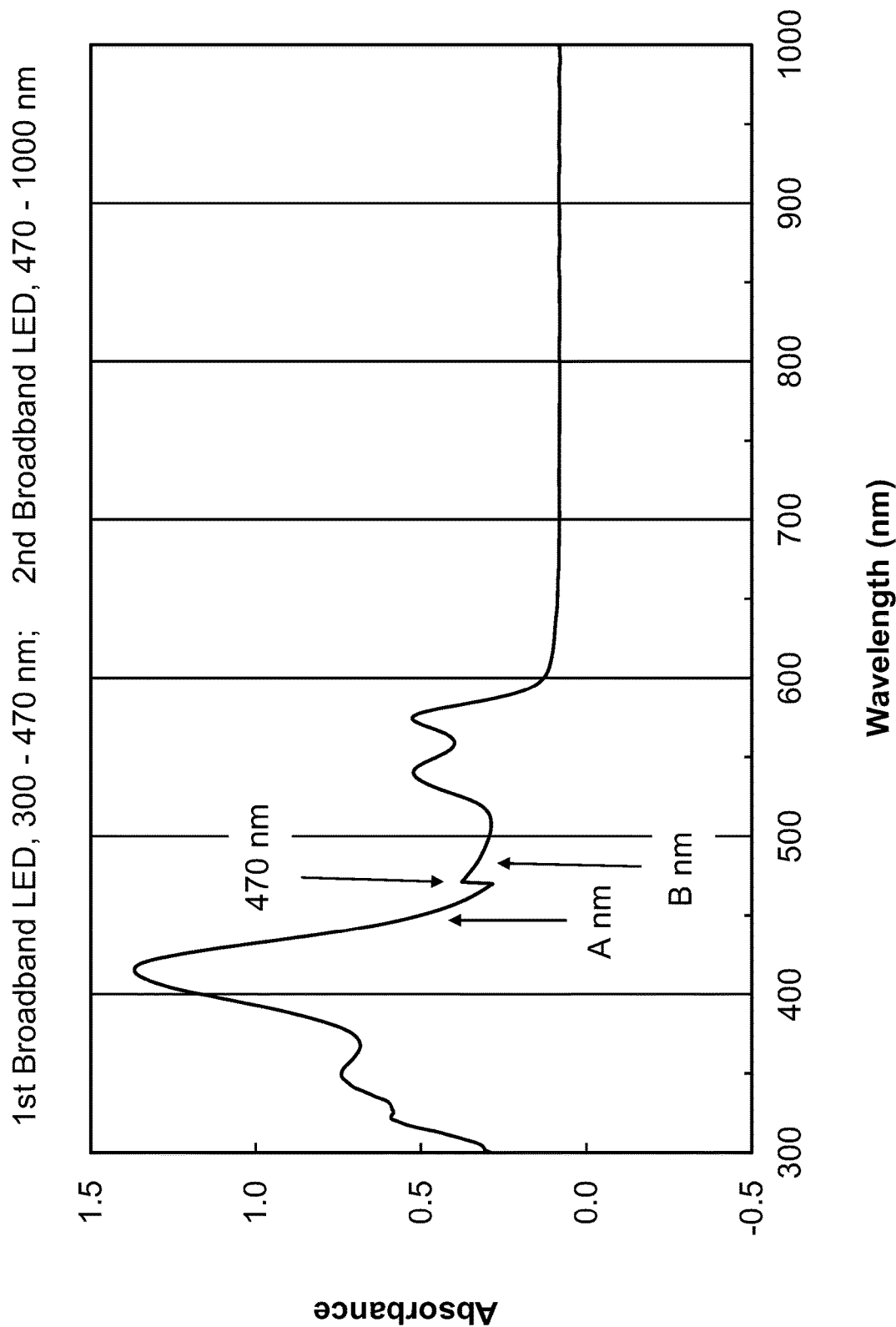
Figure 28:
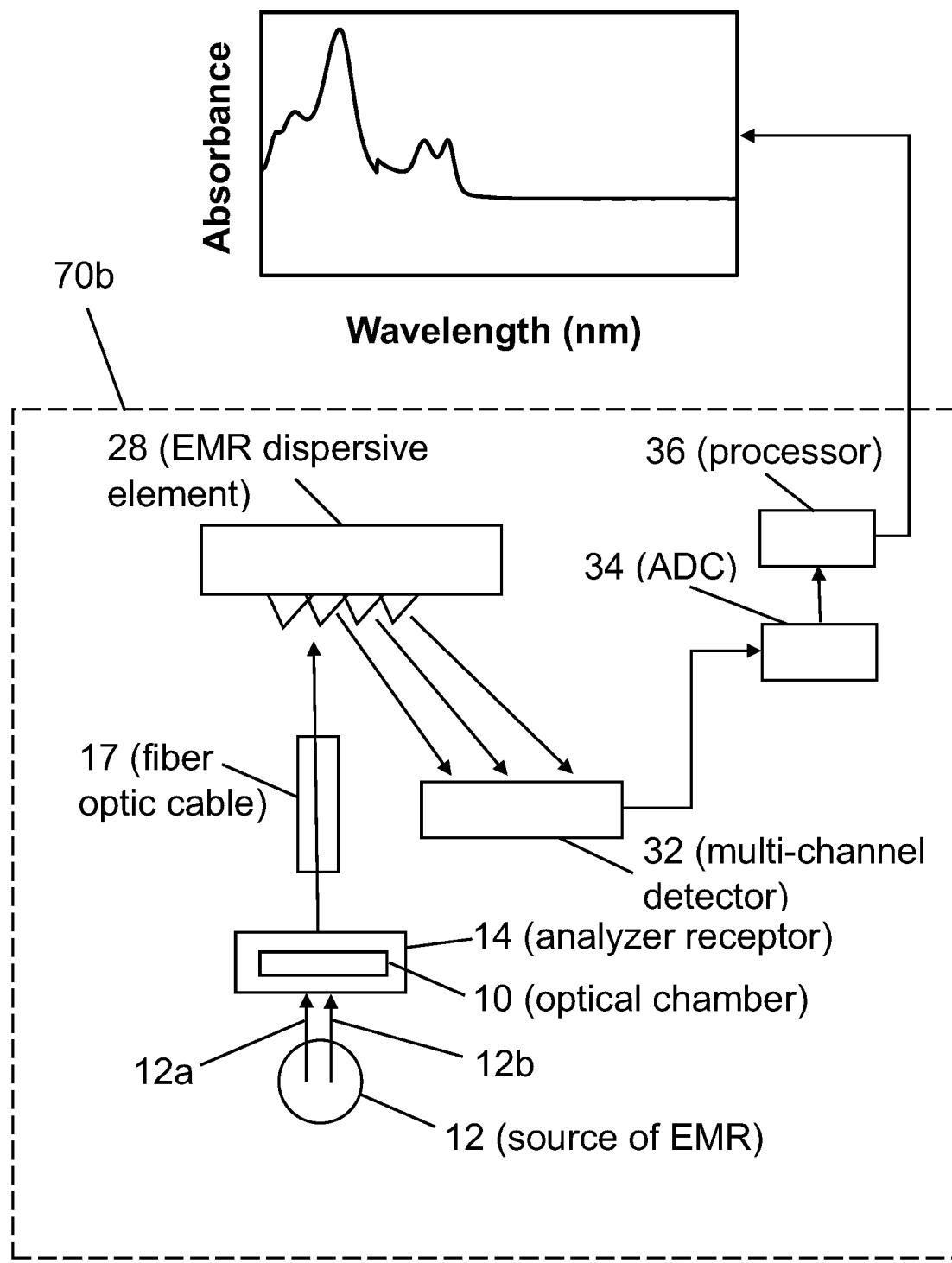

FIG. 23D is a detailed view of detail D of measurement cartridge 10*h* shown in FIG. 23C;

FIG. 24 is a diagram of a reflective diffraction grating illustrating overlap between the first order and second order diffraction spectra of incident broadband EMR;

FIG. 25 is graph of the digital electrical signals derived by a one-dimensional multi-channel detector, representing EMR emission spectra of two broadband LEDs;

FIG. 26 are graphs of the absorbance spectra of unaltered blood using two separate broadband LEDs;

FIG. 27 is a composite absorbance spectrum of the two absorbance spectra illustrated in FIG. 26;

FIG. 28 is a block diagram of a system used to generate the spectra illustrated in FIGS. 25-27;

FIG. 29 are published absorbance spectra of bilirubin and several hemoglobin species (available on the Internet as https://www.researchgate.net/publication/7157559_Noninvasive_detection_of_bilirubin_using_pulsatile_absorption); and FIG. 30 are graphs of digital background electrical signals derived by a one-dimensional multi-channel detector, at two different ITs.

For a better understanding of the present invention, and to show more clearly how it may be carried into effect, reference will now be made, by way of example, to the accompanying drawings, and which are described in the following detailed description of preferred aspects of the invention.

DETAILED DESCRIPTION OF PREFERRED ASPECTS OF THE INVENTION

POCT systems comprising an analyzer, a measurement cartridge having one or more electrochemical sensors in a detection chamber, and a calibration cartridge having one or more similar electrochemical sensors are described. Systems comprising measurement cartridges having no calibration liquid blisters, and calibration cartridges having one or two calibration liquid blisters for performing one-point calibration (for offset correction) or two-point calibration (offset and slope correction), respectively, are described. Also described are systems comprising measurement cartridges having one calibration liquid blister for performing one-point calibration and calibration cartridges having two calibration liquid blisters for performing two-point calibration. Although the examples of calibration cartridges illustrate one and two calibration liquid blisters for simplicity, any number of calibration liquid blisters are considered to be within the scope of the present application. Also described are measurement cartridges comprising one or more detection chambers, wherein the one or more detection chambers comprise one or more optical chambers.

In this application, two types of cartridges are described: 1) Calibration Cartridges, and 2) Measurement Cartridges. In the calibration cartridge, no sample storage well is required, wherein the calibration liquid conduit entering the electrochemical sensor conduit is closed off from any other liquid influx, like influx of blood. For illustration, two examples of calibration cartridges, 20*a* and 20*b*, are provided, and eight examples of measurement cartridges, 10*a*, 10*b*, 10*c*, 10*d*, 10*e*, 10*f*, 10*g* and 10*h*, are provided. The calibration and measurement cartridges are removable from the analyzer receptor after each use. Preferably, they are single-use cartridges. Various combinations of detection chambers in the measurement cartridges are provided, in order to increase the versatility of the measurement cartridges.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments consist essentially of those elements and/or steps, and in other embodiments consist of those elements and/or steps, whether or not these embodiments are specifically referred to. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−25% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The terms "operatively connected", "in operative communication", "in fluid communication", "in fluid connection" or "fluidly connected" and the like, describe elements of the cartridges, for example, channels, ducts, conduits, tunnels, passageways, that permit either fluid flow, gas flow, or both fluid and gas flow between the various compartments or elements within the cartridge that are connected by the channels, ducts, conduits, tunnels, passageways and the like.

Detailed description of features of examples of the invention is described with reference to the accompanying drawings. These examples are to be considered non-limiting, and a person having ordinary skill in the art should understand that variations are within the scope of the invention, even though they are not explicitly illustrated. The same reference numerals are used for similar elements in different examples; in some cases, letters are appended to the end of the reference numerals to denote the embodiment of the invention illustrated. For example, 10a and 10b refer to two different examples of a Measurement Cartridge, and 20a and 20b refer to two different examples of a Calibration Cartridge. To maintain the distinction between a Measurement Cartridge and a Calibration Cartridge, attempts are made to provide different reference numerals for similar structures in the two different types of cartridges. It should be noted that absence of a letter after a reference numeral may refer to a structural feature of the invention incorporated in multiple examples. For easy reference, Table 1 provides a list of the reference numerals used, and a brief description of the corresponding structural features.

TABLE 1

Description of Structural Features.

Figure 15:
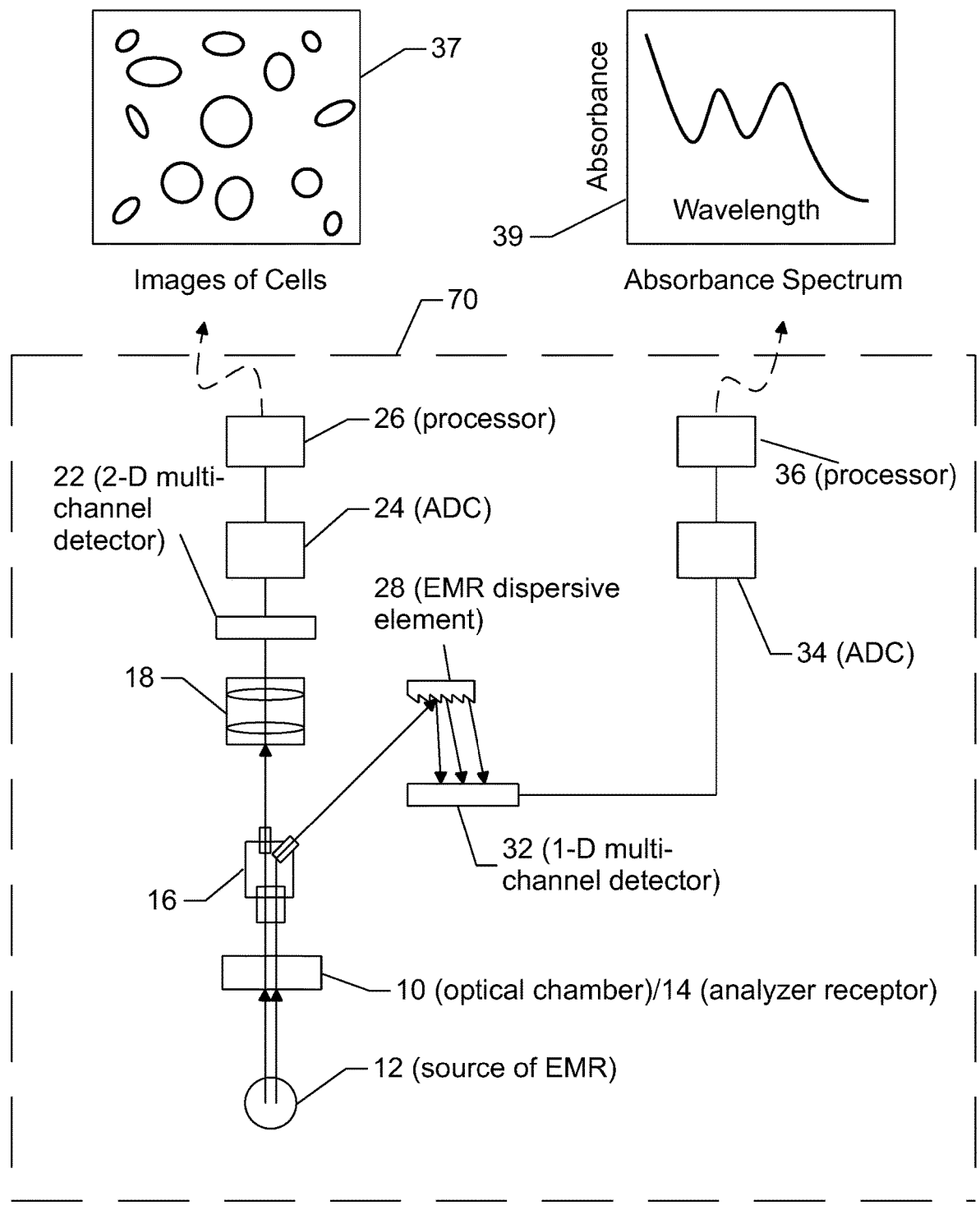
FIG. 15 is a block diagram of an example of a system 70 (lower panel) for measuring one or more analyte quantities per unit volume of blood and one or more formed element quantities per unit volume of blood, in a blood sample, and output displays of the system (upper left and right panels) are provided as non-limiting examples.
Figure 18A:
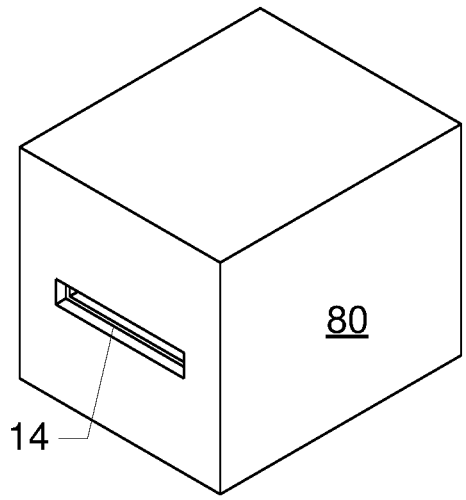
FIG. 18A is a perspective top view of a calibration cartridge 20b and an associated analyzer 80, having a receptor 14 for receiving measurement cartridge 20b.
Figure 18B:
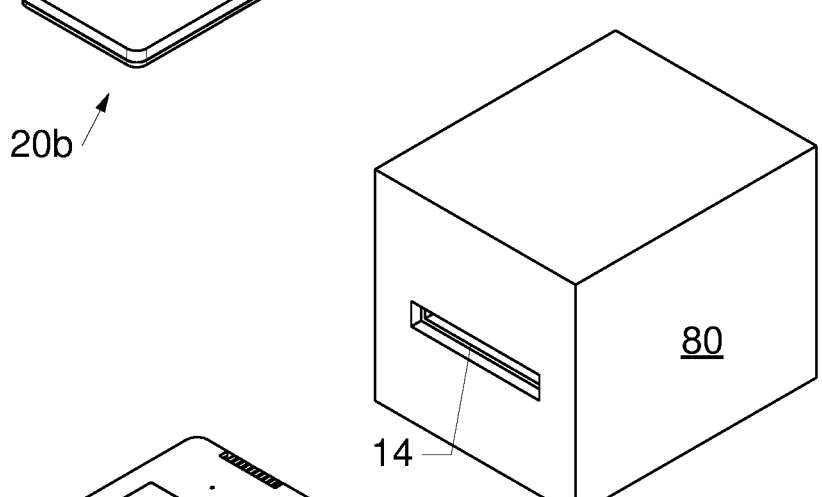
FIG. 18B is a perspective top view of a measurement cartridge 10b and the associate analyzer 80 shown in FIG. 18A.
Figure 18C:
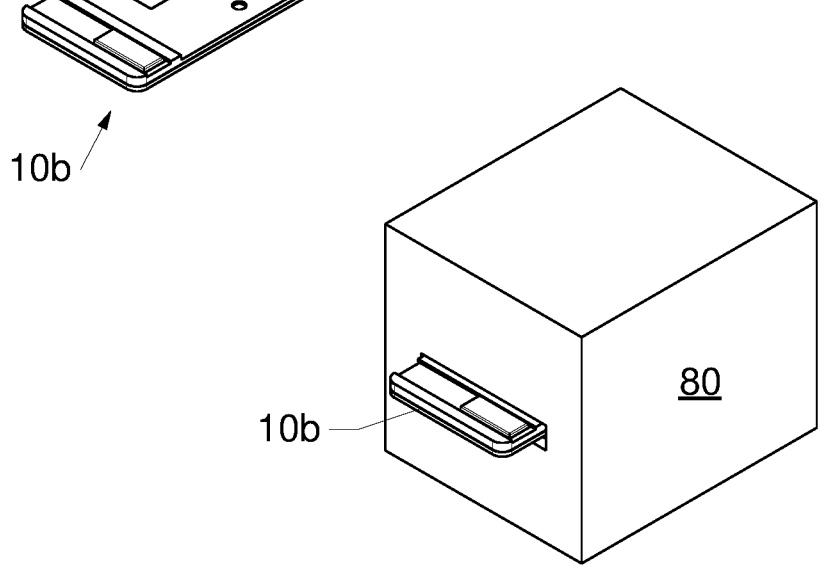
FIG. 18C is a perspective top view of the measurement cartridge 10b inserted in the slot 14 of the associated analyzer 80, shown in FIG. 18B.

| Reference Numerals | Description of Structural Features |
|---|---|
| 10 | Generic measurement cartridge having an optical chamber, depicted in FIG. 15 |
| 10a | First embodiment of a measurement cartridge |
| 10b | Second embodiment of a measurement cartridge |
| 10c | Third embodiment of a measurement cartridge |
| 10d | Fourth embodiment of a measurement cartridge |
| 10e | Fifth embodiment of a measurement cartridge |
| 10f | Sixth embodiment of a measurement cartridge |
| 10g | Seventh embodiment of a measurement cartridge |
| 10h | Eighth embodiment of a measurement cartridge |
| 12 | Source of electromagnetic radiation (EMR) of an analyzer of system 70 & 70b |
| 12a | first Broadband LED (light-emitting diode) |
| 12b | second Broadband LED |
| 14 | Generic receptor in an analyzer of system 70 for receiving a cartridge depicted in FIGS. 15 & 28, and analyzer 80 depicted in FIGS. 18A-18C |
| 16 | Beam splitter of an analyzer of system 70 (bifurcated fiber optic cable shown as an example) |
| 17 | Fiber optic cable |
| 18 | Magnifying system of an analyzer of system 70 |
| 20a | First embodiment of a calibration cartridge |
| 20b | Second embodiment of a calibration cartridge |
| 22 | Two-dimensional multi-channel detector of an analyzer of system 70 |
| 24 | Analog to digital converter (ADC) of an analyzer of system 70 |
| 26 | Processor of an analyzer of system 70 |
| 28 | EMR dispersive element, e.g. a grating or a prism (a grating shown) |
| 30a | First housing member of measurement cartridge 10a |
| 30b | First housing member of measurement cartridge 10b |
| 30c | First housing member of measurement cartridge 10c |
| 30c | First housing member of measurement cartridge 10d |
| 30e | First housing member of measurement cartridge 10e |
| 30f | First housing member of measurement cartridge 10f |
| 30g | First housing member of measurement cartridge 10g |
| 30h | First housing member of measurement cartridge 10h |
| 32 | One-dimensional multi-channel detector of analyzer 70 |
| 34 | Analog to digital converter (ADC) of an analyzer of system 70 |
| 36 | Processor of an analyzer of system 70 |
| 37 | Example of a display of two-dimensional detector 22 |
| 39 | Example of a display of one-dimensional detector 32 |
| 40a | Second housing member of measurement cartridge 10a |
| 40b | Second housing member of measurement cartridge 10b |
| 40c | Second housing member of measurement cartridge 10c |
| 40d | Second housing member of measurement cartridge 10d |
| 40e | Second housing member of measurement cartridge 10e |
| 40f | Second housing member of measurement cartridge 10f |
| 40g | Second housing member of measurement cartridge 10g |
| 40h | Second housing member of measurement cartridge 10h |
| 50a | First housing member of calibration cartridge 20a |
| 50b | First housing member of calibration cartridge 20b |
| 51a | Sample storage well of measurement cartridge 10a |
| 51b | Sample storage well of measurement cartridge 10b |
| 51c | Sample storage well of measurement cartridge 10c |
| 51d | Sample storage well of measurement cartridge 10d |
| 51e | Sample storage well of measurement cartridge 10e |
| 511 | Sample storage well of measurement cartridge 10f |
| 51g | Sample storage well of measurement cartridge 10g |
| 51h | Sample storage well of measurement cartridge 10h |
| 53a | Top opening (or top portion) of a sample storage well 51a |
| 53b | Top opening (or top portion) of a sample storage well 51b |
| 53c | Top opening (or top portion) of a sample storage well 51c |
| 53e | Top opening (or top portion) of a sample storage well 51e |
| 531 | Top opening (or top portion) of a sample storage well 51f |
| 53g | Top opening (or top portion) of a sample storage well 51g |
| 53h | Top opening (or top portion) of a sample storage well 51h |
| 55a | Bottom opening (or bottom portion) of a sample storage well 51a |
| 55b | Bottom opening (or bottom portion) of a sample storage well 51b |

TABLE 1-continued

Description of Structural Features.

| Reference Numerals | Description of Structural Features |
|---|---|
| 55c | Bottom opening (or bottom portion) of a sample storage well 51c |
| 55e | Bottom opening (or bottom portion) of a sample storage well 51e |
| 55f | Bottom opening (or bottom portion) of a sample storage well 51f |
| 55g | Bottom opening (or bottom portion) of a sample storage well 51g |
| 55h | Bottom opening (or bottom portion) of a sample storage well 51h |
| 56a | Extension of the bottom opening 55a of sample storage well 51a of cartridge 10a for connecting sample storage well 51a to blood flow conduit 259a |
| 56b | Extension of the bottom opening 55b of sample storage well 51b of cartridge 10b for connecting sample storage well 51b to blood flow conduit 259b |
| 56e | Extension of the bottom opening 55e of sample storage well 51e of cartridge 10e for connecting sample storage well 51e to blood flow conduit 259e |
| 56f | Extension of the bottom opening 55f of sample storage well 51f of cartridge 10f for connecting sample storage well 51f to blood flow conduit 259f |
| 56g | Extension of the bottom opening 55g of sample storage well 51g of measurement cartridge 10g for connecting sample storage well 51g to manifold 455g |
| 56h | Extension of the bottom opening 55h of sample storage well 51h of measurement cartridge 10h for connecting sample storage well 51h to manifold 455h |
| 57a | Sample inlet portion of cartridge 10a, which comprises some elements of the cartridge that interacts with the cap 200a |
| 57b | Sample inlet portion of cartridge 10b, which comprises some elements of the cartridge that interacts with the cap 200b |
| 57c | Sample inlet portion of cartridge 10c, which comprises some elements of the cartridge that interacts with the cap 200c |
| 58d | Sample storage well boss of cartridge 10d for increasing the sample storage well storage capacity |
| 59a | Flat surface of sample inlet portion 57a |
| 59b | Flat surface of sample inlet portion 57b |
| 59c | Flat surface of sample inlet portion 57c |
| 60a | Second housing member of calibration cartridge 20a |
| 60b | Second housing member of calibration cartridge 20b |
| 61a | Electrochemical sensor array of measurement cartridge 10a having at least one of an amperometric sensor, a conductivity sensor and a potentiometric sensor |
| 61b | Electrochemical sensor array of measurement cartridge 10b having at least one of an amperometric sensor, a conductivity sensor and a potentiometric sensor |
| 61c | Electrochemical sensor array of measurement cartridge 10c having at least one of an amperometric sensor, a conductivity sensor and a potentiometric sensor |
| 61d | Electrochemical sensor array of measurement cartridge 10d having at least one of an amperometric sensor, a conductivity sensor and a potentiometric sensor |
| 61f | Electrochemical sensor array of measurement cartridge 10f having at least one of an amperometric sensor, a conductivity sensor and a potentiometric sensor |
| 61g | Electrochemical sensor array of measurement cartridge 10g having at least one of an amperometric sensor, a conductivity sensor and a potentiometric sensor |
| 61h | Electrochemical sensor array of measurement cartridge 10h having at least one of an amperometric sensor, a conductivity sensor and a potentiometric sensor |
| 62a | Electrochemical sensor array of calibration cartridge 20a having at least one of an amperometric sensor, a conductivity sensor and a potentiometric sensor |
| 62b | Electrochemical sensor array of calibration cartridge 20b having at least one of an amperometric sensor, a conductivity sensor and a potentiometric sensor |
| 64b | Nest for seating directional valve element 69b |
| 65g | Nest for seating directional valve element 67g |
| 66g | Nest for seating directional valve element 68g |
| 66h | Nest for seating directional valve element 68h |
| 67g | First directional valve element of measurement cartridge 10g, which for example, could be an elastomeric flap |
| 68g | Second directional valve element of measurement cartridge 10g, which for example, could be an elastomeric flap |
| 68h | Directional valve element of measurement cartridge 10h, which for example, could be an elastomeric flap |
| 69b | Directional valve element of calibration cartridge 20b, which for example, may be an elastomeric flap |

TABLE 1-continued

Description of Structural Features.

| Reference Numerals | Description of Structural Features |
|---|---|
| 70 | System for measuring one or more properties of blood, shown in FIG. 15 |
| 70b | System for measuring one or more properties of blood, shown in FIG. 28 |
| 71b | Smaller section of directional valve element 69b that is flappable for closing off valve seat 327b (see FIG. 8G in conjunction with FIG. 8H) |
| 73b | Larger section of the directional valve element 69b that is used to seat directional valve element 69b in receptor 64b (see FIG. 8E) |
| 75g | Sealed blister for storing calibration fluid of measurement cartridge 10g |
| 76g | Compressible blister support for supporting blister 75g over spike 277g |
| 80 | Analyzer for measuring one or more properties of blood, shown in FIGS. 18A-18C |
| 81a | Ledge in second housing member 40a of measurement cartridge 10a for housing electrochemical sensor array 61a |
| 91a | Sealed blister for storing calibration fluid of calibration cartridge 20a |
| 92a | Compressible blister support for supporting sealed blister 91a over spike 271a |
| 93b | First sealed blister for storing first calibration fluid of calibration cartridge 20b |
| 95b | Second sealed blister for storing second calibration fluid of calibration cartridge 20b |
| 96b | Compressible blister support for supporting blister 93b over spike 273b |
| 97b | Compressible blister support for supporting blister 95b over spike 275b |
| 99a | Bottom laminate for covering blister outlet conduit 301a |
| 99b | Bottom laminate for covering blister outlet conduits 307b and 309b |
| 99g | Bottom laminate for covering blister outlet conduit 431g |
| 100a | Double-sided sticky gasket of measurement cartridge 10a |
| 100b | Double-sided sticky gasket of measurement cartridge 10b |
| 100c | Double-sided sticky gasket of measurement cartridge 10c |
| 100d | Double-sided sticky gasket of measurement cartridge 10d |
| 100e | Double-sided sticky gasket of measurement cartridge 10e |
| 100f | Double-sided sticky gasket of measurement cartridge 10f |
| 100g | Double-sided sticky gasket of measurement cartridge 10g |
| 100h | Double-sided sticky gasket of measurement cartridge 10h |
| 102a | Double-sided sticky gasket of calibration cartridge 20a |
| 102b | Double-sided sticky gasket of calibration cartridge 20b |
| 103a | Cutout in double-sided sticky gasket 100a aligned with the bottom opening 55a of sample storage well 51a of cartridge 10a |
| 103b | Cutout in double-sided sticky gasket 100b aligned with the bottom opening 55b of the sample storage well 51b of cartridge 10b |
| 103e | Cutout in double-sided sticky gasket 100e aligned with the bottom opening 55e of the sample storage well 51e of cartridge 10e |
| 103f | Cutout in double-sided sticky gasket 100f aligned with the bottom opening 55f of the sample storage well 51f of cartridge 10f |
| 103g | Cutout in double-sided sticky gasket 100g aligned with the bottom opening 55g of the sample storage well 51g of cartridge 10g |
| 103h | Cutout in double-sided sticky gasket 100h aligned with the bottom opening 55h of the sample storage well 51h of cartridge 10h |
| 105a | Cutout in double-sided sticky gasket 100a for mitigating blood flow from extension 56a of bottom opening 55a during sample loading |
| 105b | Cutout in double-sided sticky gasket 100b for mitigating blood flow from extension 56b of bottom opening 55b during sample loading |
| 105e | Cutout in double-sided sticky gasket 100e for mitigating blood flow from extension 56e of bottom opening 55e during sample loading |
| 105f | Cutout in double-sided sticky gasket 100f for mitigating blood flow from extension 56f of bottom opening 55f |
| 105g | Cutout in double-sided sticky gasket 100g for mitigating blood flow from extension 56g of bottom opening 55g |
| 105h | Cutout in double-sided sticky gasket 100h for mitigating blood flow from extension 56h of bottom opening 55h |
| 107a | Cutout in double-sided sticky gasket 100a aligned with hole in sealing member 241a and corresponding hole 242a in cartridge 10a |
| 109b | Cutout in double-sided sticky gasket 100b aligned with vent 231b of cartridge 10b |
| 109e | Cutout in double-sided sticky gasket 100f aligned with vent 231e of cartridge 10e |
| 109f | Cutout in double-sided sticky gasket 100f aligned with vent 231f of cartridge 10f |
| 113a | Cutout in gasket 100a aligned with blood conduit 259a of measurement cartridge 10a |

TABLE 1-continued

Description of Structural Features.

| Reference Numerals | Description of Structural Features |
|---|---|
| 113b | Cutout in gasket 100b aligned with blood conduit 259b of measurement cartridge 10b |
| 115a | Cutout in gasket 102a aligned with electrochemical sensor conduit 262a of calibration cartridge 20a |
| 115b | Cutout in gasket 102b aligned with electrochemical sensor conduit 262b of calibration cartridge 20b |
| 116b | Cutout in gasket 100b aligned with electrochemical sensor conduit 261b of measurement cartridge 10b |
| 117a | Cutout in gasket 102a aligned with blister window 291a of calibration cartridge 20a |
| 119a | Cutout in gasket 102a aligned with vent 233a of calibration cartridge 20a |
| 119b | Cutout in gasket 102b aligned with vent 233a of calibration cartridge 20b |
| 123b | Cutout in gasket 102b aligned with blister window 293b of calibration cartridge 20b |
| 125b | Cutout in gasket 102b aligned with blister window 295b of calibration cartridge 20b |
| 127b | Cutout in gasket 102b aligned with transfer conduit 315b of calibration cartridge 20b |
| 161f | Cutout in gasket 100f aligned with overlap between mixing chambers 464f and 465f |
| 162f | Cutout in gasket 100f aligned with overlap between mixing chambers 463f and 464f |
| 163f | Cutout in gasket 100f aligned with overlap between enlarged section 260f and mixing chamber 463f |
| 165g | Cutout in gasket 100g aligned with inlet 457g of manifold 455g of measurement cartridge 10g |
| 165h | Cutout in gasket 100h aligned with inlet 457h of manifold 455h of measurement cartridge 10h |
| 167g | Cutout in gasket 100g, which serves as air bladder communication port for connecting air bladder duct 421g with smaller section 268g of second directional valve element 68g |
| 167h | Cutout in gasket 100h, which serves as air bladder communication port for connecting air bladder duct 421h with smaller section 268h of second directional valve element 68h |
| 200a | Cap for closing sample inlet portion 57a of measurement cartridge 10a |
| 200b | Cap for closing inlet portion 57b of measurement cartridge 10b |
| 200c | Cap for closing inlet portion 57c of measurement cartridge 10c |
| 200d | Cap for closing sample storage well 51d of measurement cartridge 10d |
| 200e | Cap for closing sample storage well 51e of measurement cartridge 10e |
| 200f | Cap for closing sample storage well 51f of measurement cartridge 10f |
| 200g | Cap for closing sample storage well 51g of measurement cartridge 10g |
| 200h | Cap for closing sample storage well 51h of measurement cartridge 10h |
| 203a | Top side of cap 200a |
| 203c | Top side of cap 200c |
| 203e | Top side of cap 200e |
| 203f | Top side of cap 200f |
| 203g | Top side of cap 200g |
| 203h | Top side of cap 200h |
| 205a | Underside of cap 200a, comprising a cap flat surface 211a and a cap recess 215a |
| 205c | Underside of cap 200c, having a cap flat surface 211c and a cap recess 215c |
| 205d | Underside of cap 200d, comprising a cap flat surface 211c and a cap plunger 217d |
| 205e | Underside of cap 200e, comprising a cap flat surface 211e and a cap plunger 217e |
| 205f | Underside of cap 200f, comprising a cap flat surface 211f and a cap plunger 217f |
| 205g | Underside of cap 200g, having a cap plunger 217g |
| 205h | Underside of cap 200h, having a cap plunger 217h |
| 208e | Nest in top portion 30 of measurement cartridge 10e for receiving cap 200e when the cap is in a fully open configuration |
| 209e | Locking slot for capturing cap wing 210e for locking cap 200e in fully open configuration (2 shown in FIG. 13F) |
| 210e | Cap wing for locking cap 200e in fully open configuration during loading of sample storage well 51e (2 shown in FIG. 13F) |

TABLE 1-continued

Description of Structural Features.

| Reference Numerals | Description of Structural Features |
|---|---|
| 211a | Cap flat surface disposed at the underside 205a of cap 200a |
| 211c | Cap flat surface disposed at the underside 205c of cap 200c |
| 211d | Cap flat surface disposed at the underside 205d of cap 200d |
| 211e | Cap flat surface disposed at the underside 205e of cap 200e |
| 211f | Cap flat surface disposed at the underside 205f of cap 200f |
| 215a | Cap recess in the underside 205a of cap 200a |
| 215b | Cap recess in the underside of cap 200b |
| 215c | Cap recess in the underside 205c of cap 200c |
| 217d | Cap plunger of cap 200d |
| 217e | Cap plunger of cap 200e |
| 217f | Cap plunger of cap 200f |
| 217g | Cap plunger of cap 200g |
| 218e | Overflow trough of sample storage well 51e |
| 218f | Overflow trough of sample storage well 51f |
| 218g | Overflow trough of sample storage well 51g |
| 219e | Overflow groove of sample storage well 51e (4 shown as an example) |
| 219f | Overflow groove of sample storage well 51f (4 shown as an example) |
| 220e | Cap plunger seal of cap plunger 217e, e.g., a rubber O-ring or a molded O-ring |
| 220f | Cap plunger seal of cap plunger 217f, e.g., a rubber O-ring or a molded O-ring |
| 220g | Cap plunger seal of cap plunger 217g, e.g., a rubber O-ring or a molded O-ring |
| 221c | Gasket for cap 200c for turning cap recess 215c into a sealed chamber when the cap is in a closed configuration |
| 231b | Cartridge vent of measurement cartridge 10b |
| 231c | Cartridge vent of measurement cartridge 10c |
| 231d | Cartridge vent of measurement cartridge 10d |
| 231e | Cartridge vent of measurement cartridge 10e |
| 231f | Cartridge vent of measurement cartridge 10f |
| 231g | Cartridge vent of measurement cartridge 10g |
| 231h | Cartridge vent of measurement cartridge 10h |
| 232a | Hinge for hingedly attaching cap 200a to body of cartridge 10a |
| 232d | Hinge for hingedly attaching cap 200d to body of cartridge 10d |
| 232e | Hinge for hingedly attaching cap 200e to body of cartridge 10e |
| 233a | Cartridge vent of calibration cartridge 20a |
| 233b | Cartridge vent of calibration cartridge 20b |
| 235a | Cap latch for engaging cap 200a to body of cartridge 10a |
| 235d | Cap latch for engaging cap 200d to body of cartridge 10d |
| 236a | Cap latch catch in body of cartridge 10a for engaging cap latch 235a |
| 236d | Cap latch catch in body of cartridge 10d for engaging cap latch 235d |
| 241a | Sealing member installed in nest 243a in measurement cartridge 10a, for frictionally engaging an analyzer pump probe, which may be a flat surface or a ball having a channel for estblishing connection between an associated analyzer pump and waste receptacle 255a |
| 241c | Sealing member installed in cartridge air inlet duct 247c in measurement cartridge 10c, for frictionally engaging the outer surface of an associated analyzer pump hollow needle |
| 242a | Hole in first housing member 30a of measurement cartridge 10a, aligned with hole in sealing member 241a |
| 243a | Nest for sealing member 241a |
| 247c | Cartridge duct for housing sealing member 241c |
| 253a | Cap vent in cartridge cap 200a of cartridge 10a |
| 255a | Waste receptacle of measurement cartridge 10a |
| 256a | Waste receptacle of calibration cartridge 20a |
| 256b | Waste receptacle of calibration cartridge 20b |
| 258b | Waste receptacle of measurement cartridge 10b |
| 258c | Waste receptacle of measurement cartridge 10c |
| 258d | Waste receptacle of measurement cartridge 10d |
| 258e | Waste receptacle of measurement cartridge 10e |
| 258f | Waste receptacle of measurement cartridge 10f |
| 258g | Waste receptacle of measurement cartridge 10g |
| 259a | Blood conduit for fluidly connecting sample storage well 51a to detection chamber 261a |
| 259b | Blood conduit for fluidly connecting sample storage well 51b to detection chamber 412b (an optical chamber) |
| 259c | Blood conduit for fluidly connecting sample storage well 51c to detection chamber 261c |
| 259d | Blood conduit for fluidly connecting sample storage well 51d to detection chamber 261d |

TABLE 1-continued

Description of Structural Features.

| Reference Numerals | Description of Structural Features |
|---|---|
| 259e | Blood conduit for fluidly connecting sample storage well 51e to detection chamber (in this cartridge the detection chamber is optical chamber 412e) |
| 259f | Blood conduit for fluidly connecting sample storage well 51f to optical chamber 412f and electrochemical sensor chamber 261f |
| 260a | Enlarged section of blood conduit 259a for minimizing, mitigating, or modifying blood flow from extension 56a of bottom opening 55a of sample storage well 51a during sample loading |
| 260e | Enlarged section of blood conduit 259e for minimizing, mitigating, or modifying blood flow from extension 56e of bottom opening 55e of sample storage well 51e during sample loading |
| 260f | Enlarged section of blood conduit 259f for minimizing, mitigating, or modifying blood flow from extension 56f of bottom opening 55f of sample storage well 51f |
| 260g | Enlarged section for minimizing, mitigating, or modifying blood flow from extension 56g of bottom opening 55g of sample storage well 51g, and for fluidly connecting cutouts 105g and 165g of gasket 100g |
| 260h | Enlarged section for minimizing, mitigating, or modifying blood flow from extension 56h of bottom opening 55h of sample storage well 51h, and for fluidly connecting cutouts 105h and 165h of gasket 100h |
| 261a | Detection chamber (in this cartridge it is a biosensor chamber or an electrochemical sensor chamber) of measurement cartridge 10a |
| 261b | Biosensor or an electrochemical sensor chamber of measurement cartridge 10b |
| 261c | Detection chamber (in this cartridge it is a biosensor or an electrochemical sensor chamber) of measurement cartridge 10c |
| 261d | Detection chamber (in this cartridge it is a biosensor or an electrochemical sensor chamber) of measurement cartridge 10d |
| 261f | Electrochemical sensor chamber of measurement cartridge 10f |
| 261g | Electrochemical sensor chamber of measurement cartridge 10g |
| 262a | Electrochemical sensor chamber/conduit of calibration cartridge 20a |
| 262b | Electrochemical sensor chamber/conduit of calibration cartridge 20b |
| 264g | Larger section of first directional valve element 67g |
| 265g | Larger section of second directional valve element 68g |
| 267g | Smaller section of first directional valve element 67g |
| 268g | Smaller section of second directional valve element 68g |
| 271a | Spike for rupturing sealed blister 91a |
| 273b | Spike for rupturing the sealed blister 93b |
| 275b | Spike for rupturing the sealed blister 95b |
| 277g | Spike for rupturing the sealed blister 75g |
| 279g | Through hole in spike 277g for draining calibration fluid from ruptured blister 75g |
| 291a | Blister window in the first housing member 50a of calibration cartridge 20a for accessing sealed blister 91a |
| 292a | Through hole in spike 271a for draining calibration fluid from ruptured blister 91a |
| 293b | Blister window in the first housing member 50b of calibration cartridge 20b for accessing sealed blister 93b |
| 295b | Blister window in the first housing member 50b of calibration cartridge 20b for accessing sealed blister 95b |
| 296b | Through hole in spike 273b for draining calibration fluid from ruptured blister 93b |
| 297b | Through hole in spike 275b for draining calibration fluid from ruptured blister 95b |
| 298g | Blister window in the first housing member 30g of measurement cartridge 10g for accessing the sealed blister 75g |
| 301a | Calibration liquid conduit for receiving calibration liquid from blister 91a after the calibration liquid is released |
| 302a | Transfer conduit for transferring calibration fluid from conduit 301a to conduit 303a |
| 303a | Pre-electrochemical sensor conduit for receiving calibration fluid from transfer conduit 302a and delivering calibration fluid to electrochemical sensor conduit 262a |
| 303b | Pre-electrochemical sensor conduit for receiving calibration fluid from either transfer conduit 311b (from blister 93b) or transfer conduit 317b (from blister 95b), and delivering each calibration fluid to electrochemical sensor conduit 262b at different times |
| 305a | Post-electrochemical sensor conduit for receiving excess calibration fluid from electrochemical sensor conduit 262a |
| 305b | Post-electrochemical sensor conduit for receiving excess calibration fluid from electrochemical sensor conduit 262b |
| 307b | Blister outlet conduit for receiving calibration fluid from the ruptured blister 93b |

TABLE 1-continued

Description of Structural Features.

| Reference Numerals | Description of Structural Features |
|---|---|
| 309b | Blister outlet conduit for receiving calibration fluid from the ruptured blister 95b |
| 311b | Transfer conduit for transferring calibration fluid from conduit 307b to conduit 303b |
| 315b | Transfer conduit for transferring calibration fluid from conduit 309b to transfer conduit 317b |
| 317b | Transfer conduit for transferring calibration fluid from transfer conduit 315b to conduit 303b |
| 327b | Valve seat for mating with smaller section 71b of directional valve element 69b (see FIG. 8G in conjunction with FIG. 8H) |
| 331g | Valve seat for mating with smaller section 267g of directional valve element 67g |
| 333g | Valve seat for mating with smaller section 268g of directional valve element 68g |
| 401g | Blood conduit for fluidly connecting sample storage well 51g to optical chamber 412 |
| 401h | Blood conduit for fluidly connecting sample storage well 51h to optical chamber 412h |
| 402g | Blood conduit for fluidly connecting sample storage well 51g to electrochemical sensor chamber 261g |
| 402h | Blood conduit for fluidly connecting sample storage well 51h to electrochemical sensor chamber 261h |
| 403b | Pre-electrochemical sensor conduit in measurement cartridge 10b |
| 403g | Pre-electrochemical sensor conduit in measurement cartridge 10g |
| 403h | Pre-electrochemical sensor conduit in measurement cartridge 10h |
| 405g | Post-electrochemical sensor conduit in measurement cartridge 10g |
| 405h | Post-electrochemical sensor conduit in measurement cartridge 10h |
| 411b | First optical window of optical chamber 412b |
| 411e | First optical window of optical chamber 412e |
| 411f | First optical window of optical chamber 412f |
| 411g | First optical window of optical chamber 412g |
| 411h | First optical window of optical chamber 412h |
| 412b | Optical chamber of measurement cartridge 10b (may be a gasket cutout if the gasket thickness provides sufficient optical pathlength) |
| 412e | Optical chamber of measurement cartridge 10e (may be a gasket cutout if the gasket thickness provides sufficient optical pathlength) |
| 412f | Optical chamber of measurement cartridge 10f (may be a gasket cutout if the gasket thickness provides sufficient optical pathlength) |
| 412g | Optical chamber of measurement cartridge 10g (may be a gasket cutout if the gasket thickness provides sufficient optical pathlength) |
| 412h | Optical chamber of measurement cartridge 10h |
| 413b | Second optical window of optical chamber 412b |
| 413e | Second optical window of optical chamber 412e |
| 413f | Second optical window of optical chamber 412f |
| 413g | Second optical window of optical chamber 412g |
| 413h | Second optical window of optical chamber 412h |
| 417b | Air bladder of cartridge 10b |
| 417f | Air bladder of cartridge 10f |
| 417g | Air bladder of cartridge 10g |
| 417h | Air bladder of cartridge 10h |
| 419b | Air bladder laminate of air bladder 417b of cartridge 10b |
| 419f | Air bladder laminate of air bladder 417f of cartridge 10f |
| 419g | Air bladder laminate of air bladder 417g of cartridge 10g |
| 419h | Air bladder laminate of air bladder 417h of cartridge 10h |
| 421b | Air bladder duct for providing fluid connection between an air bladder 417b and an air bladder communication port 423b |
| 421f | Air bladder duct for providing fluid connection between an air bladder 417f and an air bladder communication port 163f |
| 421g | Air bladder duct for providing fluid connection between an air bladder 417g and an air bladder communication port 167g |
| 421h | Air bladder duct for providing fluid connection between an air bladder 417h and an air bladder communication port 167h |
| 423b | Air bladder communication port of a sample inlet portion 57b of cartridge 10b |
| 423c | Associated analyzer pump communication port of sample inlet portion 57c of cartridge 10c |
| 427b | One of one or more female cartridge tracks for guiding linear motion of cap 200b. In this non-limiting example, two female tracks are shown. In some embodiments, the one or more tracks may be configured as male cartridge tracks. Some embodiments may comprise one male and one female track, and if desired, the cap motion may be non-linear (i.e. curved). |
| 431g | Blister outlet conduit for receiving calibration fluid from the ruptured blister 75g |

TABLE 1-continued

Description of Structural Features.

| Reference Numerals | Description of Structural Features |
|---|---|
| 433g | Transfer conduit for transferring calibration fluid from conduit 431g to pre-electrochemical sensor conduit 403g |
| 435g | Conduit for connecting conduit 402g to conduit 403g |
| 451c | Hydrophobic insert disposed close to the bottom opening 55c of the sample storage well 51c, for providing means for minimizing, mitigating, or modifying blood flow out of the sample storage well 51c |
| 453c | Nest in second housing member 40c of cartridge 10c for installing hydrophobic insert 451c |
| 455g | Manifold of extension 56g of the bottom opening 55g of sample storage well 51g of cartridge 10g, having an inlet 457g |
| 455h | Manifold of extension 56h of the bottom opening 55h of sample storage well 51h of cartridge 10h |
| 457g | Inlet of manifold 455g |
| 457h | Inlet of manifold 455h |
| 463f | First mixing chamber of measurement cartridge 10f |
| 464f | Second mixing chamber of measurement cartridge 10f |
| 465f | Third mixing chamber of measurement cartridge 10f |
| 467b | Blood shunt in measurement cartridge 10b |
| 467f | Blood shunt in measurement cartridge 10f |
| 470h | Overlap between blood conduit 402h and pre-electrochemical sensor conduit 403h of measurement cartridge 10h |

Overview of Calibration Cartridges 20a and 20b as Non-Limiting Examples

U.S. Pat. No. 5,096,669 to Lauks discloses a POCT cartridge for measuring blood gases and electrolytes in whole blood. The cartridge includes a preassembled calibration liquid (also referred to as calibration fluid) blister and a spike for rupturing the blister to release the calibration fluid, which is used to perform a one-point calibration of some of the electrochemical sensors in each cartridge. A screw and wedge mechanism are used to push the blister against the spike and force the released fluid into the electrochemical sensor chamber. The cartridge also comprises a hinged cap for covering the sample inlet after depositing sample in a sample well, and the cartridge does not include an optical chamber.

U.S. Pat. No. 7,094,330 to Lauks discloses another POCT cartridge for measuring blood gases and electrolytes in whole blood. This cartridge also includes a calibration fluid blister for performing a one-point calibration of some of the electrochemical sensors in each cartridge. The method of releasing the calibration fluid includes a plug for delaminating a section of the calibration fluid blister (a breakable seal 230). Also disclosed is a fill port 221 and a vent 222 for filling the calibration fluid blister. After filling the calibration fluid, a seal element 202 is laminated to seal off ports 221 and 222. A planar element comprising a plug 282 (for delaminating breakable seal 230) and a pin element 281 compresses the calibration fluid chamber 220 to release the calibration fluid. Blood must be loaded from a syringe, and the blood ejected from the syringe displaces the calibration fluid from the sensors. The syringe remains screwed to the cartridge inlet during measurement, therefore there is no requirement for a cap, and the cartridge does not include an optical chamber.

Figure 1A:
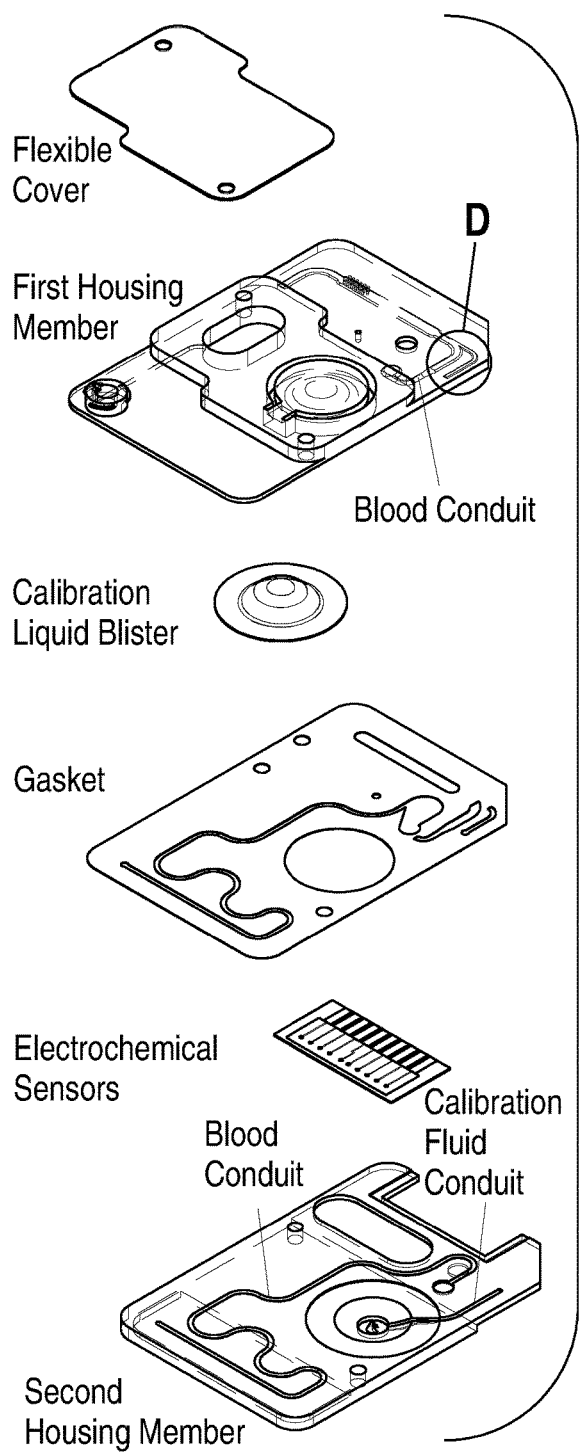
FIG. 1A (Prior Art) is an exploded view illustrating a version of a cartridge comprising an optical chamber, electrochemical sensors, and a blister containing calibration liquid for calibrating at least one of the electrochemical sensors.
Figure 1B:
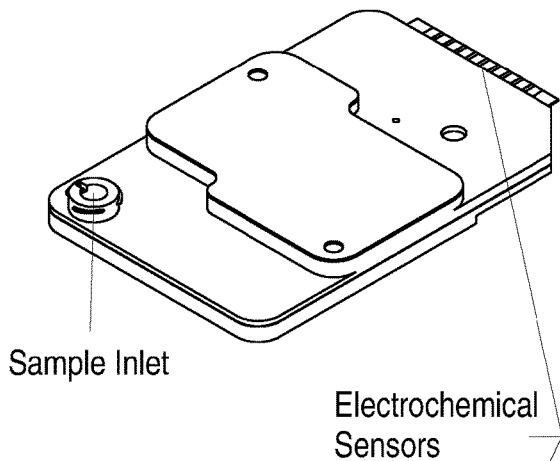
FIG. 1B (Prior Art) is a perspective top view of the cartridge illustrated in FIG. 1A, with sample inlet that works in conjunction with a screw cap.
Figure 1C:
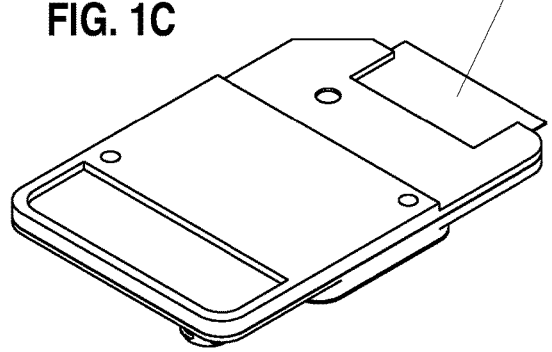
FIG. 1C (Prior Art) is a perspective bottom view of the cartridge illustrated in FIG. 1A.

U.S. Pat. No. CA 2,978,737 to Samsoondar discloses another POCT cartridge for measuring blood gases, and electrolytes. Also disclosed in U.S. Pat. No. CA 2,978,737 is an optical chamber for performing spectroscopic measurement, for measuring CO-oximetry and bilirubin. Details of an example of the cartridges disclosed in U.S. Pat. No. CA 2,978,737 is provided in FIGS. 1A-1D of the present application. Capillary action is required to draw the blood sample through the optical chamber, up to an enlarged chamber outside the optical chamber. Calibration liquid from a blister is provided to perform a one-point calibration of some of the electrochemical sensors. Pressure on the dome portion of the blister pushes the blister against a spike, causing the bottom of the blister to rupture and release calibration fluid (may also be referred to as calibration liquid), and further pressure pushes released calibration liquid into the electrochemical sensor chamber. After a one-point calibration is performed, pressurized air from an air bladder pushes the blood into the electrochemical sensor chamber, displacing the calibration liquid. A screw cap is required to close the sample inlet. FIG. 1A illustrates how calibration liquid is able to flow to the top of the second housing member. A screw cap disclosed in Pat. No. CA 2,978,737 is not user friendly, and more user-friendly capping systems are needed. There is also a need to reduce the cost of POCT single-use cartridges, and at the same time, increase the test menu.

A major limitation of POCT blood gas and electrolyte systems disclosed in U.S. Pat. Nos. 5,096,669 and 7,094,330 is that their measurement technique is based on electrochemical sensors and therefore cannot measure CO-oximetry or bilirubin, which can only be measured by spectroscopy. Oxygen is carried in the blood in two forms: (1) Dissolved in plasma and RBC water, which accounts for only 1-2% of the total blood oxygen content; and (2) Reversibly bound to hemoglobin, which accounts for about 98% of the total blood oxygen content. Partial pressure of oxygen ($pO_2$) is proportional to the quantity of oxygen dissolved in blood and is related to $SO_2$ (hemoglobin saturated with oxygen) through a sigmoidal curve ($SO_2$ plotted on the Y-axis and $pO_2$ plotted on the X-axis) referred to as the Oxygen-Hemoglobin Dissociation Curve. Measurement cartridges disclosed in U.S. Pat. Nos. 5,096,669, and 7,094,330 estimate $SO_2$ from measured $pO_2$, and estimate Hemoglobin (Hb) from measured Hematocrit. The Hb could be underestimated, possibly leading to unnecessary blood transfusion. CO-oximetry is the gold standard for measuring $SO_2$ because it actually measures % Oxy-Hb and % Deoxy-Hb, as well as % non-functional Hb like Met-Hb and Carboxy-Hb. A finger clip-on device referred to as a Pulse Oximeter is used in the ICU to measure $SO_2$ by a technique referred to as Pulse Oximetry, which may be inaccurate in the presence of elevated non-functional Hb. Measurement of Carboxy-Hb is essential for detecting carbon monoxide poisoning and monitoring treatment. Carbon monoxide poisoning could occur during excessive smoke inhalation. Measurement of Met-Hb is essential for detecting and treating elevated levels of Met-Hb, which could occur after ingestion of certain chemicals, in patients with certain enzyme deficiency, and in babies treated with nitric oxide for respiratory distress.

The inclusion of a calibration liquid blister within the test cartridges disclosed in U.S. Pat. Nos. 5,096,669, 7,094,330 and CA U.S. Pat. No. 2,978,737 adds significant cost to the cartridges, precluding their use in underdeveloped countries, and the calibration liquid in the blister can only perform a one-point calibration, and assumes that the slope of the calibration equation did not change. WO/2022/056631 discloses simpler and less expensive POCT blood gas and electrolyte cartridges, which can perform more than just a one-point calibration. POCT cartridges that can also provide CO-oximetry and bilirubin without adding any significant cost to the cartridges, are also disclosed in WO/2022/056631. Bilirubin is a waste product of hemoglobin degradation, and elevated levels cause a condition known as jaundice. More than half of healthy neonates develop neonatal jaundice within days of birth because the baby's liver has not developed sufficiently to eliminate bilirubin from the blood. Babies with neonatal jaundice can easily be treated successfully, but if left untreated, neonatal jaundice could cause permanent brain damage and deafness.

Figure 5A:
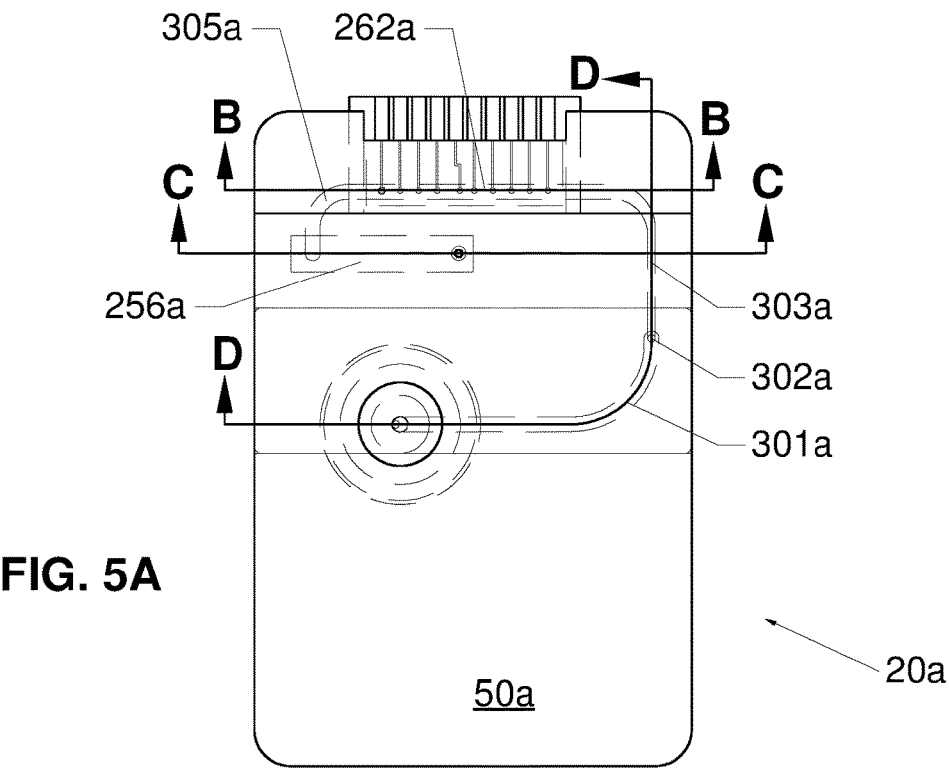
FIG. 5A is a top view of the calibration cartridge 20a shown in FIG. 4A.
Figure 5B:
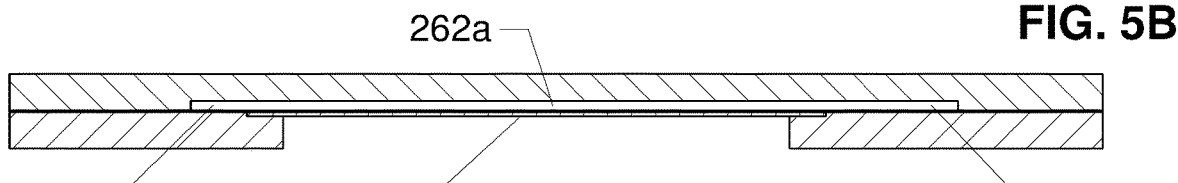
FIG. 5B is an enlarged cross-sectional view through the calibration cartridge 20a shown in FIG. 5A along line B-B.
Figure 5C:
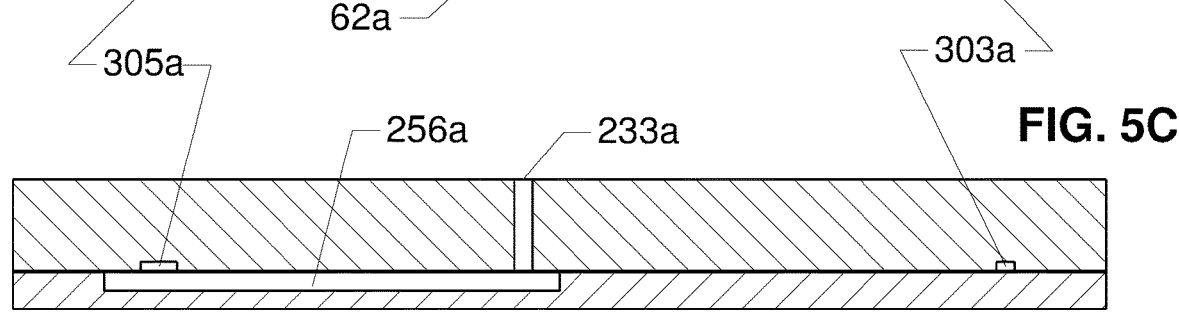
FIG. 5C is an enlarged cross-sectional view through the calibration cartridge 20a shown in FIG. 5A along line C-C.

Two embodiments of calibration cartridges are provided: Calibration cartridge 20a is illustrated collectively in FIGS. 4A-5D, and calibration cartridge 20b is illustrated collectively in FIGS. 6A-8H. Description of the structural features is provided in Table 1. The major difference between the two calibration cartridges is that calibration cartridge 20a comprises a single calibration liquid blister 91a, illustrated in FIG. 4A, an exploded view of the calibration cartridge, and FIG. 5D, an enlarged cross-sectional view of the calibration cartridge along lines D-D shown in FIG. 5A. Calibration cartridge 20a may be used for a single-point calibration. Similar cartridges may also be used for monitoring quality control of the associated analyzer, since the quantities of the analytes are known. In contrast, calibration cartridge 20b comprises two sealed calibration liquid blisters 93b and 95b, illustrated in FIG. 6A, an exploded view of the calibration cartridge, and FIGS. 7D and 7E, enlarged cross-sectional views of the calibration cartridge along lines D-D and E-E respectively, shown in FIG. 7A. Calibration cartridge 20b, which comprises an electrochemical sensor array 62b (see FIGS. 6A-6C) may be used to perform two-point calibration to calibrate electrochemical sensor array 61b (see FIGS. 9A, 9F and 9G) installed in measurement cartridge 10b. In this example of a measurement cartridge 10b, the electrochemical sensor array 61b is similar to the electrochemical sensor array 62b installed in calibration cartridge 20b, and preferably belong to the same manufactured batch.

As an alternative to a calibration cartridge comprising two sealed calibration liquid blisters for performing two-point calibration, two calibration cartridges comprising a single calibration liquid blister may be used, wherein each of the two calibration liquid blisters in the two calibration cartridges are located in the same position, and the liquid composition of the two calibration liquid blisters are different. An advantage to this alternative is that the analyzer only requires a single rupture mechanism. If the single rupture mechanism is a stepper motor actuator that pushes against the blister, the same actuator may also be used to activate an air bladder, if the cartridge comprises an air bladder. Further, multipoint calibration may be performed using more that two calibration cartridges, each calibration cartridge comprising a single calibration liquid blister, wherein the single calibration liquid blisters in the more than two calibration cartridges are located in the same position, and the liquid composition of each of the single calibration liquid blisters is different. In the case of more than one calibration cartridges, the calibration liquid in each calibration cartridge is tested sequentially.

Other measurement cartridges that may be calibrated with calibration cartridges 20a or 20b include measurement cartridge 10a (shown in FIGS. 2A-3E), measurement cartridge 10c (shown in FIGS. 10A-10G), measurement cartridge 10d (shown in FIGS. 11A-12D), 10f (shown in FIGS. 16A-17D), and measurement cartridge 10h (shown in FIGS. 22A-23D). Neither of these cartridges include a calibration liquid blister, and they all contain electrochemical sensor arrays 61a, 61c, 61d, 61f, and 61h respectively. Calibration cartridge 20b may be used to perform periodic two-point calibration of measurement cartridge 10g; each measurement cartridge 10g is capable of performing one-point calibration because measurement cartridge 10g comprises one sealed blister 75g.

Calibration 20b, measurement cartridge 10b and analyzer 80 are used as examples to illustrate a system shown in FIGS. 18A-18C. FIG. 18A is a perspective top view of an analyzer 80 and the calibration cartridge 20b, not yet inserted in the receptor 14 of analyzer 80. FIG. 18B is a perspective top view of the analyzer 80 shown in FIG. 18A and the measurement cartridge 10b, not yet inserted in the receptor 14 of analyzer 80. FIG. 18C is a perspective top view of the analyzer 80 and the measurement cartridge 10b shown in FIG. 18B, with the cartridge inserted in the receptor 14 of the analyzer 80 for sample measurement. Prior to insertion of the measurement cartridge 10b, calibration cartridges 20a or 20b comprising electrochemical sensor arrays 61a and 61b respectively, and may be use to calibrate one or more electrochemical sensors of electrochemical sensor array 61b of measurement cartridge 10b illustrated collectively in FIGS. 9A-9G.

Figure 1D:
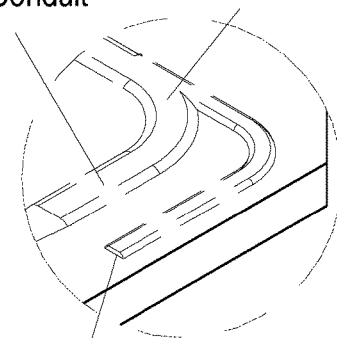
FIG. 1D (Prior Art) is a detailed view of detail D shown in FIG. 1A, illustrating that the calibration liquid conduit is not closed (i.e., it is open to an influx of blood)
Figure 5D:
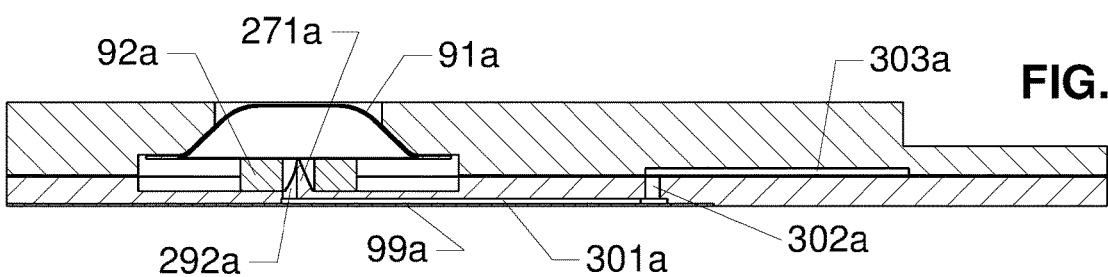
FIG. 5D is an enlarged cross-sectional view through the calibration cartridge 20a shown in FIG. 5A along line D-D.
Figure 11A:
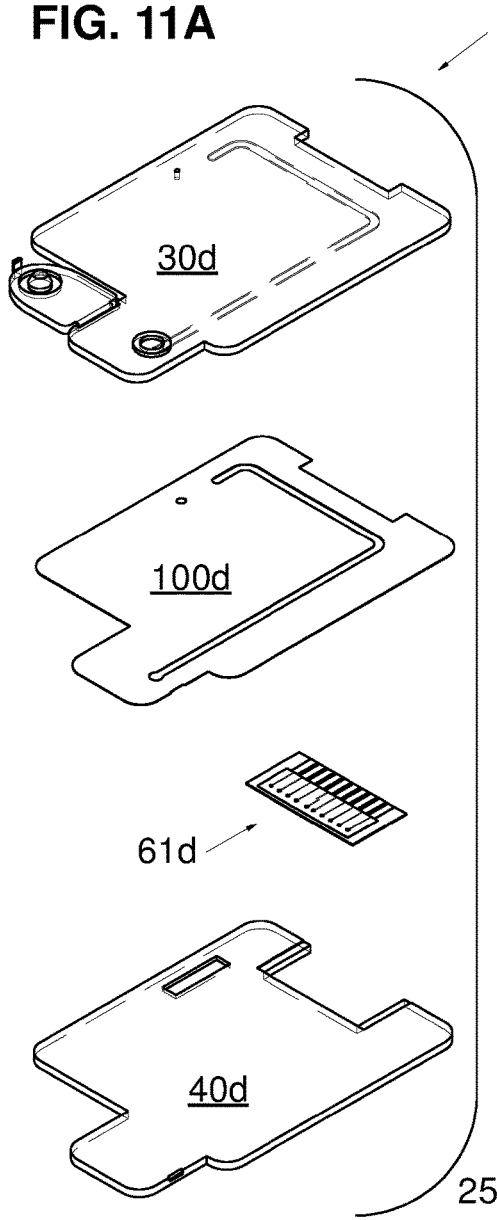
FIG. 11A is an exploded perspective top view of a measurement cartridge 10d for measuring at least one property of blood, according to a fourth embodiment of a measurement cartridge.
Figure 11B:
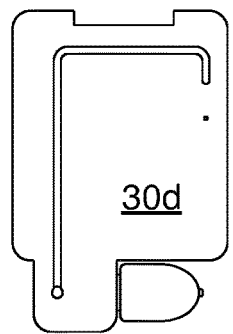
FIG. 11B is a bottom view of the first housing member 30d of the measurement cartridge shown in FIG. 11A.
Figure 11C:
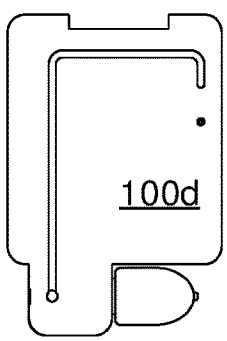
FIG. 11C is the bottom view of the first housing member 30d of the measurement cartridge shown in FIG. 11B, overlaid by and in alignment with a gasket 100d shown in FIG. 11A.
Figure 11D:
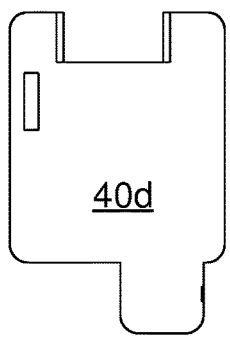
FIG. 11D is a top view of the second housing member 40d of the measurement cartridge shown in FIG. 11A.
Figure 11E:
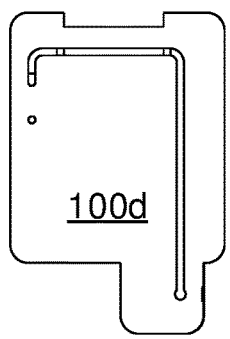
FIG. 11E is the top view of the second housing member 40d shown in FIG. 11D, overlaid by and in alignment with the gasket 100d shown in FIG. 11A.
Figure 11F:
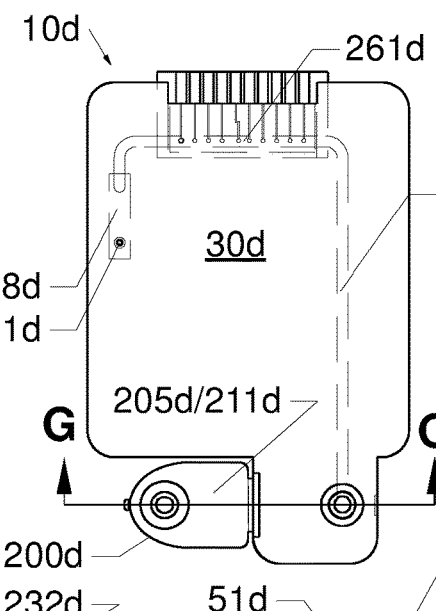
FIG. 11F is a top view of the measurement cartridge 10d shown in FIG. 11A, in an open configuration.
Figure 11G:
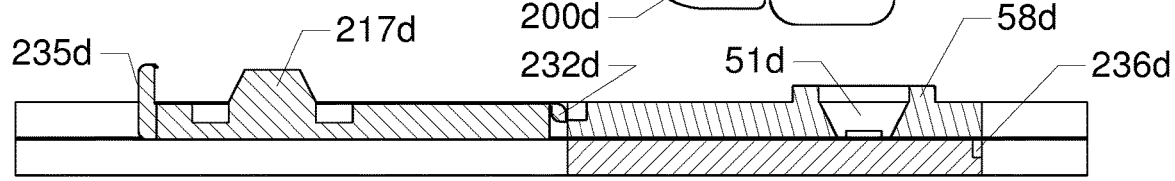
FIG. 11G is an enlarged cross-sectional view through the measurement cartridge 10d shown in FIG. 11F along line G-G.
Figure 12A:
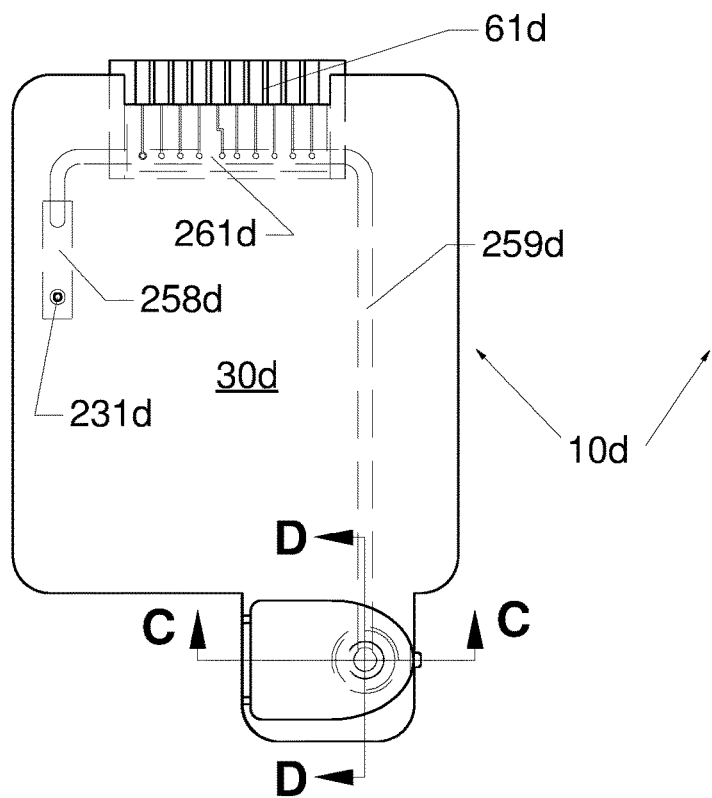
FIG. 12A is a top view of the measurement cartridge 10d shown in FIG. 11A, in a closed configuration.
Figure 12B:
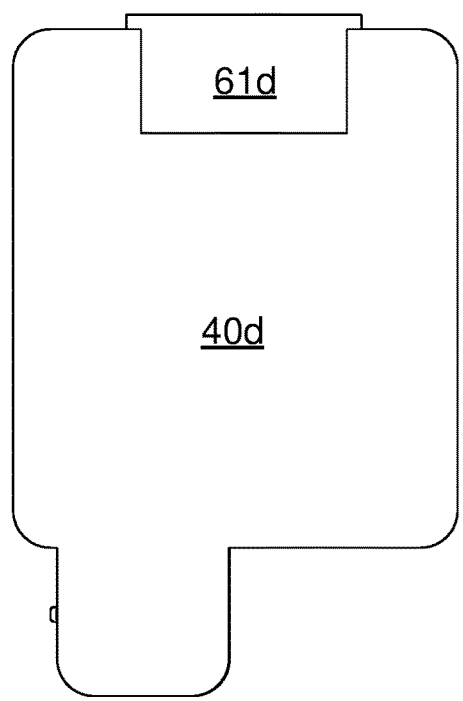
FIG. 12B is a bottom view of the measurement cartridge 10d shown in FIG. 11A.
Figure 12C:
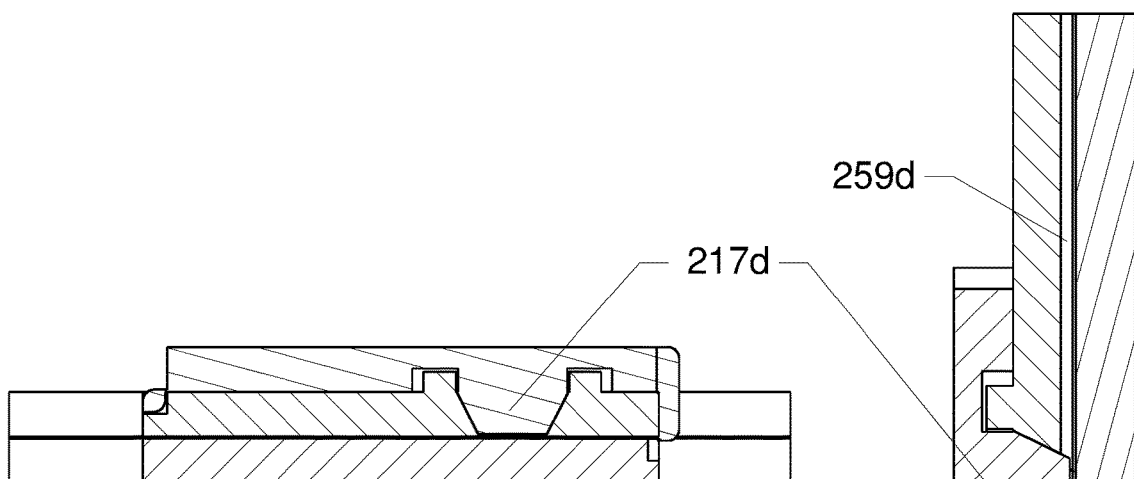
FIG. 12C is an enlarged cross-sectional view through the measurement cartridge 10d shown in FIG. 12A along line C-C.
Figure 12D:
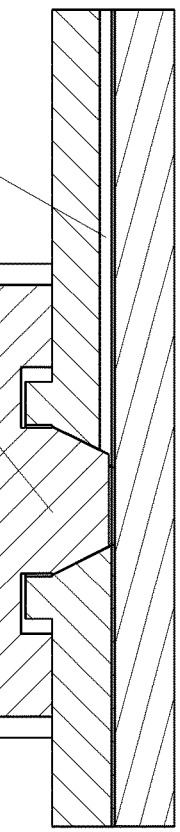
FIG. 12D is an enlarged cross-sectional view through the measurement cartridge 10d shown in FIG. 12A along line D-D.

Calibration of one or more electrochemical sensors in electrochemical sensor array 61b of measurement cartridge 10b, using calibration cartridge 20a is described: Force from an attachment to a stepper motor, as a non-limiting example, in an associated analyzer is applied to the top portion (dome portion) of the blister 91a via blister window 291a (see FIG. 4A), pushing the bottom portion (flat portion) of the blister against spike 271a and simultaneously compressing compressible blister support 92a (see FIG. 5D). The spike 271a ruptures the blister releasing calibration liquid into calibration liquid conduit 301a via through hole 292a in spike 271a. Conduit 301a is exposed in FIG. 4G by removing laminate 99a. In other embodiments, for example the prior art shown in FIG. 1A, the spike does not have a through hole, and the calibration liquid flows towards a hole in the gasket and makes its way to the electrochemical sensors, and such flow is considered to be within the scope of the present application. In the prior art, the calibration liquid merges with the blood conduit as shown in FIG. 1D. Referring to FIG. 5D, calibration liquid is transferred from conduit 301a to pre-electrochemical sensor conduit 303a via transfer conduit 302a. Excess calibration liquid leaving the electrochemical sensor conduit 262a (see FIG. 5A) enters conduit 305a and subsequently into a waste receptacle 256a. Cartridge vent 233a (see FIG. 5C) provides an air escape route.

Although calibration cartridges 20a and 20b are both shown to comprise first housing members 50a and 50b attached to second housing members 60a and 60b by double-sided sticky gaskets 102a and 102b respectively, calibration cartridges comprising different housing members in terms of design and number of components are considered to be within the scope of the present application.

Calibration cartridge 20b shown collectively in FIGS. 6A-8H, functions in a similar manner to calibration cartridge 20a, and the calibration liquid blisters are ruptured at different times in order to generate two separate set of electrical signals corresponding to the analyte concentrations. Some embodiments do not include optional directional valve element 69b, which allows either blister to be ruptured first, provided that the associated analyzer is programmed to direct which blister is ruptured first. In this example, the directional valve element may be a flappable polymeric element having a larger section 73b for constraining element 69b, and a smaller section 71b that is flappable to seal off a first conduit while the liquid flows through the second conduit. For example, as illustrated in FIG. 7D, when liquid from blister 95b flows through conduits 317b via conduits 309b and 315b in that order, the flap 71b closes off conduit 311b, which is in fluid communication with blister 93b. On the other hand, when liquid flows through conduit 311b from blister 93b via conduit 307b, the flap 71b is pushed upwards and closes off conduit 317b as the flap 71b is pushed against valve seat 327 shown in FIG. 8G. Operation of directional valve element 69b is illustrated collectively in FIGS. 8A-8H, in conjunction with the description of structural features provided in Table 1. Although no more than two blisters are illustrated in the drawings, any number of blisters are considered to be within the scope of calibration cartridges. An air bubble automatically inserted between the two different calibration liquids may be used to keep the liquids separate, and the air bubble is also effective in removing residues of the first calibration liquid, as the second calibration liquid flows over the electrochemical sensor array.

Overview of Measurement Cartridges 10a, 10b and 10c as Non-Limiting Examples

A first embodiment of a measurement cartridge 10a is illustrated collectively in FIGS. 2A-3E. Description of the structural features is provided in Table 1. Measurement cartridge 10a comprises an electrochemical sensor array 61a that is similar to electrochemical sensor arrays 62a and 62b in calibration cartridges 20a and 20b respectively. Unlike the calibration cartridges, measurement cartridges are designed to receive a blood sample for measurement. Measurement cartridge 10a is illustrated as a first housing member 30a attached to a second housing member 40a by a double-sided sticky gasket 100a, and comprises a hinged cap 200a, adjustable from a first position to a second position. In the first position, illustrated in FIGS. 2F and 3A, the sample storage well 51a is configured to receive a blood sample via top opening 53a. In the second position, the hinged cap 200a is closed over sample storage well 51a. Hinged cap 200a comprises a cap recess 215a disposed at the underside 205a of cap 200a, and a cap vent 253a. Gravity allows the blood to flow to the bottom opening 55a, and depending on the wettability or hydrophilicity of the material lining the sample storage well 51a and the extension 56a of bottom opening 55a of sample storage well 51a, blood may flow up to cutout 105a in gasket 100a. Due to the small size of gasket cutout 105a and relatively large size of enlarged section 260a of blood conduit 259a (see FIG. 3F), blood flow out of gasket cutout 105a is mitigated, except when the blood is subjected to negative pressure, via sealing member 241a installed in nest 243a in measurement cartridge 10a, for frictionally engaging an analyzer pump probe. Instead of depending on gravity to pull a drop of blood into the sample storage well from a pinprick of the skin of a patient, the bottom of the sample storage well may be corona treated to make the bottom surface more wettable. It was observed that when the bottom of the sample storage well is hydrophobic, the blood tends to cling to the skin until the drop of blood becomes large enough, allowing the force of gravity to overcome the attraction between the blood and the patient's skin. A person skilled in the art would understand that there are alternatives to corona treatment for making a surface hydrophilic, for example, overmolding the bottom of the sample storage well with a hydrophilic plastic if the adjacent parts of the cartridge is made by injection molding using a hydrophobic plastic. Overmolding is less expensive technique in injection molding than installing an insert of a different material.

The pump probe may be a flat surface or a ball having a channel for establishing connection between an associated analyzer pump and waste receptacle 255a. After the sample storage well 51a receives blood sample, hinged cap 200a is moved from the first position to the second position shown in FIG. 3B. Cap latch 235a and catch 236a keeps the cartridge in the closed configuration, and the cartridge in the closed configuration is placed in an associated analyzer receptor, for example receptor 14 in analyzer 80 illustrated in FIGS. 18A-18C. Analyzers may comprise receptors that swing out or slide out, and after the cartridge is placed in the receptor, it swings in or slides in. In the associated analyzer, a sealing member 241a installed in nest 243a in measurement cartridge 10a (see FIG. 3C), frictionally engages with a pump probe from the associated analyzer. After the analyzer pump is activated, the sample is sucked into the detection chamber 261a via a blood conduit 259a. Any excess blood is trapped in the waste receptacle 255a. Cap vent 253a exposes the blood in the sample storage well to atmospheric pressure, for facilitating blood flow.

Blood conduit in cartridge 10a is shown as the combination of a groove 259a in the first housing member 30a and a cutout 113a in gasket 100a, but in order to minimize sample requirement, the blood conduit may only be the gasket cutout 113a, for example 259e shown in FIG. 13C regarding cartridge 10e.

A third embodiment of a measurement cartridge 10c is illustrated collectively in FIGS. 10A-10G. Compared with measurement cartridge 10a discussed previously, the blood flow mechanism in measurement cartridge 10c is reversed. This is accomplished by replacing the cap vent 253a shown in FIG. 3D with a cartridge vent 231c shown in FIGS. 10B and 10D, and setting the associated analyzer pump to exert positive pressure. In the closed configuration, cap recess 215c creates a closed chamber and air pressure from the associated analyzer pump, via pump communication port 423c (see FIGS. 10E and 10F). In this example, sealing member 241c installed in cartridge air inlet duct 247c in measurement cartridge 10c (see FIG. 10G) is frictionally engaged with the outer surface of an associated analyzer pump hollow needle, which is another example of pump engagement. Another difference in measurement cartridge is the inclusion of a hydrophobic insert 451c disposed close to the bottom opening 55c of the sample storage well 51c, for providing means for minimizing, mitigating, or modifying blood flow out of the sample storage well 51c. The hydrophobic insert 451c located in a nest 453c in the second housing member 40c is illustrated in FIGS. 10E and 10F, viewed in conjunction with FIG. 10D.

A second embodiment of a measurement cartridge 10b is illustrated collectively in FIGS. 9A-9G. Compared with measurement cartridge 10c discussed previously, the positive pressure used to push the blood sample from the top portion 53b of the sample storage well 51b is not from an associated analyzer pump but instead is generated from an air bladder 417b, illustrated in FIGS. 9A and 9F. A second difference is that instead of a hinged cap, the cap 200b slides along tracks 427b, illustrated in FIG. 9F. The sliding cap 200b also comprises a recess 215b and a sample inlet portion 57b, illustrated in FIG. 9A. A third difference is the inclusion of an optical chamber 412b, enclosed by a first optical window 411b and a second optical window 413b. Although the optical chamber is located between the sample storage well 51b and the electrochemical sensor chamber 261b, the optical chamber may be located downstream of the electrochemical sensor chamber 261b. Moreover, instead of having the two detection chambers (optical and electrochemical sensor) arranged in series, they may also be arranged in parallel, for example, see measurement cartridge 10g illustrated collectively in FIGS. 19A-21J and measurement cartridge 10h illustrated collectively in FIGS. 22A-23D.

Measurement cartridges like 10a, 10b and 10c were previously discussed in PCT/CA2020/051254 filed Sep. 18, 2020, to which the present application claims the benefit of. Other relevant cartridges discussed in PCT/CA2020/051254 and not repeated in this application for the sake of brevity, include measurement cartridges that slide about a pivotal hinge instead of sliding along tracks.

Overview of Measurement Cartridges 10d and 10e as Non-Limiting Examples

A fourth embodiment of a measurement cartridge 10d is illustrated collectively in FIGS. 11A-12D. Description of the structural features is provided in Table 1. The hinged cap 205d in measurement cartridge 10d comprises a cap plunger 217d, illustrated in FIG. 11G and viewed in conjunction with FIG. 11F, with the hinged cap 205d in a first position and the sample storage well 51d in an open configuration. Illustrated in FIGS. 12C and 12D, viewed in conjunction with FIG. 12A, the hinged cap 205d is adjusted to second position, wherein the sample storage well is in a closed configuration. In the open configuration, the sample storage well 51d is configured to receive a blood sample. Depending on the hydrophobicity of the blood conduit 259d, some blood may or may not flow from the sample storage well 51d into the blood conduit 259d. If desirable, means for minimizing, mitigating, or modifying blood flow out of the sample storage well 51d, as described for measurement cartridges 10a and 10c may be included in the design of measurement cartridge 10d. During the time when the hinged cap 205d is moved from the first position to the second position, the cap plunger displaces blood from the sample storage well 51d into the detection chamber 261d via a blood conduit 259d. Air pressure in the detection chamber 261d is relieved by cartridge vent 231d. Any excess blood is contained in the waste receptacle 258d. In cartridge 10d, neither air pressure (positive or negative) nor capillary action is required to move blood from the sample storage well 51d to the detection chamber 261d. The advantages of a measurement cartridge having a cap comprising a plunger cap like 217d are: 1) Simpler less expensive measurement cartridge; 2) More options in plastics used for manufacture of measurement cartridge; and 3) Simpler less expensive associated analyzer. If injection molding is used to construct the cartridge parts, the plunger cap may be an overmolding element made from a different material. For example, the plunger and O-ring may be overmolded as a single element using a thermoplastic elastomer (TPE), and the rest of the cartridge may be constructed using a harder and more transparent plastic, for example polyethylene terephthalate (PET).

A fifth embodiment of a measurement cartridge 10e illustrated collectively in FIGS. 13A-14F is similar to cartridge 10d. A first difference is that the plunger 217e illustrated in FIG. 14D, viewed in conjunction with FIGS. 14C and 14E, is cylindrical comprising an O-ring 220e. The O-ring may be a rubber slip-on O-ring or plastic, molded as an integral part of the plunger 217e. A second difference is that the detection chamber is an optical chamber 412e enclosed by a first optical window 411e and a second optical window 413e. A third difference is the inclusion of an enlarged section 260e of blood conduit 259e for minimizing, mitigating, or modifying blood flow from extension 56e of bottom opening 55e of sample storage well 51e during sample loading, as was described for measurement cartridge 10a. A fourth difference is the inclusion of overflow groove 219e of sample storage well 51e (4 shown as an example), and an overflow trough 218e of sample storage well 51e for containing any excess blood. After the cartridge is adjusted from an open configuration to a closed configuration, the O-ring remains located in the groove at the gasket, preventing the plunger from rebounding. With the overflow grooves 219e and the enlarged section 260e, gasket cutout 105e, the volume of blood displaced by the plunger 217e is substantially reproducible from cartridge to cartridge. The reproducibility of the volume of blood displaced by the plunger 217e also depends on the wettability of the sample storage well surface and grooves 219e of the sample storage well. Some embodiments of cartridge body constructed from hydrophobic material may comprise a sample storage well as an insert, wherein the insert is constructed from a more hydrophilic or wettable material than the rest of the cartridge body. If the surfaces of the sample storage well is too hydrophobic, the blood sample may not fill the sample storage well completely, and the overflow groves 219e may not function properly, producing a bulging meniscus of the blood sample in the well. As an alternative to the enlarged section 260e and gasket cutout 105e, a hydrophobic insert (e.g., 451c in FIGS. 10E and 10F) may be installed at the outlet 55e of the sample storage well 51e, as illustrated in FIG. 10F of cartridge 10c.

The sample storage capacity of the sample storage well 51e may be altered by changing the diameter of the well 51e. The sample storage capacity of the sample storage well 51e may also be altered without changing the diameter of the well 51e, by increasing or decreasing the depth of the well 51e. As shown in FIG. 14D, the top of the sample storage well is aligned with the top surface of the first housing member 30e, and as shown in FIG. 17B regarding cartridge 10f, the top of the sample storage well is above the top surface of the first housing member 30f. The top of the sample storage well may also be below the top surface of the first housing member of a measurement cartridge. In order to reduce dead volume, the length of the plunger 217e is sufficiently long to reach the bottom of the sample storage well 51f. In order to avoid crushing red blood cells, a small space is maintained between the bottom of the plunger 217e and the bottom of the sample storage well 51e, by designing the cap 200e so that the cap flat surface 211e makes contact with the top surface of the first housing member 30e when the cap 200e is adjusted from the first position to the second position.

Overview of Measurement Cartridges 10f as a Non-Limiting Example

A sixth embodiment of a measurement cartridge 10f is illustrated collectively in FIGS. 16A-17D. Description of the structural features is provided in Table 1. Shown in FIG. 16A is an exploded perspective top view of the measurement cartridge 10f for measuring at least one property of blood, comprising a first housing member 30f, a second housing member 40f, and a double-sided sticky gasket 100f for attaching housing members 30f and 40f. Shown in FIG. 16B is a bottom view of the first housing member 30f of the cartridge shown in FIG. 16A, and shown in FIG. 16C is the bottom view of the first housing member 30f of the cartridge shown in FIG. 16B, overlaid by and in alignment with a gasket 100f shown in FIG. 16A. Shown in FIG. 16D is a top view of the second housing member 40f of the cartridge shown in FIG. 16A, and shown in FIG. 16E is the top view of the second housing member 40f shown in FIG. 16D, overlaid by and in alignment with the gasket 100f shown in FIG. 16A.

FIG. 16F illustrates a perspective top view of the cartridge 10f in the assembled state, showing the upper surface of the cartridge body, with cap 200f adjusted to a first position, whereby the sample storage well 51f is in an open configuration for receiving a blood sample. FIG. 16G illustrates a perspective bottom view of the cartridge 10f showing the lower surface of the cartridge body. After receiving the blood sample, the cap is adjusted from the first position to a second position as shown in FIG. 17A, whereby the sample storage well 51f is in a closed configuration. The O-ring 220f remains located in the groove at the gasket, preventing the plunger from rebounding. Although the O-ring groove is shown to be at the gasket interface with the first housing member 30f and second housing member 40f, the groove may be at other locations, and the position of the O-ring adjusted in a corresponding manner. With overflow grooves 219f, enlarged section 260f, and gasket cutout 105f (see FIG. 17D), the volume of blood displaced by the plunger 217f is substantially reproducible from cartridge to cartridge. When the cap 200f is adjusted from a first position to a second position, a metered volume of blood is displaced from the sample storage well 51f into a mixing chamber 463f (see FIGS. 16D and 17C), which may contain predetermined amounts of one or more dry reagents, for example without any limitations, a hemolyzing agent. Turbulence further mixes the metered volume of blood and the predetermined amount(s) of reagent(s) as the mixture or altered blood is moved from the mixing chamber 463f to mixing chamber 464f, to mixing chamber 465f, into the blood conduit 259f, and finally into the detection chambers 412f (optical) and 261f (electrochemical). Cartridge 10f comprises both an optical chamber 412f enclosed by a first optical window 411f and a second optical window 413f, and an electrochemical sensor chamber 261f (see FIGS. 17A and 17B). Some measurement cartridges do not include a mixing chamber and may contain one or more dry reagents in any section of the blood flow conduit between the top portion of the sample storage well and the detection chamber, and the means for mixing the blood and the one or more dry reagents includes the one or more reagents, blood flow, and dissolution of the one or more reagents when the blood flows over the one or more reagents.

Movement of altered blood from the mixing chamber 463f is facilitated by pressurized air from air bladder 417f via air bladder duct 421f and air bladder communication port 163f. Therefore, movement of unaltered blood and movement of altered blood are two separate steps, utilizing the plunger 217f and the air bladder 417f respectively. Optional use of an associated analyzer pump instead of an air bladder 417f was previously discussed.

Illustrated in FIG. 17B is an enlarged cross-sectional view through the measurement cartridge 10f shown in FIG. 17A along line B-B. Shown in FIG. 17C is a detailed view of detail C shown in FIG. 17B, and shown in FIG. 17D is a detailed view of detail D shown in FIG. 17C.

Overview of Measurement Cartridges 10g and 10h as Non-Limiting Examples

A seventh embodiment of a measurement cartridge 10g is illustrated collectively in FIGS. 19A-21J, and an eighth embodiment of a measurement cartridge 10h is illustrated collectively in FIGS. 22A-23D, for measuring at least one property of blood. Description of the structural features is provided in Table 1. Measurement cartridge 10g is very similar to measurement cartridge 10h; a major difference is that cartridge 10g comprises a calibration fluid blister 75g for performing a 1-point calibration (i.e., offset correction).

Figure 19A:
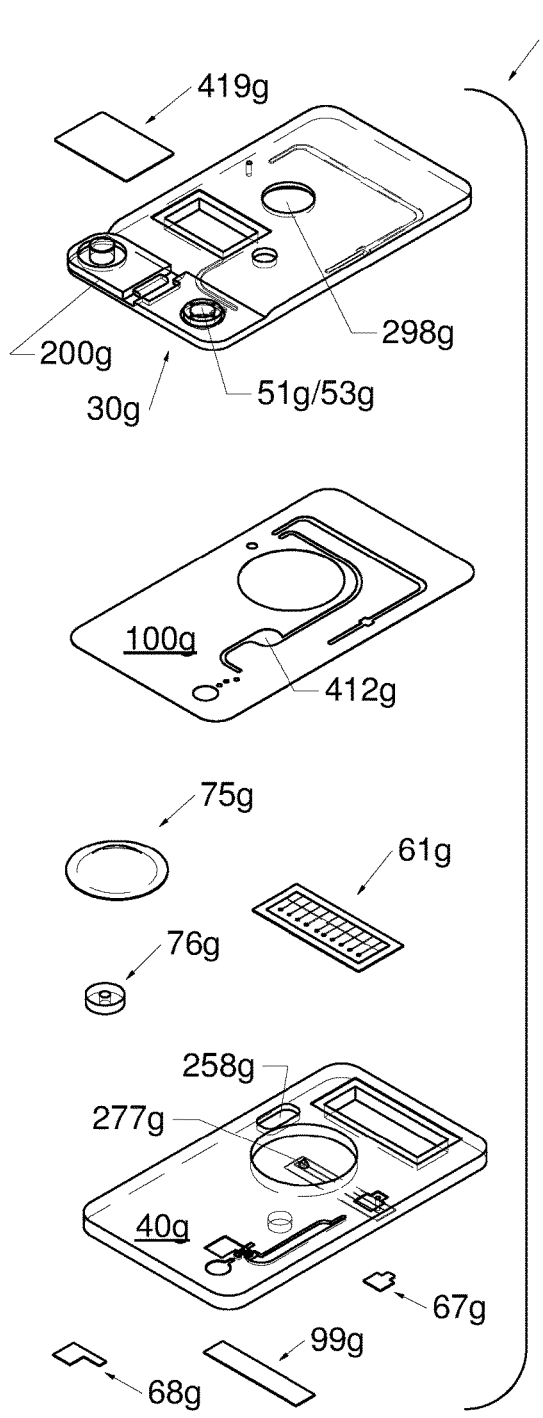
FIG. 19A is an exploded perspective top view of a measurement cartridge 10g for measuring at least one property of blood, according to a seventh embodiment of a measurement cartridge.
Figure 19B:
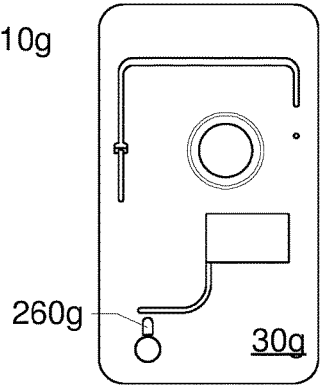
FIG. 19B is a bottom view of the first housing member 30g of the measurement cartridge shown in FIG. 19A.
Figure 19C:
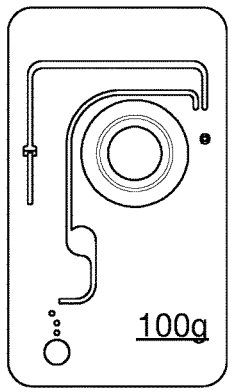
FIG. 19C is the bottom view of the first housing member 30g of the measurement cartridge shown in FIG. 19B, overlaid by and in alignment with the gasket 100g shown in FIG. 19A.
Figure 19D:
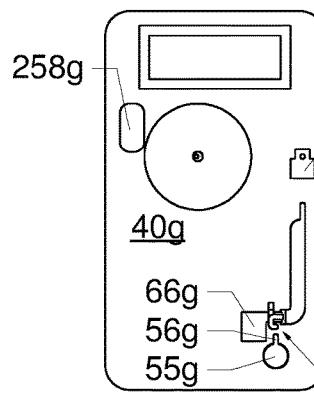
FIG. 19D is a top view of the second housing member 40g of the measurement cartridge shown in FIG. 19A.
Figure 19E:
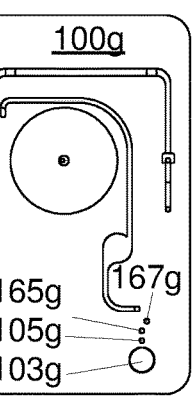
FIG. 19E is the top view of the second housing member 40g shown in FIG. 19D, overlaid by and in alignment with the gasket 100g shown in FIG. 19A.
Figure 19F:
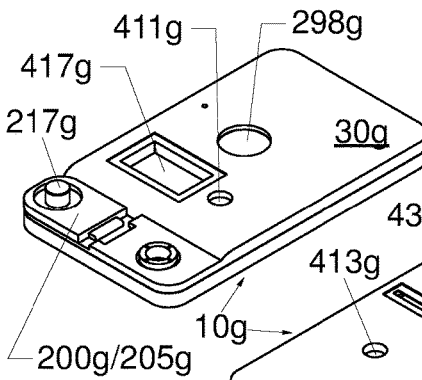
FIG. 19F is a perspective top view of the measurement cartridge 10g shown in FIG. 19A, in an open configuration.
Figure 19G:
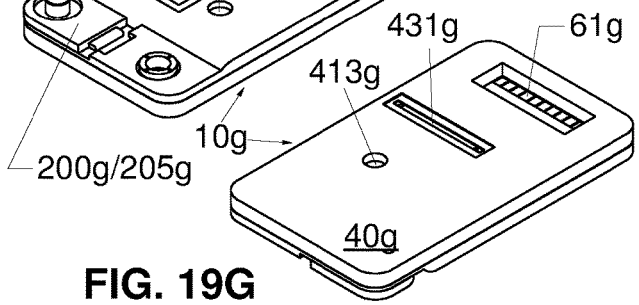
FIG. 19G is a perspective bottom view of the measurement cartridge 10g shown in FIG. 19A.

Shown in FIG. 19A is an exploded perspective top view of the measurement cartridge 10g. With the parts of cartridge 10g assembled, shown in FIG. 19F is a perspective top view of the cartridge 10g shown in FIG. 19A, with cap 200g adjusted to a first position, wherein the sample storage well 51g is configured to receive a blood sample. Shown in FIG. 19G is a perspective bottom view of the cartridge 10g shown in FIG. 19A. The separate first housing member 30g, second housing member 40g and their interaction with double-sided sticky gasket 100g used to hold 30h and 40h together are illustrated in FIGS. 19B-19E: Shown in FIG. 19B is a bottom view of the first housing member 30g of the cartridge shown in FIG. 19A; shown in FIG. 19C is the bottom view of the first housing member 30g of the cartridge shown in FIG. 19B, overlaid by and in alignment with the gasket 100g shown in FIG. 19A; shown in FIG. 19D is a top view of the second housing member 40g of the cartridge shown in FIG. 19A; and shown in FIG. 19E is the top view of the second housing member 40g shown in FIG. 19D, overlaid by and in alignment with the gasket 100g shown in FIG. 19A. Similar illustrations for measurement cartridge 10h are provided in FIGS. 22A-22G.

Some structural features and views are illustrated for either measurement cartridge 10g or 10h and not in both. Therefore, in order to understand the cartridges functionality, references may be made to structural features and views for either measurement cartridge 10g or 10h, and the cartridges are recognized by the letters "g" and "h" respectively. After blood is placed in the sample storage well 51g shown in FIG. 19A, gravity allows the blood to fall to the bottom 55g (see FIG. 19D) of sample storage well 51g. With reference to FIG. 23D, blood flow may stop at cutout 105h in double-sided sticky gasket 100h due to the relatively small area of cutout 105h fluidly connected to an enlarged section 260h. Another option for providing means for minimizing, mitigating, or modifying blood flow out of the sample storage well 51h is illustrated in FIGS. 10E and 10F regarding measurement cartridge 10c, wherein the means for minimizing, mitigating, or modifying blood flow out of the sample storage well 51c includes hydrophobic insert 451c disposed close to the bottom opening 55c of the sample storage well 51c. After the sample storage well 51g receives a blood sample, with cap 200g in a first position, the blood sample is advanced in a first stage and a second stage, which is discussed next.

In the first stage, cap 200g is adjusted from the first position to a second position, wherein in the second position the cartridge is configured so that the plunger 217g in cap 200g displaces at least some of the blood in sample storage well 51g through bottom opening 55g. The displaced blood flows through manifold 455g (see FIGS. 19D and 21E) via gasket cutout 105h illustrated in FIG. 21G, viewed in conjunction with FIGS. 23A and 23D regarding measurement cartridge 10h. Regarding measurement cartridge 10g (see FIG. 20A), manifold 455g splits the blood flow into blood conduits 401g and 402g. Blood conduit 401g is sufficiently small to allow blood to fill optical chamber 412g and allow some excess blood to flow towards waste receptacle 258g. The depth of the optical chamber is relatively shallow: preferably about 50-200 microliters. Due to the larger size of blood conduit 402g, a larger volume of blood enters blood conduit 402g. In the second configuration of measurement cartridge 10g, plunger 21g by design, pushes blood into blood conduit 402g, but not into electrochemical sensor chamber 261g until after the sensors in electrochemical sensor array 61g are calibrated (one-point) with calibration liquid from blister 75g. After calibration liquid is released from blister 75g and forced into electrochemical sensor chamber 261g for calibrating the sensors, blood from blood conduit 402g displaces the calibration liquid and the electrical signals from the blood is collected after the blood comes in contact with the sensors. Preventing blood flow into the electrochemical sensor chamber 261h of measurement cartridge 10h directly from the manifold 455h is not a requirement, because no sensor calibration is performed. However, an advantage to the two-step blood flow provides the benefit of using a smaller blood volume. Blood in the optical chamber 412g or 412h may be interrogated with electromagnetic radiation (EMR) any time after optical chamber 412g or 412h is filled with altered or unaltered blood. Altered blood is a mixture of blood and one or more reagents, for example a hemolyzing agent. In some applications, it may be beneficial to hemolyze only the blood entering the optical chamber 412h because hemolyzed blood scatters less EMR, therefore more EMR is transmitted through the blood sample providing stronger signals for the analyte of interest. On the other hand, hemolyzed blood is not desirable for measuring certain plasma analytes, for example potassium, because the concentration of potassium inside the red blood cells is about 20 times higher than the potassium concentration in plasma.

In the second stage, positive air pressure from, for example, an air bladder 417h pushes the blood in blood conduit 402h into electrochemical sensor chamber 261h for measurement by the one or more sensors in electrochemical sensors array 61h. Other means for pushing blood into electrochemical sensor chamber 261h includes an associated analyzer pump, as described regarding measurement cartridge 10c illustrated collectively in FIGS. 10A-10G. The pressurized air from air bladder 417h via air bladder duct 421h can only enter blood conduit 402h and cannot enter blood conduit 401h. This feature is illustrated in FIGS. 21E-21G regarding measurement cartridge 10g, viewed in conjunction with FIGS. 23B-23D regarding measurement cartridge 10h: Smaller section 268g of directional valve element 68g (68h regarding measurement cartridge 10h) folds against valve seat 331g, under pressurized air from air bladder duct 421g (see FIGS. 20D and 23D).

As mentioned before, the major difference between measurement cartridges 10g and 10h is that cartridge 10g comprises a calibration fluid blister 75g for performing a one-point calibration. An option in cartridge 10g is inclusion of a directional valve element 67g (see FIGS. 20B, 20E, 20G and 21H). The smaller section 267g of directional valve element 67g closes off fluid communication with blood conduit 402g by folding against valve seat 333g (see FIG. 21H), when calibration liquid from ruptured blister 75g is forced, through conduits 431g, 433g, 403g and 261g in that order, preventing mixing of blood and calibration liquid. Subsequently after the calibration liquid is used to perform a one-point calibration of sensors in electrochemical sensor array 61g, pressurized air from air bladder 417g pushes the blood from blood conduit 402g into the electrochemical sensor chamber 261g for blood measurement, and the pressure from the blood sample pushes the smaller section 268g of directional valve element 68g against the outlet of conduit 433g, preventing the blood from flowing towards the blister 75g.

Electrochemical Measurement

Electrochemical measurements are performed using electrochemical sensors installed in the detection chamber of the measurement cartridge. The electrochemical sensors may contain, without being limiting in any way, at least one of an amperometric sensor (e.g. a glucose sensor comprising an enzyme glucose oxidase or a sensor that measures $pO_2$), a conductivity sensor (e.g. a hematocrit sensor or an electrical switch), and a potentiometric sensor (e.g. an ion-selective electrode that can measure an electrolyte or pH).

As an example, electrochemical sensor array 61b of measurement cartridge 10b, illustrated collectively in FIGS. 9A-9G. The electrochemical sensor array 61b comprises at least one of an amperometric sensor, a conductivity sensor and a potentiometric sensor, and is disposed in a biosensor chamber 261b along a blood flow path. Some electrochemical sensors comprise at least one active surface exposed to the blood sample. Those skilled in the art will appreciate that biosensors may include various transducer arrangements that convert at least one property of the blood sample into an electrical signal. The electrical signal may be for example, a current, a voltage or a resistance/conductance. The transducer comprises at least one active surface for contacting the blood sample and the at least one active surface is one of a chemical sensitive surface, or an ionic sensitive surface, and wherein the at least one biosensor comprises at least one of a transistor, an ion-selective membrane, a membrane-bound enzyme, a membrane-bound antigen, a membrane-bound antibody, or a membrane-bound strand of nucleic acid. The cartridge 10b also comprises at least one electrical output contact, and the cartridge slot of the analyzer also comprises at least one electrical input contact, wherein the electrical output contact mates with the electrical input contact after the disposable cartridge is properly inserted into the receptor 14 of analyzer 80 illustrated in FIG. 18C. The electrochemical sensor array 61b is usually in a dry form, and is hydrated by the blood sample when the blood sample is allowed to flow over the electrochemical sensors. In some measurement cartridges, for example measurement cartridge 10g, illustrated collectively in FIGS. 19A-21J, the electrochemical sensor array 61g is hydrated by calibration liquid from blister 75g, prior to flow of blood over the electrochemical sensor array 61g. The calibration liquid in blister 76g is used to perform a one-point calibration (offset correction) of at least one of the sensors of electrochemical sensor array 61g. In addition, at infrequent intervals, calibration cartridge 20b may be used to perform a two-point calibration (i.e., offset and slope correction) electrochemical sensor array 61g.

Spectroscopic Measurement

Spectroscopic measurement of quantities of analytes in blood (i.e. unaltered blood) or altered blood is described.

Other terms like spectrophotometric, photometric or optical measurement may be used instead of spectroscopic. A block diagram of an example of a system 70 (lower panel) for measuring one or more analyte quantities per unit volume of blood and one or more formed element quantities per unit volume of blood is provided as a non-limiting example in FIG. 15. Output displays of the analyzer are an image of cells in blood (upper left panel) and an absorbance spectrum (upper right panel). For spectroscopic measurement alone, the beam splitter of system 70 (a bifurcated fiber optic cable 16 shown as an example) may be replaced with a single (i.e. non-bifurcated) fiber optic cable 17 for projecting the EMR (electromagnetic radiation) emerging from the sample directly onto an EMR dispersive element 28 (see FIG. 28). A reflective grating is shown as a non-limiting example of an EMR dispersive element 28. The embodiment illustrated in FIG. 28 is similar to the embodiment illustrated in FIG. 15, except that elements 18 (magnifying system of system 70), 22 (a two-dimensional multi-channel detector of system 70), 24 (an analog to digital converter of system 70), and 26 (a processor of system 70) are removed. A more detailed description of the aspects of a spectroscopic system shown in FIG. 28 is provided below.

With respect to the spectroscopic measurement alone, an analyzer or system may comprise at least one EMR source (represented by 12 in FIG. 15) for interrogating the sample and measuring the EMR transmitted through the sample or reflected from the sample. In certain embodiments of an analyzer or system, the analyzer or system may comprise at least two EMR sources or two EMR sources (represented by 12a and 12b in FIG. 28) for interrogating the sample and measuring the EMR transmitted through the sample (or reflected from the sample in various other embodiments) in the optical chamber of a removable measurement cartridge 10, shown inserted in a receptor 14 of the analyzer of system 70b (see FIG. 28). A spectrometer of the system 70b may comprise, for example, a one-dimensional multi-channel detector 32 arranged as a linear photo diode array (PDA) detector. A PDA detector is a linear repetitive installation of discrete photo diodes (may be referred to as pixels) on an integrated circuit chip. For measuring transmittance, the at least one source of EMR and the PDA detector should be on opposite sides of the optical chamber, and for measuring reflectance, both the at least one source of EMR and the PDA detector should be on the same side of the optical chamber. For reflectance measurement, the distal optical window of the optical chamber may be designed to be used as a reflecting member for measuring EMR reflected from the sample. Alternatively, a reflecting member may be installed in the cartridge receptor of the analyzer, and in close proximity to the optical window distal to the at least one EMR source.

In embodiments having at least two EMR sources, the at least two EMR sources that impinge upon (other terms like illuminates or interrogates may also be used) the contents of the optical chamber may comprise for example, an incandescent lamp, a fluorescent lamp, a deuterium lamp, a xenon lamp, one or more than one lasers, one or more than one narrowband light-emitting diodes (LEDs), and one or more than one broadband LEDs, or any combination thereof. The analyzer may also include a spectrometer, which may comprise for example, multichannel detectors such as a PDA, a charge-coupled device (CCD) array, or a complementary metal oxide semiconductor (CMOS) array.

The spectrometer may also comprise an EMR dispersive element, for example a prism, a grating, or a combination thereof for dispersing EMR reflected from a blood sample (i.e., reflectance or reflection, denoted by R) or EMR transmitted through a blood sample (i.e. transmittance or transmission, denoted by T), into component wavelengths. The dispersed EMR may be referred to as a blood diffraction spectrum, or a reference diffraction spectrum. A blood diffraction spectrum refers to intensities of EMR emerging from a blood sample and impinging upon an EMR dispersive element, and a reference diffraction spectrum indicates intensities of a set of incident EMR (i.e. EMR used to interrogate a blood sample) impinging upon the same EMR dispersive element. In both cases, the dispersed EMR may be measured using a PDA detector. It should be understood that a diffraction spectrum may include EMR emerging from an EMR dispersive element, whereby the wavelengths of the emerging EMR are identified visually based on colors, whereby a human eye is the detector. The grating may be one of a transmission (transmission may also be referred to as transmitting or transmittance or transmissive) grating, a reflection (reflection may also be referred to as reflecting or reflectance or reflective) grating, or a holographic grating. A diffraction spectrum may comprise raw electrical data measured by a one-dimensional multi-channel detector or processed raw electrical data, plotted against wavelength. Wavelengths are usually indicated along the x-axis of a graph, as illustrated in FIGS. 25-27 as examples. Unless an explicit meaning and/or context is disclosed, the terms electrical and electronic may be used interchangeably.

Raw data is described as data prior to undergoing any data processing. As an example, raw electrical data generated when EMR impinges upon a PDA detector is usually in amperes or volts, which is regarded as analog data. A current to voltage converter may be used to convert amperes to volts. The raw electrical data may be transformed by an analog to digital converter (ADC) and converted into digital data. Therefore, a blood diffraction spectrum and a reference diffraction spectrum may be transformed by an ADC into a blood digital spectrum and a reference digital spectrum respectively. The ADC may be a component of the one-dimensional multi-channel detector, or it may be a separate module in an analyzer. Some examples of data processing are provided below. The blood and reference digital spectra may also be regarded as raw data, which are processed to obtain absorbance as an example, i.e. absorbance may be regarded as processed data. Absorbance data may also be considered as raw data before they are processed to calculate first order derivative of absorbance at a wavelength, i.e. the slope of the raw absorbance data at that wavelength. Absorbance may also be referred to as zero order derivative of absorbance.

Processing data may be in stages and the term data pre-processing, may refer to smoothing the data before applying a calibration equation, as an example. Unless indicated otherwise, the term data may refer to raw data, pre-processed data, or processed data. Data processing in spectroscopy may include one or more of the following non-limiting examples:

1. Converting analog current or voltage values into digital values using an ADC;
2. Converting current into voltage using a current to voltage converter;
3. Calculating absorbance;
4. Calculating transmittance;
5. Calculating reflectance;
6. Smoothing ADC values;
7. Smoothing absorbance values;
8. Smoothing transmittance values;
9. Smoothing reflectance values;

10. Subtracting background electrical activity from sample and reference measurements; background electrical activity may be due to dark current (i.e., current generated in a PDA detector when the main source[s] of EMR is[are] switched off), and ambient EMR.
11. Interpolating and extrapolating signals from pixels to provide signals in desired wavelength increments that are smaller than the pixel dispersion, i.e. the pixel resolution or the space between two pixels. As an example, the pixel dispersion of the PDA detector used to generate the illustration in FIG. 25 is 1.98 nm/pixel. Furthermore, in this example, spline fitting generated signals per 0.1 nm, but the actual display points were in wavelength whole numbers and in increments of 1.0 nm. The actual points are not visible due to curve smoothing. All analyzers should have the same wavelength table, that is the wavelengths assigned to each pixel, to facilitate calibrate algorithm transfer. However, all analyzers may not have the same wavelength table and, and the wavelengths in the analyzer-specific wavelength table may not be in whole numbers. An example of a wavelength table that may be used by all analyzers, is a wavelength table having wavelengths in whole numbers and in increments of 1.0 nm. This is an example of a standard set of wavelengths or a standard wavelength table. Without the use of a standard set of wavelengths, the wavelengths in the calibration equation using wavelengths from a parent analyzer (i.e., the analyzer that is calibrated using data collected by this analyzer) may not exist in the wavelength table of a child analyzer (i.e., an analyzer that uses the calibration algorithm developed for the parent analyzer). Therefore, a standard set of wavelengths may be created, having a suitable range that encompasses at least the wavelengths in all the calibration equations implemented in an analyzer, and an arbitrarily chosen increment, for example 0.1 nanometer (nm), 1 nm, or 2 nm. An arbitrarily chosen increment is chosen mostly for convenience, and providing sufficient resolution. With a standard set of wavelengths established, the spectral data at the wavelengths from the analyzer-specific wavelength table may be mathematically mapped unto the standard set of wavelengths, so that all analyzers could provide spectral data at wavelengths common to all analyzers.
12. Mapping a portion of a blood digital spectrum or a portion of a reference digital spectrum unto a standard set of wavelengths. Each analyzer undergoes a process or wavelength calibration to generate an analyzer-specific wavelength table, described below. The analyzer-specific wavelength table from one analyzer may be different from the analyzer-specific wavelength table from a different analyzer. Mapping refers to the process of associating blood or reference spectroscopic signals at wavelengths from the analyzer-specific wavelengths, with a wavelength from a standard set of wavelengths. The process of mapping enables calibration algorithms developed for one analyzer using data collected by that analyzer (referred to as a parent analyzer), to be used by another analyzer (referred to as a child analyzer). Mapping may be performed on an entire spectrum or on portions of a spectrum, and a portion of spectral data may be as small as spectral data at a single wavelength. A portion of spectral data at a plurality of wavelengths may be as small as data at two wavelengths; the two wavelengths my be adjacent to each other or there may be a gap between the two wavelengths.
13. Pooling data. Optionally, data from more than one analyzers may be combined or pooled to generate calibration algorithms. Pooled data may provide calibration equations that include analyzer to analyzer variabilities.
14. Transforming absorbance value at a wavelength into an order derivative of absorbance at the wavelength. As examples, zero order derivative is the raw absorbance, first order derivative of an absorbance curve at a wavelength is the slope of the absorbance curve at that wavelength, and second order derivative of an absorbance curve at a wavelength is the slope of the first order derivative curve at that wavelength, and so on.
15. Transforming transmittance value at a wavelength into an order derivative of transmittance at that wavelength. This is similar to the process used for absorbance.
16. Transforming reflectance value at a wavelength into an order derivative of reflectance at that wavelength. This is similar to the process used for absorbance.
17. Savitzky-Golay smoothing or differentiation filtering. These are published mathematical smoothing process.
18. Applying a calibration equation (or calibration algorithm) for the concentration or quantity of an analyte, to transform spectral data at one or more wavelengths of a blood digital spectrum and reference digital spectrum at the corresponding wavelengths, into the concentration or quantity of the analyte. Calibration equations may also be developed for the ratio of the concentrations or quantities of two analytes, or the ratio of the quantity of an analyte to the sum of the quantities of a plurality of analytes. It should be understood that these ratios are considered as the quantity of an analyte, even though they may involve more than one analytes. For example: 1) % $HbA_{1c}$ is the ratio of a quantity of $HbA_{1c}$ in a blood sample to a quantity of total Hb in the same blood sample; 2) Fractional hemoglobin (Hb) oxygen saturation is the ratio of a quantity of Oxy-Hb in a blood sample to the sum of the quantities of other Hb species, usually Oxy-Hb, Deoxy-Hb, Met-Hb, and Carboxy-Hb, in the same blood sample; and 3) Functional Hb oxygen saturation is the ratio of a quantity of Oxy-Hb in a blood sample to the sum of the quantities of Oxy-Hb and Deoxy-Hb. Therefore, the % $HbA_{1c}$, the fractional Hb oxygen saturation, and the functional Hb oxygen saturation are examples of analytes that may be referred to using the term quantity of an analyte.

For performing spectroscopic measurement of altered or unaltered blood on an analyzer, the PDA detector of the analyzer usually undergoes a process of wavelength calibration. As an example, two laser beams (#1 and #2) may be used to conduct wavelength calibration of a PDA detector, which for example, comprises 256 pixels (or photo diodes). The wavelengths of lasers #1 and #2 are 340 nm and 688 nm respectively, and project onto pixels 20 and 240 respectively. Therefore, the wavelengths of 340 nm and 688 nm are assigned to pixels 20 and 240 respectively. The wavelength range from pixel 20 to pixel 240 is 340-688 nm and by linear interpolation, a pixel dispersion of 1.582 nm per pixel [(688−340)÷(240−20)] is calculated. In other words, the pixel resolution or the space between two pixels is 1.582 nm. By linear extrapolation, pixel 1 is assigned the wavelength of 309.9 nm [340−1.582×(20−1)], and pixel 256 is assigned the wavelength of 713.3 nm [688+1.582×(256−240)]. Therefore, the analyzer-specific wavelength table for this analyzer is 309.9−713.3 nm in increments of 1.582 nm. The two lasers may emit EMR at any wavelength within the range of 309.9−713.3 nm, providing sufficient spacing so that linear interpolation and linear extrapolation of wavelengths may be conducted. More than two lasers may be used. A person having skill in lasers would appreciate that a laser may have a spectral bandwidth (the band width of EMR at one-half the maximum emission), of greater than or less than 1 nm, and a laser having a spectral bandwidth greater than 1 nm may project unto more than one pixels, making wavelength calibration more complex than as described above.

As an alternative, all analyzers may be calibrated for wavelengths so that the wavelength associated with each pixel is approximately the same. This approximation may allow the use of pixel numbers in the calibration equations instead of wavelengths. This process may be used if high accuracy of analyte measurement is not required.

A person skilled in spectroscopy should appreciate that the wavelength range and spectral resolution of the PDA detector depends on several factors, for example, the semiconductor material used to construct the PDA detector, the EMR dispersive element used (e.g. a prism, a transmission diffraction grating, reflection diffraction grating, or a combination thereof), the orientation of the grating relative to the PDA detector, the curvature of the diffraction grating, and the blaze angle of the diffraction grating. As an example, a 512 pixel PDA detector having a pixel dispersion of 1.98 nm/pixel and using a 16-bit ADC, was used to generate the data illustrated in FIGS. 25-27. It should be observed that a wavelength range of 700 nm (1,000–300 nm) shown is less than the maximum wavelength range capability of the PDA detector, illustrating that the EMR source determines which pixels are useful.

The source of EMR is a determining factor in the usable wavelength range because the source of EMR is usually the incident EMR interrogating a sample, and in spectroscopy, the amount of incident EMR emerging from the sample is usually measured. Each photo diode is typically scanned in microseconds, which provides sufficient time to accumulate sufficient charge on the photo diode, significantly greater than background current caused by dark current and possible ambient EMR, without saturating the photo diode. Usually, a photo diode converts EMR into current. The time the photo diode is exposed to the EMR may be referred to as "integration time" (IT) or measurement time. Background current should be measured for the same IT as the sample IT since background current accumulates over time. Reference measurement should also be measured for the same IT as the sample IT, to indicate the intensities of the incident EMR. The use of different ITs for the sample, reference and background measurements is not preferred because the accuracy of analyte measurements may be affected. Background current may be subtracted from both the sample measurement and reference measurement, in order to develop calibration equations that predict more accurate and precise measurements of analyte quantities. Reference measurements may be performed with an empty cartridge (i.e. a cartridge devoid of blood in the optical chamber) in the analyzer receptor, or through air, i.e. with no cartridge present in the receptor (i.e., the receptor is devoid of sample, e.g. blood). Advantages to making a reference measurement through air are: 1) It is a more user-friendly process since the user has to deal with one cartridge, that is the sample cartridge; and 2) Measurements through air should have less variability than an empty cartridge (used to conduct the reference measurement), due to cartridge imperfections. The IT is usually optimized for the analyzer, and therefore may be referred to as pre-determined measurement time or pre-determined IT. The pre-determined IT may also be referred to as a time interval defined by a start time and an end time, and a duration of the time interval, i.e., the difference between the start time and the end time.

The bit depth of the analog to digital converter (ADC) determines the digital EMR emission when the photo diodes become saturated. As examples, an 8-bit ADC can produce 256 discrete ADC values (i.e. $2^8$) and a 16-bit ADC can produce 65,536 discrete ADC values (i.e. $2^{16}$). The emission spectra shown in FIG. 25 were produced from a concave reflection grating using a 16-bit ADC, therefore the digital saturation EMR intensity of the photo diodes occurs at 65,536 ADC numbers. Saturation, or "saturating a photo diode", means that the photo diode has reached a maximum response in current and any additional photons impinging upon the photo diode is usually converted to heat instead of current. In other words, increases in an intensity of an EMR signal received by a photo diode of a one-dimensional multi-channel detector beyond the saturation EMR intensity does not increase digital signal derived by the photo diode from that EMR signal. The maximum digital number, i.e. 65,536 in the case of a 16-bit ADC, corresponds to the maximum electrical signal response of a photo diode to EMR.

Because the scanning time is short (for example, microseconds in some embodiments), the photo diodes in the PDA detector are virtually scanned simultaneously. The photons are usually converted to electrical current, which is measured and digitized. The current may be converted to a voltage and the voltage is digitized. Absorbance, sometimes referred to as absorption and denoted by A, may be determined for each wavelength, according to the equation:

$$A = -\log_{10} T.$$

It is well known that transmittance or transmission is defined as the fraction of incident EMR which is transmitted or passes through a sample. Thus:

$$T = I/I_o, \text{ where}$$

$I_o$=the intensity of EMR impinging upon or interrogating the sample (i.e. incident EMR) and $I$=the intensity of EMR emerging from the sample after passing through the sample or reflected from the sample (i.e. emerging EMR).

The amount of EMR impinging upon the optical chamber, $I_o$, may be measured by interrogating an empty cartridge in the analyzer receptor, or measured with no sample cartridge present in the analyzer receptor (that is through air). A reference diffraction spectrum indicates intensities of a set of incident EMR. The EMR impinging upon the optical chamber, $I_o$, may be measured before or after every sample measurement, or less frequently and stored in the analyzer associated non-transient computer-readable memory for later use, and may be updated periodically. Preferably the background current is subtracted from $I_o$ and I. $I_o$ and I are referred to as the reference measurement and sample measurement respectively.

Some analytes may be measured at one or more wavelengths. As an example, spectroscopic measurements are used to estimate prothrombin time (PT; usually reported as PT-INR [INR=International Normalized Ratio]), activated partial thromboplastin time (aPTT), activated clotting time (ACT), or thrombin time (TT), and since a normal PT is about 10-14 seconds, a normal ACT is about 70-130 seconds, and a normal TT is about 15-19 seconds, the measurements are performed every second. With respect to coagulation measurements, e.g. PT, ACT and TT, an aspect is to use the absorbance at one or more wavelengths or pattern recognition using absorbances at a plurality of wavelengths. Techniques of pattern recognition, combined with spectroscopy are known by those having skill in the art. An example where spectroscopy, combined with pattern recognition algorithms are used and that may be applied to the methods described herein, is provided in Zhang et. Al. (Mid-Infrared Spectroscopy for Coffee Variety Identification: Comparison of Pattern Recognition Methods", J. of Spectroscopy, Volume 2016, Article ID 7927286). As blood coagulates, the blood changes from various liquid varieties to various gel varieties, with corresponding changes in spectroscopic patterns, allowing one to use similar techniques as those used by Zhang et. al. to identify different variety of coffee beans. The specific blood coagulation time measured depends on the reagents included in the cartridge. For example, thromboplastin may be used for PT, celite or kaolin may be used for ACT, and thrombin may be used for TT.

Typically, blood coagulation time is measured using mechanical methods. For spectroscopic-based assays, citrated plasma is usually used in place of whole blood, because with whole blood, a much larger fraction of the incident EMR is scattered and absorbed by the blood cells, compared with the change in emerging EMR due to gelling of the plasma. However, separating the plasma from the whole blood requires time and centrifugation equipment. It is well known that as plasma clots or coagulates, the absorbance at a single wavelength increases. By way of example, G. O. Gogstad et. al. (1986, "Turbidimetric Determination of Prothrombin Time by Clotting in a Centrifugal Analyzer" Clin. Chem. 32/10, 1857-1862), describe the change in absorbance spectra of plasma during coagulation. However, measurement of coagulation time using whole blood instead of plasma is more representative of in vivo coagulation. Therefore, there is a need for spectroscopic measurement of the blood coagulation time employing whole blood. In order to improve the signal to noise ratio when whole blood is used with the devices as described herein, the depth of the optical chamber should be relatively small, for example about 50-200 micrometers. The use of absorbance, reflectance or transmittance at a single wavelength to generate a clotting reaction curve (for example as shown in FIG. 1 of Gogstad et. al. 1986, using absorbance), and the calculations used to compute clotting time, are considered to be within the scope of the present invention. Gogstad et. al. also provided examples of calculations used to compute clotting time that may be used according to the methods described herein.

As an example, the source of EMR may be an incandescent lamp e.g. a tungsten lamp. U.S. Pat. No. 6,651,015 describes how spectrophotometric apparatus are calibrated for measuring properties of blood, using multi-wavelength analysis. With the use of a source of EMR like a tungsten lamp, which provides multiwavelength EMR (the tungsten lamp is polychromatic, whereas a laser is monochromatic), and the use of a linear PDA detector, the analyzer has the capacity to generate full absorbance spectra possibly in milliseconds. Several spectra may be collected and averaged to minimize noise. Mathematical smoothing techniques, which are covered extensively in the literature, may be used to minimize noise. Other mathematical techniques like the use of an order derivative of absorbance are also discussed in U.S. Pat. No. 6,651,015. Even though full absorbance spectra are obtained, selected portions (as small as a single wavelength) of the absorbance spectra, a wavelength range of the absorbance spectra, or the full absorbance spectra, may be used in order to determine a concentration or quantity of one or more analytes of interest. Examples of an absorbance spectra for several relevant blood analytes are provided in FIG. 29. Examples of the absorbance spectrum of whole blood at an expanded wavelength range of 300 nm to 1,000 nm are shown in FIGS. 26 and 27. Absorbance spectra are used for illustrations, but any order derivative of absorbance, any order derivative of transmission, or any order derivative of reflectance are considered to be within the scope of the present invention.

Application of spectroscopic technology in POCT can be improved by expanding the wavelength range of absorbance, transmission, and reflectance measurements. More analytes can be measured simultaneously if the wavelengths include portions of the ultraviolet (UV) spectrum, the visible (VIS) spectrum, and portions of the near infrared (NIR) spectrum. A UV, VIS and NIR spectra in the order listed may be included in the wavelength range of 300 nm to 1,000 nm. In order to measure absorbance/transmission/reflectance of EMR from UV to NIR, the following components of a POCT analyzer must be considered: 1) means for combining more than one source of polychromatic EMR (e.g. UV, VIS and NIR) impinging upon a blood sample; 2) means for dispersing EMR emerging from the sample (transmitted through or reflected from the sample) into its component wavelengths; 3) an array of photo diodes (other detectors, e.g., CCD or CMOS, may be used) for converting the dispersed EMR into electrical signals; and 4) an ADC for transforming the electrical signals into digital information or binary numbers (a series of 1's and 0's). Binary numbers can be converted into ADC values or ADC numbers, and the discrete ADC values depend on the bit depth of the ADC discussed earlier.

An aspect of the present invention is to implement a first broadband LED (light-emitting diode) and a second broadband LED in a manner so as to provide incident EMR at a wavelength range greater than the ranges provided by either one LED. The intent of the manner of implementation is also to mitigate the effects of stray EMR. In a particular embodiment for illustration, which should not limit the present invention in any way, the two LEDs are optimized separately using a measurement time or integration time (IT) of 300 ms for the first broadband LED and an IT of 60 ms for the second broadband LED, and percent of power input to the LEDs of 40% for the first broadband LED and 64% for the second broadband LED. The bit depth of the ADC in this embodiment is 16-bit, therefore as mentioned previously, the digital saturation EMR intensity of the photo diodes occurs at 65,536 ADC numbers. The maximum emissions may be increased by increasing the IT, increasing the power input to the LEDs, or a combination thereof. The ADC values for each wavelength may be measured multiple times and averaged to reduce the level of noise. In an embodiment, 10 measurements were averaged to produce the absorbance spectra shown in FIG. 26. The two LEDs were activated independently. The absorbance spectra of blood shown in FIG. 26 were truncated at 470 nm (i.e. 300-470 nm for the first broadband LED and 470-1,000 nm for the second broadband LED) to form a composite absorbance spectrum shown in FIG. 27. By forming a composite spectrum shown in FIG. 27, the effects of stray EMR on certain portions of the spectrum of each LED are mitigated. The embodiment comprises at least mitigating means for mitigating the effect of stray EMR caused by overlap between the between the first order and second order diffraction spectrum of the first broadband LED. The mitigating means may comprise EMR sources for (when the removable cartridge is received in the receptor) providing a first set of incident EMR to the optical chamber to interrogate the blood sample during a first time interval of a first duration (i.e. the first IT), and a second set of incident EMR to the optical chamber to interrogate the blood sample during a second time interval of a second duration (i.e. the second IT). The first IT and the second IT are sufficient for each LED to produce greater than 10% the emission that saturates the photo diodes (see FIG. 25). The embodiment comprises at least one data processor for controlling the operation of the two EMR sources. In one embodiment, the first time interval and the second time interval occur such that at least a portion of the first time interval occurs when the second time interval is not occurring, and at least a portion of the second time interval occurs when the first time interval is not occurring. In another embodiment, the first time interval and the second time interval may occur such that the first time interval and the second time interval do not overlap in time. In other words, the second time interval may begin after the first time interval is completed, or the first time interval may begin after the second time interval is completed. Too much overlap between the first time interval and the second time interval may affect the accuracy of certain analyte measurements, and the sum of ADC values for reference measurements—i.e. when no blood sample is present in the path of incident EMR to attenuate the EMR, may approach saturation of one or more photo diodes. The amount of overlap between the first and second time intervals that is allowable may depend on the acceptable inaccuracies of the measured quantities of the analytes, and the avoidance of photo diode saturation. Therefore, each LED should be optimized for power consumption and IT.

The example illustrated in FIG. 27 is a composite absorbance spectrum, where A=B=470 nm, although A and B are shown to be apart. In other embodiments, B nm may be greater than A nm, or A nm may be greater than B nm. The mitigating means for mitigating the effects of stray EMR may also comprise truncating the first broadband emission spectrum at wavelengths below A nm (and discarding the emissions at higher wavelengths) to produce a first truncated emission spectrum, truncating the second broadband emission spectrum at wavelengths greater than B nm (and discarding the emissions at lower wavelengths) to produce a second truncated emission spectrum, and combining the first truncated spectrum and the second truncated spectrum to produce a composite emission, absorbance, transmission, or reflectance spectrum. FIG. 27 is an example of a composite absorbance spectrum, the wavelength range is between 300 nm and 1,000 nm, but this wavelength range should not be considered limiting in any way. It should be understood that the emission spectral data may be truncated before the absorbances, reflections or transmissions are calculated, or the full absorbance, reflectance or transmittance spectral data may be calculated first and subsequently truncated. As mentioned previously, unless indicated otherwise, the term data may refer to raw data, pre-processed data, or processed data.

It is known that the approximate wavelength ranges of UV, Visible and NIR EMR are about 10-400 nm, about 400-700 nm, and about 700-2500 nm respectively. The colors of the visible spectrum, as one goes from short to longer wavelengths, are Violet, Indigo, Blue, Green, Yellow, Orange and Red. These colors when combined produces white EMR. The opposite occurs when white EMR is dispersed by an EMR dispersive element, for example a prism, a grating or a combination thereof. The EMR dispersion is caused by diffraction of the white EMR. In the example illustrated in FIG. 27, a first selected wavelength for truncating the emission of the first broadband LED is 470 nm, but 470 nm should not be considered limiting in any way. Also, in the example shown, a selected wavelength for truncating the emission spectrum of the second broadband LED is also 470 nm, but the second truncating wavelength may be >470 nm or <470 nm, discussed previously. The composite absorbance spectra for a blood sample using a truncating wavelength of 470 nm for both LEDs is illustrated in FIG. 27. Therefore, virtually all the wavelengths from 300 nm to 1,000 nm are available to develop calibration equations for measuring the quantities of analytes.

The two emission diffraction spectra are displayed in FIG. 25, wherein the first broadband LED emission is shown as a solid line and the second broadband LED emission spectrum is shown as a broken line. The two emission spectra were measured with no cartridge present in the analyzer receptor and represent the incident EMR impinging upon the blood in the optical chamber. They are also referred to as reference spectra, i.e., the reference diffraction spectrum detected by the PDA detector at a first wavelength range indicates intensities of a first set of incident EMR, and the reference diffraction spectrum detected by the PDA detector at a second wavelength range indicates intensities of a second set of incident EMR. The reference diffraction spectra may also be measured with a cartridge devoid of blood in the optical chamber, inserted in the analyzer receptor. The background electronic signals for the corresponding IT, shown in FIG. 30, are subtracted from the emission spectra of the respective LEDs and shown in FIG. 25. Background electronic signal is due to, for example, ambient EMR when the LEDs are switched off, and dark current occurring when the LEDs are switched off. Dark current is due to random electronic activity in the photo diodes when there are no photons impinging upon the photo diodes, and dark current is proportional to time and temperature. Background is usually predictable and pixel-specific, accounting for the small spikes shown in FIG. 30. Background signal is a source of error in determining an analyte quantity and is optionally measured and subtracted from both the sample and the reference measurements at the same IT. In other words, if the sample and reference measurements use an IT of 60 ms, the background signal should also be measured at 60 ms. Background signal may be measured and subtracted for each sample.

The corresponding absorbance spectra for unaltered blood are displayed in FIG. 26, and the absorbances may be calculated either before or after the emission spectra are truncated. In this example, the absorbance spectrum from the first broadband LED is truncated to provide a wavelength range of 300 nm to 470 nm, and the absorbance spectrum from the second broadband LED is truncated to provide a wavelength range of 470 nm to 1,000 nm, providing a composite absorbance spectrum for wavelengths 300 nm to 1,000 nm (see FIG. 27). It should be understood that the truncation wavelength of 470 nm is just an example and should not be limiting in any way. Also, the composite absorbance spectrum may have a gap around 470 nm, or the two truncated emission spectra may overlap around 470 nm.

As an example of overlap between A nm and B nm, A=480 nm and B=460 nm, wherein the emerging EMR from the two LEDs overlap by 20 nm, and the information about the sample in this 20 nm overlap may be corrupted, causing errors in analyte measurements. It should also be considered that the sum of emissions at some or all of the wavelengths where there is overlap, may saturate the detector whereby no information about the sample is provided at wavelengths where saturation occurs, and possibly adjacent wavelengths due to the blooming effect. Blooming occurs when the charge in a photo diode exceeds the saturation level and the photo-generated charge results in overflowing, or blooming, of the excess electrons into adjacent photo diodes.

Regarding gap, the bigger the gap between A nm and B nm, the greater gap in the absorbance spectrum that contains no information about the sample. As an example of gap between A nm and B nm, A=460 nm and B=480 nm, wherein the gap is 20 nm, which contains no information about the sample. The analyzer may be calibrated for one or more species of bilirubin and one or more species of hemoglobin as examples of analytes, and not require spectral information between 460 nm and 480 nm (i.e. the gap of 20 nm), because there may be sufficient information about bilirubin species and hemoglobin species in other parts of the composite spectrum, illustrated in FIG. 29. Similar arguments may apply also to transmittance and reflectance measurements.

Stray light (or stray EMR) in spectroscopy is usually thought of as EMR impinging upon an array of photodetectors, wherein the stray EMR did not first go through the sample. This is usually caused by having a sample in an analyzer, wherein the sample is not shielded properly from ambient EMR, or EMR impinges upon the photodetectors after undergoing internal reflection inside the analyzer. In this case, each wavelength of the stray EMR may impinge upon the photodetector assigned the wavelength of the stray EMR because the stray EMR may still reach the PDA detector via the grating or other EMR dispersive element. Another type of stray EMR is EMR having a wavelength that activates a photo diode that is assigned a different wavelength (based on wavelength calibration). Photo diodes are photo sensors that convert incident EMR into electrical signals, and the photo diodes cannot discriminate one wavelength from another. An example of this type of stray EMR is illustrated in FIG. 24: the labeled grey section indicates where red EMR from the first order diffraction spectrum overlaps with blue EMR from the second order diffraction spectrum. The wavelength of red EMR is longer than the wavelength of blue EMR, but the photo diodes produce electrical signals in response to the combination of the red EMR and the blue EMR. In spectrometers that use a grating to create a diffraction spectrum, the geometry of the grating is usually optimized to mitigate any overlap as illustrated in FIG. 24, but it is possible that some of the emission of the first broadband LED at wavelengths around 550-750 nm, illustrated in FIG. 25, is the result of overlap between first and second order diffraction spectra of the first broadband LED. Another possible source of the overlapping EMR is second order diffraction from the first broadband LED at wavelengths <300 nm (the source of EMR<300 nm is discussed below) when measurement is made through air for the reference measurement. In contrast, if a sample is measured in a plastic cartridge, the plastic is expected to absorb EMR<300 nm, and if the first order diffraction is absorbed by the cartridge, then no second order diffraction is expected. In other words, second order EMR may be present in the reference measurement and not in the sample measurement, resulting in errors in the absorbance calculation.

When an LED emits very little EMR at certain wavelengths, other sources of stray EMR may increase the low levels of reference emission, and in contrast, a cartridge with or without sample may block some of the stray EMR that affected the reference measurement, resulting in errors in the absorbance calculation. In some cases, both sample and reference measurements may be affected by stray EMR, producing errors in the calculation of absorbance. Another potential source of stray EMR may be EMR scattered backward from intact blood cells unto the fluorescence material in a wafer attached to an LED and discussed below as an optional EMR source. The backward scattered EMR may act as excitation EMR, causing the fluorescence material to emit low levels of fluorescence at a different set of wavelengths compared to the primary fluorescence bands produced by the excitation UV. These low levels of fluorescence may be referred to as secondary fluorescence, as indicated in FIG. 25 for illustration, keeping in mind that this secondary fluorescence may occur in the sample measurement and not in the reference measurement. Therefore, any type of stray EMR may affect the absorbances of both LEDs, as illustrated in FIG. 26, and truncation of the spectra to produce a composite spectrum as illustrated in FIG. 27 is a potential means for mitigating the effect of stray EMR. Truncation of the spectra to produce a composite spectrum as illustrated in FIG. 27 is also a potential means for expanding the wavelength range of an analyzer, whereby the spectral data for the extended wavelength range may be of better quality than the spectral data produced by a single source of broadband EMR.

Regarding certain species of hemoglobin, the major absorbance peak is at about 415 nm, and two other significant peaks occur at about 540 nm and 580 nm. All three absorbance peaks are observed in the composite absorbance spectrum illustrated in FIG. 27, but all three peaks are not observed in the absorbance spectrum derived from the second broadband LED. The absorbance peaks at about 540 nm and 580 nm derived from the first broadband LED appear to be underestimated when compared to the second broadband LED. The high signal to noise ratio observed in the composite spectrum shown in FIG. 27 is a powerful tool for POCT for measuring quantities of hemoglobin species, and bilirubin species in unaltered blood, as non-limiting examples.

Although the composite absorbance spectrum illustrated in FIG. 27 is virtually continuous, a person having ordinary skill in the art would appreciate that the level of continuity in the composite spectrum depends on the chemometrics technique used to develop calibration algorithms for measuring a quantity of an analyte. For example, multiple linear regression chemometrics techniques may use terms comprising a plurality of discrete wavelengths instead of the entire composite absorbance spectrum. An order derivative of absorbance, an order derivative of transmission, or an order derivative of reflectance, may be used to develop calibration equations. Chemometrics software, e.g. JMP Statistical Discovery From SAS, may be used to select a plurality of wavelengths in calibration equation terms, whereby the calibration equations are expected to predict accurate measurements of quantities of analytes in blood samples collected from both healthy and non-healthy subjects.

In order to build an analyzer with minimal to no moving parts, the EMR sources, the one-dimensional multi-channel detector, the EMR dispersive element, and the processor may be fixedly attached to the housing such that the EMR sources, the one-dimensional multi-channel detector, the EMR dispersive element, and the processor are substantially stationary relative to the housing and each other.

A diffraction grating may be used as an EMR dispersive element for dispersing EMR into its component wavelengths. A diffraction grating is an optical component with a repetitive structure embedded within the grating that diffracts EMR into several beams of different wavelengths travelling in different directions (i.e., different diffraction angles). The repetitive structures may be for example, narrow hollow slits for transmitting EMR (i.e. a transmission or transmissive grating), or narrow reflective rulings or ridges (i.e. a reflection or reflective grating). There are also gratings that modulate the phases of incident EMR rather than the amplitude, and these types of gratings use holography. Holography is a technique that enables a wavefront to be recorded and later re-constructed and is best known for generating three-dimensional images. The surface of a grating may be planar or concave. Planar gratings generally give higher resolution over a wide wavelength range. Concave gratings can function as both an EMR dispersive and focusing element in a spectrometer.

The repetitive structure affects the amplitude and/or phase of the incident EMR (waves), causing constructive and destructive interference in the output waves. The spacing of the repetitive structures determines the angles at which a single wavelength will constructively interfere to form diffracted orders. In addition to the spacing of the repetitive structures, the repetitive structure profile plays a key role in the performance of a grating. When monochromatic EMR strikes a grating, a fraction of it is diffracted into each order, termed its efficiency. Maximizing the efficiency into a single order, typically the first order, is often desired to ensure increased EMR collection. To optimize this efficiency for a single wavelength, a procedure known as blazing is performed. This involves modifying the groove profile, including facet angles, shapes and/or depths. The blaze wavelength is the wavelength for which the grating is most efficient.

Usually only the first order diffraction spectrum, positive or negative, is desired and so wavelengths from other orders (e.g. second order diffraction) may need to be blocked using for example, order sorting filters. Overlap of two orders of diffraction patterns tend to corrupt the spectral data. For example when blue EMR from the second order overlaps with red EMR from the first order, the blue EMR from the second order is seen as stray EMR by the detector, since the detector cannot discriminate between wavelengths. This is illustrated in FIG. 24. Another method of dealing with overlap of two orders of diffraction is mathematical approximation. A simpler and more effective means of eliminating the overlap is required, which does not use filters or mathematics, and no substantial portion of the absorbance or transmittance spectrum is corrupted or deleted.

The desirable properties of a POCT spectroscopic analyzer are: 1) EMR emission across a wide wavelength range; 2) minimal or no moving parts; 3) stability of EMR source(s) and other parts over a long service life; 4) no requirement for hemolyzing the blood; 5) small size; and 6) low cost. Common sources of EMR are halogen lamps for the visible (VIS) and near-infrared (NIR) wavelengths, and deuterium lamps for the ultraviolet (UV) wavelengths. The wavelength range of EMR emission from a halogen lamp is similar to the emission of the second broadband LED illustrated in FIG. 25. UV-VIS (ultraviolet-visible) laboratory spectrophotometers are known for their wide wavelength range by combining deuterium and halogen lamps. The lamps are usually switched by moving the lamps themselves or by rotating a mirror. A xenon lamp may also be used in laboratory spectrometers to provide a wide wavelength range. For POCT, xenon lamps produce more heat and consume more power than LEDs.

Use of small inexpensive LEDs are preferred for handheld POCT analyzers. Broadband LEDs are available for UV-VIS EMR, but the UV-VIS LED (first broadband LED) cannot provide sufficient EMR in the longer wavelengths of the visible spectrum or the near-infrared spectrum, illustrated in FIG. 25. Broadband LEDs are also available for VIS (visible) EMR, but the VIS LED (second broadband LED) shown in FIG. 25 illustrates that the LED cannot provide sufficient EMR in the shorter wavelengths of the visible spectrum or the UV spectrum. FIG. 26 illustrates that the absorbances of unaltered blood for the first broadband LED at wavelengths >470 nm are substantially lower than the absorbances of unaltered blood for the second broadband LED at wavelengths >470 nm. One possible explanation is related to the effect of stray EMR discussed previously. It is also observed that the large absorbance peak for Hb observed at ~415 nm is dramatically decreased for the second broadband LED due to the addition of stray EMR to very low levels of incident EMR, and consequently very low levels of emerging EMR. When the incident EMR and the emerging EMR are very low, the effect of stray EMR is more dramatic. Based on their published absorbance profiles illustrated in FIG. 29, measurement of bilirubin species and hemoglobin species in unaltered blood are examples of analytes that could benefit from a composite absorbance spectrum illustrated in FIG. 27.

Provided are various aspects of an analyzer for measuring at least a quantity of a first analyte and a quantity of a second analyte in a blood sample. The analyzer may comprise:

a. A housing.
b. A receptor in the housing. The function of the receptor is for receiving a removable cartridge. The removable cartridge comprises an optical chamber configured for receiving the blood sample.
c. At least two electromagnetic radiation (EMR) sources. The EMR sources may provide a first set of incident EMR to the optical chamber to interrogate the blood sample during a first time interval of a first duration, and a second set of incident EMR to the optical chamber to interrogate the blood sample during a second time interval of a second duration, when the removable cartridge is received in the receptor.
d. An EMR dispersive element. An EMR dispersive element may be a diffraction grating, a prism, or a combination thereof. The diffraction grating may be a reflective diffraction grating or a transmission diffraction grating.
  The EMR dispersive element may produce:
  i. A first blood diffraction spectrum from a first set of emerging EMR emerging from the optical chamber. The first set of emerging EMR may be generated by providing the first set of incident EMR to the optical chamber to interrogate the blood sample during the first time interval.
  ii. A first reference diffraction spectrum. The first reference diffraction spectrum indicates intensities of the first set of incident EMR.
  iii. A second blood diffraction spectrum from a second set of emerging EMR emerging from the optical chamber. The second set of emerging EMR may be generated by providing the second set of incident EMR to the optical chamber to interrogate the blood sample during the second time interval.
  iv. A second reference diffraction spectrum. The second reference diffraction spectrum indicates intensities of the second set of incident EMR.
e. A one-dimensional multi-channel detector. The one-dimensional multi-channel detector may convert:
  i. The first blood diffraction spectrum into a first set of blood digital electrical signals to produce a first blood digital spectrum at a first wavelength range.

ii. The first reference diffraction spectrum into a first set of reference digital electrical signals to produce a first reference digital spectrum at the aforementioned first wavelength range.

iii. The second blood diffraction spectrum into a second set of blood digital electrical signals to produce a second blood digital spectrum at a second wavelength range.

iv. The second reference diffraction spectrum into a second set of reference digital electrical signals to produce a second reference digital spectrum at the afore mentioned second wavelength range.

The one-dimensional multi-channel detector has a saturation EMR intensity at each wavelength. Increases in an intensity of an EMR signal received by the one-dimensional multi-channel detector beyond the saturation EMR intensity do not increase a digital signal derived by the one-dimensional multi-channel detector from that EMR signal. A maximum EMR intensity in the first reference digital spectrum at a wavelength within the first wavelength range and a maximum EMR intensity in the second reference digital spectrum at a wavelength within the second wavelength range exceed 10% of the saturation EMR intensity at the respective wavelengths.

f. A data processor. The data processor may determine:

i. The quantity of the first analyte based on at least a portion of the first blood digital spectrum at a first plurality of wavelengths within the first wavelength range, and the first reference digital spectrum at the first plurality of wavelengths. A first analyte calibration equation may comprise at least one term related to a wavelength from the first wavelength range.

ii. The quantity of the second analyte based on at least a portion of the second blood digital spectrum at a second plurality of wavelengths within the second wavelength range and the second reference digital spectrum at the second plurality of wavelengths. A second analyte calibration equation may comprise at least one term related to a wavelength from the second wavelength range.

An example of a first wavelength range is about 300 nm to about 500 nm and an example of a second wavelength range is about 400 nm to about 1,000 nm.

It should be understood that at least a portion of a digital spectrum implies spectral data at one or more wavelengths. In other words, the smallest portion of a digital spectrum is spectral data at a single wavelength. Therefore, as an example, spectral data at a plurality of wavelengths may imply spectral data at a first wavelength from the first wavelength range, plus spectral data at a second wavelength from the first wavelength range, wherein the first wavelength is not adjacent to the second wavelength. It should also be understood that as examples, the first derivative of absorbance at a single wavelength is calculated from spectral data at a plurality of wavelengths, and smoothened spectral data at a single wavelength is usually calculated from spectral data at a plurality of wavelengths. Therefore, certain processed spectral data at a single wavelength may require spectral data at a plurality of wavelengths in order to accomplish the process. As an example, the first order derivative of absorbance at a wavelength in its simple form is the difference in absorbances at two adjacent wavelengths, and more wavelengths are used for more complex calculations like Savitzky-Golay differentiation filtering. Therefore, at least a portion of a blood digital spectrum at a plurality of wavelengths within a wavelength range could be the first order derivative of absorbance at one wavelength.

It should also be understood that the first analyte calibration equation may comprise any number of terms related to wavelengths within the second wavelength range, and the second analyte calibration equation may comprise any number of terms related to wavelengths within the first wavelength range. Moreover, the contribution of the terms in an analyte calibration equation related to wavelengths within the first or second wavelength ranges, i.e. the weighting factors, could be of any magnitude, and not limit the invention in any way.

An example of a calibration equation for Hb is provided below, which comprises one constant term and four variable terms. In this equation, the constant term is 22.9, and the coefficient of the first variable term (i.e., A545 nm) is 273.

$$g/L\ Hb = 22.9 + (273 \times A545\ nm) + (265 \times 1DA586\ nm) + (6586 \times 1DA615\ nm) - (722 \times A727\ nm).$$

This calibration equation uses a combination of zero order derivative of absorbance and first order derivative of absorbance. A545 nm means zero order derivative of absorbance at a wavelength of 545 nm, and 1DA586 nm means first order derivative of absorbance at a wavelength of 586 nm. "A545 nm" and "1DA586 nm" are two examples of an independent variable, and "g/L HB" is an example of a dependent variable. This equation should not be considered limiting in any way. An example of a method for developing a calibration equation is provided later.

The one-dimensional multi-channel detector has a saturation EMR intensity at each wavelength. Increases in an intensity of an EMR signal received by the one-dimensional multi-channel detector beyond the saturation EMR intensity do not increase a digital signal derived by the one-dimensional multi-channel detector from that EMR signal. Therefore, the saturation EMR intensity for an analyzer comprising an ADC of known bit depth is a finite number for all photo diodes. In order to increase the signal to noise ratio, various embodiments of an analyzer are set to provide a maximum ADC value within a defined wavelength range that is greater than 10% the saturation EMR intensity. In other embodiments of the analyzer, the analyzers are set to provide a maximum ADC value that is greater than 20% the saturation EMR intensity, within the defined wavelength range. Unless specified, the 10% and 20% of the saturation EMR intensity includes background signals. Background signals are expected to vary from analyzer to analyzer depending on the environment, the IT, and the dark current. Greater than 10% the saturation EMR intensity at an IT is usually greater than background electrical signals at that IT. Examples of background electrical signals are illustrated in FIG. 30, and the background intensities at the appropriate IT were subtracted to provide the digital EMR emission spectra shown in FIG. 25.

Background signals are characteristics of the PDA detector and are independent of the EMR sources. EMR emission as detected by the one-dimensional multi-channel detector is usually a distribution of electrical signals across different wavelengths, wherein the distribution may comprise one or more peak EMR intensities, as illustrated in FIG. 25. Greater percent of the saturation EMR intensity may be more useful at wavelengths where the analyte of interest absorbs a substantial amount of the incident EMR because the detector responds to the amount of EMR emerging from the sample and impinging upon the photo diodes. An absorbance of 1 usually implies that 10% of the incident EMR emerges from the sample, an absorbance of 2 usually implies that 1% of the incident EMR emerges from the sample, an absorbance of 3 usually implies that 0.1% of the incident EMR emerges from the sample and so on (see FIGS. 25-27 in conjunction with published absorbance spectra illustrated in FIG. 29). A person having ordinary skill in spectroscopy should appreciate that the published absorbance spectra provided in FIG. 29 uses absorption coefficients instead of absorbance, which is permissible when the sample is non-EMR-scattering. When the sample is EMR-scattering, the displayed absorbance is usually a combination of EMR attenuation due to EMR absorbance and EMR attenuation due to EMR scattering because the PDA detector cannot discriminate between EMR attenuation due to absorbance and EMR attenuation due to scattering. In some situations, less than 1% emerging EMR (i.e. sample signal) may be approaching the level of background electrical signal (also referred to as noise), and sample signal to noise ratio may have a significant impact upon the accuracy and precision of the measured quantity of an analyte. The background signal is usually directly proportional to IT as illustrated in FIG. 30. As an example, 16-bit ADC can produce 65,536 discrete ADC values, therefore the saturation digital EMR intensity is 65,536 for a 16-bit ADC. Moreover, the analog equivalent of 65,536 ADC numbers is the maximum electrical output of a photo diode in response to EMR impinging upon the photo diode.

In an embodiment, the first EMR source of an analyzer may comprise an ultraviolet (UV) LED having a wafer comprising fluorescent material. The wafer having fluorescent material may be attached to an EMR emitting surface of the UV LED. The fluorescent material may be in the form of fluorescent particles. After the wafer having fluorescent material receives UV EMR from the UV LED, the wafer may produce at least a portion of the first set of incident EMR. In such a case, at least a portion of the first set of incident EMR may be fluorescence emission. The wafer having fluorescent material, may further comprise silicon, silicon dioxide, quartz, glass, or any combination thereof. The second EMR source may be, for example, a white LED, a white-near infrared LED, an incandescent lamp or a fluorescent lamp. The UV LED or the UV LED and at least one other LED may be encased in a container having a glass filter. The glass filter may be used to protect the LEDs and/or may be used to absorb some of the UV EMR emerging from the UV LED at wavelengths shorter than about 300 nm. The UV LED may emit EMR towards the wafer within an approximate wavelength range of about 200 nm to about 400 nm, and the resulting wavelength range of the fluorescence emission may be about 300 nm to about 500 nm. It should be understood that this UV LED is simply an example of a broadband LED, and the use of fluorescence is an example of a means for producing EMR within the approximate range of about 300 nm to about 500 nm, in order to supplement the EMR emission from the second broadband LED. In an embodiment, the first broadband LED may be a UV-VIS LED with emission EMR within the approximate range of about 300 nm to about 500 nm. This UV-VIS LED may not have a wafer comprising fluorescent material, therefore the EMR emission may not comprise any fluorescence emission. In other embodiments, the first set of incident EMR may comprise a combination of fluorescence and VIS EMR, a combination of fluorescence and UV EMR, and a combination of fluorescence and UV-VIS EMR, and these sources of EMR may or may not be LEDs.

In an embodiment with two EMR sources, the two EMR sources may be controlled by a data processor so that the first time interval and the second time interval occur such that they do not overlap in time. The two EMR sources may also be controlled by the data processor so that the first time interval and the second time interval may occur such that at least a portion of the first time interval occurs when the second time interval is not occurring, and at least a portion of the second time interval occurs when the first time interval is not occurring.

Non limiting examples of the first analyte and the second analyte are a species of bilirubin and a species of hemoglobin. The analyzer may further comprise a non-transient computer-readable memory for storing calibration equations for determining from spectral information the quantity of analytes, for example, a species of bilirubin and a species of hemoglobin. The non-transient computer-readable memory may further store an analyzer-specific wavelength table and a standard wavelength table. A standard wavelength table comprises a set of wavelengths defined by a range and an arbitrarily chosen increment, wherein the range at least encompasses wavelengths associated with the terms of the analyte calibration equations that are implemented in the analyzers. The range of the standard wavelength table may be expanded to accommodate the wavelengths associated with the terms of calibration equations for other analytes. For each analyzer, the one-dimensional multi-channel detector comprises a linear repetitive installation of an associated plurality of discrete photo diodes on an integrated circuit chip. The analyzer-specific wavelength table indicates a wavelength assigned to each photo diode in the associated plurality of discrete photo diodes of the one-dimensional multi-channel detector of that analyzer after a process of wavelength calibration, which was discussed previously. In operation, a data processor of an analyzer may map portions of a blood digital spectrum and corresponding portions of a reference digital spectrum onto wavelengths of the standard wavelength table, to enable a child analyzer to use calibration equations for analytes developed using data from a parent analyzer.

An example of an analyzer that measures bilirubin and hemoglobin is Radiometer ABL 90 Flex Plus, which is like several other analyzers that can measure analytes in whole blood, including hemoglobin and bilirubin. Instructions for use of the Radiometer ABL 90 Flex Plus from software version 3.4, version 2018051 (available on the internet as https://www.uclahealth.org/respiratory-care/workfiles/POC/ABL90%20FLEVA20PLUS%20INSTRUCTIONS%20FOR%20USE%20v3.4.pdf) describes a spectrophotometer for measuring bilirubin and hemoglobin species. In the manual under "Measurement Cycle" (pg 364), it is stated: "The 1-µL sample in the cuvette is ultrasonically hemolyzed at a frequency of about 30 KHz. This hemolyzation process ruptures the walls of the red blood cells and the content of the red blood cells is evenly mixed with the plasma and an optically clear solution is produced." Lambert-Beer's law can be applied to an optically clear solution produced after ultrasonic hemolyzation. Pg 365 states: "Absorption spectroscopy is based on Lambert-Beer's law, which states that the measured absorbance for a single compound is directly proportional to the concentration of the compound and the length of the light path through the sample." A person skilled in spectroscopy should appreciate that Lambert-Beer's law cannot be applied to unaltered blood because the intact red blood cells scatter the incident EMR, further attenuating EMR impinging upon the photo diodes. The detector cannot discriminate EMR attenuation due to scattering, from EMR attenuation due to absorbance by pigments such as hemoglobin and bilirubin. An embodiment of the analyzer described in this application is an example of an analyzer that lacks a hemolyzing means for altering the blood through hemolysis to produce an optically clear solution. Therefore, unaltered blood that comprises most of the red blood cells drawn from a patient may be tested or measured. The absence of hemolyzing means like an ultrasonic element provides an advantage of making an analyzer simpler and smaller for POCT. Optionally, the removable cartridge may comprise dry hemolyzing chemicals, for example sodium deoxycholate, so that the blood becomes hemolyzed as it solubilizes the dry hemolyzing chemical(s).

The ABL 90 Flex Plus manual also states on pg 364: "The optical system is based on a 256-wavelength spectrophotometer with a measuring range of 467-672 nm." Bilirubin has a maximum absorbance at about 454 nm (see FIG. 29), and the absorbance signal in the range of 467 nm to 672 nm due to bilirubin may be lost in noise due to EMR scattering when unaltered blood is used. EMR scattering is inversely proportional to wavelength, therefore the EMR is more attenuated by scattering at the shorter wavelengths, making it difficult to measure bilirubin in unaltered blood with an acceptable level of accuracy. A broadband LED having EMR emission at wavelengths within the range of about 300 nm to about 500 nm may be used to supplement an EMR source having EMR emission at longer wavelengths, for example, a wavelength range of 400 nm to about 1,000 nm. The use of two EMR sources differentiates the present invention from the Radiometer ABL 90 Flex Plus FIG. 26 illustrates how the absorbance of the first broadband LED decreases at wavelengths longer than 470 nm because the emission of EMR interrogating the sample is very low (see FIG. 25), decreasing the signal to noise ratio, and furthermore, stray EMR may affect the absorbances. Similarly, FIG. 26 illustrates how the absorbance of the second broadband LED decreases at wavelengths shorter than 470 nm because the emission of EMR interrogating the sample is very low (see FIG. 25), decreasing the signal to noise ratio, and stray EMR may affect the absorbances. The EMR emerging from the sample may be truncated and a composite absorbance spectrum may be created as shown in FIG. 27. In order to create a composite absorbance spectrum, the first broadband LED should interrogate the blood in the optical chamber during first time interval of a first duration, and the second broadband LED should interrogate the blood in the optical chamber during a second time interval of a second duration. The durations of the first time interval and the second time interval depends on the power supplied to the LED, and the desired intensity of the EMR emission. In the examples of EMR emission illustrated in FIG. 25, the first broadband LED was at 40% power and the duration was 300 milliseconds, and the second broadband LED was at 64% power and the duration was 60 milliseconds. It should be appreciated that the shorter EMR wavelengths generate heat proportional to the power provided to the LED, and the heat may decrease the lifetime of the LED. Therefore, it may be beneficial to provide less power to the UV LED for a longer duration to achieve a desired EMR emission.

The following are examples of time intervals, for illustrating when two time intervals are the same or different. For illustration, a first time interval begins at time T1 and ends at time T2, and a second time interval begins at time T3 and ends at time T4. If T1=T3 and T2=T4, the first time interval and the second time interval are the same, and the durations of the first and second time intervals are the same. If T1=T3 and T2≠T4, the first time interval is different from the second time interval, and the durations of the first and second time intervals are not the same. If T1≠T3 and T2=T4, the first time interval is different from the second time interval, and the durations of the first and second time intervals are not the same. If T1≠T3 or T4, and T2≠T3 or T4, the first and second time intervals are different and there may or may not be any overlap between the first and second time intervals.

Calibration algorithms may be developed using the full composite spectrum (for example, partial least squares statistical analysis, and principal component analysis), or selected wavelengths (for example, multiple linear regression statistical analysis). The statistical analysis may use transmission, reflectance or absorbance, or an order derivative of transmittance, reflectance or absorbance, or a combination of order derivatives. As an example, a calibration equation may be developed using a combination of zero and first order derivative of absorbance (an example was shown earlier for Hb). First order derivative of absorbance at a wavelength is the slope of the absorbance curve at that wavelength. Zero order derivative of absorbance, zero order derivative of transmittance and zero order derivative of reflectance are the raw absorbance, the raw transmittance, and the raw reflectance respectfully.

Provided are various aspects of a system for measuring at least a quantity of a first analyte and a quantity of a second analyte in a blood sample. The system comprises a removable cartridge having an optical chamber for receiving the blood sample, and an analyzer. Aspects of an analyzer were previously described. Examples of removable cartridges comprising optical chambers 412b, 412e, 412f, 412g, and 412h are provided in FIGS. 9A-9G, FIGS. 13A-14F, FIGS. 16A-17D, FIGS. 19A-21J, and FIGS. 22A-23D respectively. A removeable cartridge may be a single-use removeable cartridge.

Various embodiments of the system may comprise a plurality of similar removeable cartridges and a plurality of similar analyzers as discussed previously. the analyzer comprises a plurality of analyzers, the plurality of analyzers comprising one or more parent analyzers and one or more child analyzers. In operation, the one or more parent analyzers provide data to develop a first analyte calibration and a second analyte calibration equation and subsequently, the first analyte calibration equation and the second analyte calibration equation are transferred to the one or more child analyzers;

An analyzer of the plurality of analyzers may further comprise an associated non-transient computer-readable memory for storing:
   i. A first analyte calibration equation for determining from spectral information the quantity of a first analyte.
   ii. A second analyte calibration equation for determining from spectral information the quantity of a second analyte.
   iii. An analyzer-specific wavelength table, specific to that analyzer.
   iv. A standard wavelength table comprising a set of wavelengths defined by a range and an arbitrarily chosen increment, wherein the range at least encompasses, wavelengths of the spectral information associated with the terms of first analyte calibration equation and wavelengths of the spectral information associated with the terms of the second analyte calibration equation.

The data processor of an analyzer of a plurality of analyzers may map at least a portion of the first blood digital spectrum at the first plurality of wavelengths, at least a portion of the first reference digital spectrum wherein the portion corresponds with the portion of the first blood digital spectrum, at least a portion of the second blood digital spectrum at the second plurality of wavelengths, at least a portion of the second reference digital spectrum wherein the portion corresponds with the portion of the second blood digital spectrum, onto the standard wavelength table. This mapping process may enable a first analyte calibration equation and a second analyte calibration equation to be installed on an uncalibrated analyzer. A calibration equation developed on a parent analyzer (i.e., the analyzer calibrated) and subsequently installed on an uncalibrated analyzer (referred to as a child analyzer) may be referred to as factory calibration or calibration transfer.

In some embodiments of the system, the analyzer lacks a hemolyzing means for altering the blood to an optically clear solution, such that, in operation, the interrogated blood sample within the optical chamber may comprise most of the red blood cells drawn from a patient.

Provided are various aspects of a method for measuring at least a quantity of a first analyte and a quantity of a second analyte in a blood sample. As non-limiting examples, the first analyte may be a species of bilirubin and the second analyte may be a species of hemoglobin. The method may comprise:
   a. Providing the blood sample to an optical chamber.
   b. Operating at least two EMR sources to produce a first set of emerging EMR and a second set of emerging EMR by interrogating the blood sample within the optical chamber, respectively with a first set of incident EMR during a first time interval of a first duration, and a second set of incident EMR during a second time interval of a second duration.
   c. Producing a first blood diffraction spectrum from the first set of emerging EMR emerging from the optical chamber.
   d. Producing a second blood diffraction spectrum from a second set of emerging EMR emerging from the optical chamber.
   e. Operating a one-dimensional multi-channel detector to convert the first blood diffraction spectrum into a first set of blood digital electrical signals to produce a first blood digital spectrum at a first wavelength range.
   f. Operating the aforementioned one-dimensional multi-channel detector to convert the second blood diffraction spectrum into a second set of blood digital electrical signals to produce a second blood digital spectrum at a second wavelength range.
   g. Operating a data processor to determine the quantity of the first analyte based on:
      I. At least a portion of the first blood digital spectrum at a first plurality of wavelengths within the first wavelength range.
      II. At least a portion of a first reference digital spectrum indicating intensities of the aforementioned first set of incident EMR at the first plurality of wavelengths.
   h. Operating a data processor to determine the quantity of the second analyte based on:
      I. At least a portion of the second blood digital spectrum at a second plurality of wavelengths within the second wavelength range.
      II. At least a portion of a second reference digital spectrum indicating intensities of the aforementioned second set of incident EMR at the second plurality of wavelengths.

The optical chamber is usually part of a removable cartridge, the at least two EMR sources and the data processor(s) is(are) usually part of an analyzer, and the removable cartridge is receivable within a receptor of the analyzer. Various embodiments of the method defined above may further comprise a step of inserting the removable cartridge into the receptor, and then operating the analyzer to determine the quantity of the first analyte and the quantity of the second analyte.

Various embodiments of the method defined above may further comprise producing the first reference digital spectrum, wherein producing the first reference digital spectrum comprises providing the first set of incident EMR for the first duration when the receptor is devoid of blood, and producing the second reference digital spectrum, wherein producing the second reference digital spectrum comprises providing the second set of incident EMR for the second duration when the receptor is devoid of blood.

Various embodiments of the method defined above for measuring a quantity of a first analyte and a quantity of a second analyte in each blood sample of a plurality of blood samples may further comprise a step of storing at least one of the first reference digital spectrum and the second reference digital spectrum in a non-transient computer-readable memory. Subsequently, for each blood sample of the plurality of blood samples, the method may further comprise a step of retrieving the relevant reference digital spectrum from the non-transient computer-readable memory and operating the data processor to determine the quantity of the first and/or second analyte using the retrieved reference digital spectrum. The method may further comprise, periodically updating the first reference digital spectrum and the second reference digital spectrum stored in the non-transient computer-readable memory.

Various embodiments of the method defined above may further comprise:
   a. Storing a first analyte calibration equation for determining from spectral information the quantity of the first analyte, and storing a second analyte calibration equation for determining from spectral information the quantity of the second analyte, in a non-transient computer-readable memory.
   b. Operating a data processor to determine the quantity of the first analyte, wherein operating comprises determining the quantity of the first analyte from the at least a portion of the first blood digital spectrum at the first plurality of wavelengths, the at least a portion of the first reference digital spectrum at the first plurality of wavelengths, and the first analyte calibration equation.
   c. Operating a data processor to determine the concentration of the second analyte, wherein operating comprises determining the concentration of the second analyte from the at least a portion of the second blood digital spectrum at the second plurality of wavelengths, the at least a portion of the second reference digital spectrum at the second plurality of wavelengths, and the second analyte calibration equation.

Various embodiments of the method as defined above, further provides as an example, a method for developing analyte calibration equations on one or more parent analyzers. In other words, an analyte calibration equation may be developed using spectral data from one or more analyzers, referred to as parent analyzers, and know analyte quantities in a sample set referred to as a calibration set. This example provides a method for developing a first analyte calibration equation a second analyte calibration equation. A similar process may be followed to include other analytes. Subsequently, the developed analyte calibration equations may be installed on the analyzer associated non-transient computer-readable memory of other analyzers, so that the other analyzers need not be calibrated for the analytes; this process may be referred to as calibration equation transfer from one or more analyzers (referred to as parent analyzers) to other analyzers, (referred to as child analyzers) and the process facilitates factory calibration of analyzers. An example of a calibration equation for Hb was provided earlier. Therefore, the method for measuring a quantity of a first analyte and a quantity of a second analyte in a blood sample may further comprise:

a. Acquiring a first analyte calibration set comprising greater than ten blood samples having greater than ten known first analyte quantities.

b. Acquiring a second analyte calibration set comprising greater than ten blood samples having greater than ten known second analyte quantities. The second analyte calibration set may be the same as or different from the first analyte calibration set. Spectral information of a blood sample can only be used for an analyte calibration when accompanied by a known quantity of the analyte. Preferably, a calibration set should be greater than ten. Larger calibration sets with samples that include more variables, for example, variabilities in samples from patients with various illnesses, may be used to prepare more robust calibration equations. The calibration process may use data from a single parent analyzer or may use pooled data from a plurality of parent analyzers. It may be advantageous to pool data from a plurality of parent analyzers, whereby analyzer variabilities may become built into the calibration equations. A calibration set may also be referred to as a training set, in that the analyzer is trained to recognize certain interferents in patient blood samples.

c. Collecting a set of first analyte calibration spectral information comprising a first blood digital spectrum and a second blood digital spectrum for each blood sample of the first analyte calibration set, whereby each sample of the first analyte calibration set is accompanied by a known quantity of the first analyte.

d. Collecting a set of second analyte calibration spectral information comprising a first blood digital spectrum and a second blood digital spectrum for each blood sample of the second analyte calibration set, whereby each sample of the second analyte calibration set is accompanied by a known quantity of the second analyte.

e. Producing one or more of the first reference digital spectrum.

f. Producing one or more of the second reference digital spectrum.

g. Developing the first analyte calibration equation by applying known chemometric techniques to the set of first analyte calibration spectral information, the one or more of the first reference digital spectrum, the one or more of the second reference digital spectrum, the greater than ten known first analyte quantities.

h. Developing the second analyte calibration equation by applying known chemometric techniques to the set of second analyte calibration spectral information, the one or more of the first reference digital spectrum, the one or more of the second reference digital spectrum, and the greater than ten known second analyte quantities.

In some embodiments, one of the plurality of a first the reference digital spectrum and one of the plurality of the second reference digital spectrum are collected either before or after collecting the spectral information for each blood sample of the first analyte calibration set and each blood sample of the second analyte calibration set. Optionally, one first reference digital spectrum and one second reference digital spectrum may be produced and stored on the analyzer associated non-transient computer-readable memory and operating the at least one data processor for retrieving the first reference digital spectrum and the second reference digital spectrum from the non-transient computer-readable memory for applying the known chemometric techniques.

Various embodiments of the method defined above may further comprise:

a. Producing the first reference digital spectrum, wherein producing the first reference digital spectrum comprises providing the first set of incident EMR when the removable cartridge is not within the receptor.

b. Producing the second reference digital spectrum, wherein producing the second reference digital spectrum comprises providing the second set of incident EMR when the removable cartridge is not within the receptor.

Various embodiments of the method defined above may further comprise controlling a timing of the first time interval and the second time interval to overlap or not overlap. Also, the duration of the time interval for producing the first set of EMR may be the same as or different from the duration of the time interval for producing the second set of EMR.

In some embodiments, determining the quantity of the first analyte may comprise deriving one of an order derivative of absorbance, transmittance, and reflectance data, or any combination thereof, from the at least a portion of the first digital spectrum. It should be understood that at least a portion of a digital spectrum implies spectral data at one or more wavelengths. In other words, the smallest portion of a digital spectrum is spectral data at a single wavelength. Therefore, as an example, spectral data at a plurality of wavelengths may imply spectral data at a first wavelength from the second wavelength range, plus spectral data at second wavelength from the second wavelength range, wherein the first wavelength is not adjacent to the second wavelength. Determining the quantity of the first analyte may also comprise deriving one of a zero order derivative of absorbance, a first order derivative of absorbance, a second order derivative of absorbance from the at least a portion of the first digital spectrum, or any combination thereof.

The blood sample drawn from a patient initially includes a plurality red blood cells and providing the blood sample to an optical chamber and interrogating the blood sample within the optical chamber may comprise providing and interrogating the blood sample without breaking down most of the plurality red blood cells. Therefore, in some embodiments, the method may be devoid of a step of hemolyzing the blood sample before measurement, making the analyzer less complex.

The quantity of any analyte that provides a transmittance, reflectance or absorbance spectral change at one or more wavelengths with a change in the quantity of the analyte may be measured by spectroscopy. Non-limiting examples of quantities of analytes may include: 1) a species of hemoglobin; 2) a species of bilirubin; 3) % Glycated Hemoglobin; 4) % HbA1c; and CO-oximetry. CO-oximetry includes Fractional hemoglobin (Hb) oxygen saturation (the ratio of a quantity of Oxy-Hb in a blood sample to the sum of the quantities of other Hb species, usually Oxy-Hb, Deoxy-Hb, Met-Hb, and Carboxy-Hb, in the same blood sample); and functional Hb oxygen saturation (the ratio of a quantity of Oxy-Hb in a blood sample to the sum of the quantities of Oxy-Hb and Deoxy-Hb, in the same blood sample).

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein. Furthermore, the discussed combination of features might not be absolutely necessary for the inventive solution.

We claim:

1. A system for measuring at least a quantity of a first analyte and a quantity of a second analyte in a blood sample, the system comprising:
a removable cartridge comprising an optical chamber for receiving the blood sample,
the optical chamber comprising one or more optical windows for transmitting electromagnetic radiation (EMR) into and out of the optical chamber and the removable cartridge; and,
an analyzer comprising:
a housing;
a receptor in the housing for receiving the removable cartridge;
at least two EMR sources positioned in the housing to be aligned with an optical window of the one or more optical windows when the removable cartridge is received in the receptor, the at least two EMR sources being configured to emit different wavelengths of EMR into the receptor, and, when the removable cartridge is received in the receptor, to emit the different wavelengths of EMR into the optical chamber of the removable cartridge via that optical window, the at least two EMR sources being configured to provide
a first set of incident EMR into the optical chamber via that optical window of the one or more optical windows to interrogate the blood sample during a first time interval of a first duration, and
a second set of incident EMR into the optical chamber via that optical window of the one or more optical windows to interrogate the blood sample during a second time interval of a second duration;
an EMR dispersive element positioned in the housing to be aligned with EMR emerging from the optical chamber when the removable cartridge is received in the receptor and operable to disperse EMR emerging from the blood via an optical window of the one or more optical windows to produce
a first blood diffraction spectrum from a first set of emerging EMR emerging from the optical chamber, the first set of emerging EMR being generated by providing the first set of incident EMR to the optical chamber to interrogate the blood sample during the first time interval;
a first reference diffraction spectrum, wherein the first reference diffraction spectrum indicates intensities of the first set of incident EMR;
a second blood diffraction spectrum from a second set of emerging EMR emerging from the optical chamber, the second set of emerging EMR being generated by providing the second set of incident EMR to the optical chamber to interrogate the blood sample during the second time interval;
a second reference diffraction spectrum, wherein the second reference diffraction spectrum indicates intensities of the second set of incident EMR;
a one-dimensional multi-channel detector comprising an array of discrete detectors for measuring wavelength-specific dispersed emerging EMR;
and analog to digital converter for converting
the first blood diffraction spectrum into a first set of blood digital electrical signals to produce a first blood digital spectrum at a first wavelength range;
the first reference diffraction spectrum into a first set of reference digital electrical signals to produce a first reference digital spectrum at the first wavelength range;
the second blood diffraction spectrum into a second set of blood digital electrical signals to produce a second blood digital spectrum at a second wavelength range;
the second reference diffraction spectrum into a second set of reference digital electrical signals to produce a second reference digital spectrum at the second wavelength range;
wherein
each of the discrete detectors of the one-dimensional multi-channel detector having a saturation EMR intensity
wherein, increases in an intensity of an EMR signal received by each of the discrete detectors of the one-dimensional multi-channel detector beyond the saturation EMR intensity do not increase a digital signal derived by each of the discrete detectors of the one-dimensional multi-channel detector from that EMR signal, and,
a maximum EMR intensity in the first reference digital spectrum at a the specific wavelengths within the first wavelength range and a maximum EMR intensity in the second reference digital spectrum at the specific wavelengths within the second wavelength range exceed 10% of the saturation EMR intensity at the respective wavelengths;
at least one data processor for determining
the quantity of the first analyte based on at least a portion of the first blood digital spectrum at a first plurality of wavelengths within the first wavelength range and the first reference digital spectrum at the first plurality of wavelengths; and,
the quantity of the second analyte based on at least a portion of the second blood digital spectrum at a second plurality of wavelengths within the second wavelength range and the second reference digital spectrum at the second plurality of wavelengths.

2. The system as defined in claim 1 wherein
the at least two EMR sources comprise an EMR source;
the EMR source comprises an ultraviolet (UV) LED and
a wafer having fluorescent material, wherein the wafer is attached to an EMR emitting surface of the UV LED; and,
in operation, upon receiving UV EMR from the UV LED, the wafer having fluorescent material produces at least a portion of the first set of incident EMR; and,
the at least a portion of the first set of incident EMR is fluorescence emission.

3. The system as defined in claim 2 wherein the at least two EMR sources further comprises a second EMR source, the second EMR source being one of a white LED, a white-near infrared LED, an incandescent lamp and a fluorescent lamp.

4. The system as defined in claim 2 wherein the wafer having fluorescent material, further comprises at least one of silicon, silicon dioxide, quartz, and glass.

5. The system as defined in claim 2, wherein the EMR source further comprises a glass filter for at least absorbing some of the UV EMR emerging from the UV LED at wavelengths shorter than about 300 nanometers.

6. The system as defined in claim 2 wherein the UV LED emits EMR towards the wafer within an wavelength range of about 200 nanometers to about 400 nanometers.

7. The system as defined in claim 2 wherein the wavelength of maximum EMR intensity of the first set of incident EMR is within the wavelength range of about 300 nm to about 500 nm.

8. The system as defined in claim 1 wherein, in operation, the at least one data processor controls the operating of the at least two EMR sources to control when the first time interval and the second time interval occur such that
at least a portion of the first time interval occurs when the second time interval is not occurring; and,
at least a portion of the second time interval occurs when the first time interval is not occurring.

9. The system as defined in claim 1 wherein, in operation, the at least one data processor controls when the first time interval and the second time interval occur such that the first time interval and the second time interval do not overlap in time.

10. The system as defined in claim 1 wherein the maximum EMR intensity in the first reference digital spectrum at a wavelength within the first wavelength range and the maximum EMR intensity in the second reference digital spectrum at a wavelength within the second wavelength range exceed 20% of the saturation EMR intensity at the respective wavelengths.

11. The system as defined in claim 1 wherein the EMR dispersive element is one of a diffraction grating, a prism, and a combination thereof, and wherein the diffraction grating is one of a reflective diffraction grating and a transmission diffraction grating.

12. The system as defined in claim 1 wherein the at least two EMR sources, the one-dimensional multi-channel detector, the EMR dispersive element, and the at least one processor are fixedly attached to the housing such that the at least two EMR sources, the one-dimensional multi-channel detector, the EMR dispersive element, and the at least one processor are stationary relative to the housing and each other.

13. The system as defined in claim 1, further comprising a fiber optic cable for directing the first set of emerging EMR and the second set of emerging EMR to the EMR dispersive element.

14. The system as defined in claim 1 wherein the first wavelength range is about 300 nm to about 500 nm, and the second wavelength range is about 400 nm to about 1,000 nm.

15. The system as defined in claim 1 wherein the removeable cartridge is a single-use removeable cartridge.

16. The system as defined in claim 15 wherein the single-use removeable cartridge comprises a plurality of single-use removeable cartridges.

17. The system as defined in claim 1 wherein
the analyzer comprises a plurality of analyzers, the plurality of analyzers comprising one or more parent analyzers and one or more child analyzers,
the one or more parent analyzers to provide data to develop a first analyte calibration equation and a second analyte calibration equation and subsequently, the first analyte calibration equation and the second analyte calibration equation are to be transferred to the one or more child analyzers;
each analyzer of the plurality of analyzers further comprises an associated non-transient computer-readable memory, and, stored on the associated non-transient computer-readable memory,
an analyzer-specific wavelength table specific to that analyzer,
a first analyte calibration equation for determining from spectral information the quantity of the first analyte,
a second analyte calibration equation for determining from spectral information the quantity of the second analyte, and
a standard wavelength table comprising a set of wavelengths defined by a range and an arbitrarily chosen increment, wherein the range at least encompasses, wavelengths of the spectral information associated with the first analyte calibration equation and wavelengths of the spectral information associated with the second analyte calibration equation;
for each analyzer of the plurality of analyzers,
the one-dimensional multi-channel detector for that analyzer comprises a linear repetitive installation of an associated plurality of discrete photo diodes on an integrated circuit chip;
the analyzer-specific wavelength table indicates a wavelength assigned to each photo diode in the associated plurality of discrete photo diodes of the one-dimensional multi-channel detector of that analyzer after a process of wavelength calibration; and,
in operation, the at least one data processor of that analyzer maps the at least a portion of the first blood digital spectrum at the first plurality of wavelengths, at least a portion of the first reference digital spectrum wherein the portion corresponds with the portion of the first blood digital spectrum, the at least a portion of the second blood digital spectrum at the second plurality of wavelengths, at least a portion of the second reference digital spectrum wherein the portion corresponds with the portion of the second blood digital spectrum, onto the standard wavelength table, to enable that analyzer to use the first analyte calibration equation and the second analyte calibration equation.

18. The system as defined in claim 1, wherein the analyzer lacks a hemolyzing means for altering the blood to an optically clear solution, such that, in operation, the blood sample interrogated within the optical chamber comprises most of the red blood cells drawn from a patient.

19. A method for measuring at least a quantity of a first analyte and a quantity of a second analyte in a blood sample received in the optical chamber of a removable cartridge, the optical chamber comprising one or more optical windows for transmitting electromagnetic radiation (EMR) into and out of the optical chamber and the removable cartridge, the method comprising:
providing the blood sample to the optical chamber;
inserting the removable cartridge into the receptor of an analyzer, the analyzer further comprising at least two EMR sources, an EMR dispersive element, a one-dimensional multi-channel detector having an array of discrete detectors for measuring wavelength-specific dispersed emerging EMR, at least one analog to digital converter, and at least one data processor;

aligning an optical window of the one or more optical windows with the at least two EMR sources, the at least two EMR sources being configured to emit different wavelengths of EMR into the receptor, to emit the different wavelengths of EMR into the optical chamber of the removable cartridge via that optical window;

operating the at least two electromagnetic radiation (EMR) sources to produce a first set of emerging EMR and a second set of emerging EMR by interrogating the blood sample within the optical chamber, respectively with a first set of incident EMR during a first time interval of a first duration, a second set of incident EMR during a second time interval of a second duration, operating the EMR dispersive element to produce a first blood diffraction spectrum from the first set of emerging EMR emerging from the optical chamber;

operating the EMR dispersive element to producing produce a second blood diffraction spectrum from the second set of emerging EMR emerging from the optical chamber;

operating the one-dimensional multi-channel detector and the analog to digital converter to convert the first blood diffraction spectrum into a first set of blood digital electrical signals to produce a first blood digital spectrum at a first wavelength range;

the second blood diffraction spectrum into a second set of blood digital electrical signals to produce a second blood digital spectrum at a second wavelength range;

operating the at least one data processor to determine the quantity of the first analyte based on at least a portion of the first blood digital spectrum at a first plurality of wavelengths within the first wavelength range and a first reference digital spectrum indicating intensities of the first set of incident EMR at the first plurality of wavelengths; and, determine the quantity of the second analyte based on at least a portion of the second blood digital spectrum at a second plurality of wavelengths within the second wavelength range and a second reference digital spectrum indicating intensities of the second set of incident EMR at the second plurality of wavelengths;

wherein each of the discrete detectors of the one-dimensional multi-channel detector has a saturation EMR intensity;

increases in an intensity of an EMR signal received by each of the discrete detectors of the one-dimensional multi-channel detector beyond the saturation EMR intensity do not increase a digital signal derived by each of the discrete detectors of the one-dimensional multi-channel detector in response to that EMR signal; and, a maximum EMR intensity in the first reference digital spectrum at a wavelength within the first wavelength range and a maximum EMR intensity in the second reference digital spectrum at a wavelength within the second wavelength range exceed 10% of the saturation EMR intensity at the respective wavelengths.

20. The method as defined in claim 19 wherein the first analyte is a species of bilirubin and the second analyte is a species of hemoglobin.

21. The method as defined in claim 19 wherein
the optical chamber is part of a removable cartridge,
the at least two EMR sources, and the at least one data processor are part of an analyzer;
the removable cartridge is receivable within a receptor of the analyzer; and,
the method further comprises inserting the removable cartridge into the receptor, and then operating the analyzer to determine the quantity of the first analyte and the quantity of the second analyte.

22. The method as defined in claim 21 further comprising:
producing the first reference digital spectrum, wherein producing the first reference digital spectrum comprises providing the first set of incident EMR for the first duration when the receptor is devoid of blood; and,
producing the second reference digital spectrum, wherein producing the second reference digital spectrum comprises providing the second set of incident EMR for the second duration when the receptor is devoid of blood.

23. A method for measuring a quantity of a first analyte and a quantity of a second analyte in each blood sample of a plurality of blood samples, the method comprising,
for each blood sample of the plurality of blood samples, determining the quantity of the first analyte and the quantity of the second analyte as defined in claim 19; and,
storing at least one of the first reference digital spectrum and the second reference digital spectrum in a non-transient computer-readable memory;
wherein, for each blood sample of the plurality of blood samples,
operating the at least one data processor to determine the quantity of the first analyte comprises retrieving the first reference digital spectrum from the non-transient computer-readable memory, or
operating the at least one data processor to determine the quantity of the second analyte comprises retrieving the second reference digital spectrum from the non-transient computer-readable memory.

24. The method as defined in claim 23 further comprising periodically updating the first reference digital spectrum and the second reference digital spectrum stored in the non-transient computer-readable memory.

25. The method as defined in claim 19 wherein the at least two EMR sources comprise a first EMR source for providing the first set of incident EMR, and a second EMR source for providing the second set of incident EMR.

26. The method as defined in claim 19 further comprising storing, in a non-transient computer-readable memory, a first analyte calibration equation for determining from spectral information the quantity of the first analyte, and a second analyte calibration equation for determining from spectral information the quantity of the second analyte, wherein
operating the at least one data processor to determine the quantity of the first analyte comprises determining the quantity of the first analyte from the at least a portion of the first blood digital spectrum at the first plurality of wavelengths, the first reference digital spectrum at the first plurality of wavelengths, and the first analyte calibration equation; and,
operating the at least one data processor to determine the quantity of the second analyte comprises determining the quantity of the second analyte from the at least a portion of the second blood digital spectrum at the second plurality of wavelengths, the second reference digital spectrum at the second plurality of wavelengths, and the second analyte calibration equation.

27. The method as defined in claim 21 further comprising producing the first reference digital spectrum, wherein producing the first reference digital spectrum comprises providing the first set of incident EMR when the removable cartridge is not within the receptor; and, producing the second reference digital spectrum, wherein producing the second reference digital spectrum comprises providing the second set of incident EMR when the removable cartridge is not within the receptor.

28. The method as defined in claim 19 further comprising controlling a timing of the first time interval and the second time interval to not overlap.

29. The method as defined in claim 26, wherein determining the quantity of the first analyte comprises deriving one of, an order derivative of absorbance, an order derivative of transmittance, an order derivative of reflectance data, and any combination thereof, from the at least a portion of the first digital spectrum at the first plurality of wavelengths.

30. The method as defined in claim 26, wherein determining the quantity of the first analyte comprises deriving one of, a zero order derivative of absorbance, a first order derivative of absorbance, a second order derivative of absorbance, and any combination thereof, from the at least a portion of the first digital spectrum.

31. The method as defined in claim 19 wherein
the blood sample drawn from a patient initially includes a plurality red blood cells, and
providing the blood sample to an optical chamber and interrogating the blood sample within the optical chamber comprise providing and interrogating the blood sample without breaking down most of the plurality red blood cells.

32. The method as defined in claim 19 wherein the maximum EMR intensity in the first reference digital spectrum at a wavelength within the first wavelength range and the maximum EMR intensity in the second reference digital spectrum at a wavelength within the second wavelength range exceed 20% of the saturation EMR intensity at the respective wavelengths.

33. The method as defined in claim 26 further comprising developing the first analyte calibration equation and developing the second calibration equation, comprising:
acquiring a first analyte calibration set having greater than ten first analyte calibration blood samples, the first analyte calibration set having greater than ten known first analyte quantities;
acquiring a second analyte calibration set having greater than ten second analyte calibration blood samples, the second analyte calibration set having greater than ten known second analyte quantities;
collecting a set of first analyte calibration spectral information comprising a first blood digital spectrum and a second blood digital spectrum for each of the first analyte calibration blood samples;
collecting a set of second analyte calibration spectral information comprising a first blood digital spectrum and a second blood digital spectrum for each of the second analyte calibration blood samples;
producing one or more of the first reference digital spectrum;
producing one or more of the second reference digital spectrum;
developing the first analyte calibration equation by applying known chemometric techniques to the set of first analyte calibration spectral information, the one or more of the first reference digital spectrum, the one or more of the second reference digital spectrum, the greater than ten known first analyte quantities; and
developing the second analyte calibration equation by applying known chemometric techniques to the set of second analyte calibration spectral information, the one or more of the first reference digital spectrum, the one or more of the second reference digital spectrum, and the greater than ten known second analyte quantities.

\* \* \* \* \*